United States Patent
Matsuhisa et al.

(10) Patent No.: US 6,340,678 B1
(45) Date of Patent: Jan. 22, 2002

(54) 4,4-DIFLUORO-2,3,4,5-TETRAHYDRO-1H-1-BENZOAZEPINE DERIVATIVES AND DRUG COMPOSITIONS CONTAINING THEM

(75) Inventors: Akira Matsuhisa, Ushiku; Takeshi Murakami, Tsukuba; Shuichi Sakuda, Tokyo; Noriyuki Kawano; Kumiko Shibasaki, both of Tsukuba; Akihiro Tanaka, Tsuchiura, all of (JP)

(73) Assignee: Yamanouchi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/380,683

(22) PCT Filed: Mar. 5, 1998

(86) PCT No.: PCT/JP98/00916

§ 371 Date: Sep. 2, 1999

§ 102(e) Date: Sep. 2, 1999

(87) PCT Pub. No.: WO98/39325

PCT Pub. Date: Sep. 11, 1998

(30) Foreign Application Priority Data

Mar. 6, 1997 (JP) .............................................. 9-052163

(51) Int. Cl.[7] .......................... A61K 31/55; A61P 15/00; C07D 223/16
(52) U.S. Cl. .................................. 514/213.01; 540/593
(58) Field of Search ....................... 540/593; 514/213.01

(56) References Cited

U.S. PATENT DOCUMENTS

| 5,498,609 A | 3/1996 | Ogawa et al. ............... 514/213 |
| 5,677,299 A | 10/1997 | Ogawa et al. ............... 514/221 |

FOREIGN PATENT DOCUMENTS

| WO | WO 94/01113 | 1/1994 |
| WO | WO 95/34540 | 12/1995 |

OTHER PUBLICATIONS

Ogawa H. et al., JP 6–211800 (Otsuka Pharmaceutical Co., Ltd.), Aug. 2, 1994, (Abstract Only).

*Primary Examiner*—Brenda Coleman
(74) *Attorney, Agent, or Firm*—Finnegan, Henderson, Farabow, Garrett & Dunner, LLP

(57) ABSTRACT

4,4-difluoro-2,3,4,5-tetrahydro-1H-1-benzoazepine compounds or salts thereof and pharmaceutical compositions containing 4,4-difluoro-2,3,4,5-tetrahydro-1H-1-benzoazepine compounds, or salts thereof, and a pharmaceutically acceptable carrier. The chemical structure of these compounds is characterized by a difluoro group on a ring carbon atom adjacent to an azepine ring carbon atom substituted with a methylidene group. Pharmaceutical compositions containing these compounds are particularly useful as oxytocin antagonists and are effective in inhibiting threatened premature birth or abortion and precesarean birth, and are effective as a remedy for dysmenorrhea and other such conditions.

6 Claims, No Drawings

4,4-DIFLUORO-2,3,4,5-TETRAHYDRO-1H-1-BENZOAZEPINE DERIVATIVES AND DRUG COMPOSITIONS CONTAINING THEM

This application is national stage entry under 35 U.S.C. §371 of PCT/JP98/00916, filed Mar. 5, 1998.

FIELD OF THE INVENTION

The present invention relates to pharmaceuticals and, more particularly, it relates to 4,4-difluoro-2,3,4,5-tetrahydro-1H-1-benzoazepine derivatives or salts thereof and also to a drug composition containing the same and a pharmaceutically acceptable carrier.

BACKGROUND OF THE INVENTION

Oxytocin is a peptide hormone which is mainly synthesized in hypothalamus and is secreted after an axonal transport in nerve cells to posterior pituitarity. It has been known already that an extract from posterior pituitarity has an activity of uterus contraction and of milk secretion, and two years after the elucidation of its amino acid structure in 1953, clinical application of synthetic oxytoxin started. As such, clinical application firstly proceeded for oxytocin, and it was used as a drug for controlling labor pains while analysis of physiological mechanism of oxytocin has not made so much progress. As the reasons therefor, it can be considered that since oxytocin is a small amino acid peptide, measurement of its concentration in blood was difficult, blood and tissues contain large amounts of oxytocin decomposition enzymes and that analysis of oxytocin receptor was difficult (cf. *Sanka to Fujinka*, 10: 59–65, 1995).

It has been recently clarified that besides the above-mentioned two classic physiological actions, oxytocin has various physiological actions in addition to the area of delivery such as central action for maternal behavior and for memory, action to functional regulation of sexual glands, action as a neurotransmitter, and action in immune system (*Kusuri no Kaisetsu*, Vol. 30, No. 10: 1164–1167, 1994). Oxytocin receptor was cloned, too (Kimura, T. et al., *Nature*, 356: 526–529, 1992), and it is now possible to investigate the expression of the receptor in terms of molecular biology. It has been known that oxytocin receptor is mostly expressed in uterine muscle and endometrium in the cases of labor pain onset in term delivery.

Since the above-mentioned expression of oxytocin receptor in uterine muscle and endometrium increases in the cases of early delivery, the effect as a suppressor for uterine contraction at early delivery can be expected, and accordingly, investigation for oxytocin antagonist has started. As a drug which is the first runner in the clinical application, atosiban which is a peptidal oxytocin antagonist is available at present, and there is a report on the cases where it significantly lowers the frequency of uterine contraction without changes in heart rate and blood pressure during that time (Goodwin, T. M. et al., *Am. J. Obstet. Gynecol.*, 170: 474–478, 1994). It has been ascertained that atosiban has an antagonistic action not only to oxytocin receptor but also to vasopressin $V_1$ receptor.

Incidentally, oxytocin antagonists are mentioned in European Patent No. 450,761A and in Unexamined Published Japanese Patent Application No. 5-213,865. In addition, benzoheterocyclic derivatives represented by the following formula are mentioned in WO95/34540, and with respect to their vasopressin-acting/antagonizing action, specific pharmacological test methods, and the test results are mentioned therein. However, so far as an oxytocin-antagonizing action of these compounds is concerned, it is mentioned quite briefly only in one line, and any specific pharmacological test method and test results thereof are not disclosed at all:

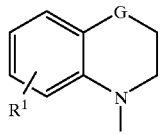

(In the above formula, G is 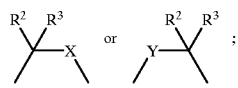

$R^2$ is a hydrogen atom, ... (omitted) ...; $R^3$ is a hydrogen atom, ... (omitted) ...; or $R^2$ and $R^3$ are taken together to form an oxo group, a lower alkylidene group, a lower alkoxy-substituted lower alkylidene group, a lower alkoxycarbonyl-substituted lower alkylidene group, or a phenyl-substituted lower alkylidene group; X is a methylene group, a simple linkage, or a group represented by the formula, =CH— or $NR^{14}$; and for others, refer to the above-cited patent specifications.)

DISCLOSURE OF THE INVENTION

We, the present inventors conducted intensive studies for finding compounds having an antagonistic action to oxytocin. As a result, it has been found that novel 4,4-difluoro-2,3,4,5-tetrahydro-1H-1-benzoazepine derivatives have a strong oxytoxin-antagonizing action, whereupon the present invention has been achieved.

Thus, the present invention relates to 4,4-difluoro-2,3,4,5-tetrahydro-1H-1-benzoazepine derivatives or salts thereof having oxytoxin antagonism, as represented by the following formula (I). The present invention also relates to a drug composition, particularly an oxytocin antagonist, containing the 4,4-difluoro-2,3,4,5-tetrahydro-1H-1-benzoazepine derivative or its salt and a drug acceptable carrier:

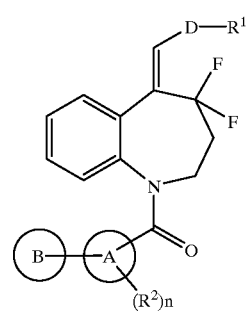

(I)

(In the formula, each of the symbols has the following meaning:

ring A: a 5-membered heteroarylene group;
ring B: an optionally substituted aryl group or a 5- to 6-membered heteroaryl group;
D: a carbonyl group or a lower alkylene group;
$R^1$: a group represented by formula, $NR^3R^4$, an —O-lower alkyl group, or OH;
$R^2$: an optionally halogen atom-substituted lower alkyl group, an —O-lower alkyl group, an —S-lower alkyl group, or a —CO-lower alkyl group;
$R^3$, $R^4$: same or different and each is 1) a hydrogen atom,
2) a lower alkyl group (the lower alkyl group may be substituted with OH, an optionally protected amino group, an optionally protected mono-lower alkylamino group, a di-lower alkylamino group, an optionally lower alkyl group-substituted 5- to 7-membered saturated heterocyclic group, a 5- to 6-membered heteroaryl group, or an aryl group),
3) a cycloalkyl group,
4) an optionally lower alkyl group-substituted 5- to 7-membered saturated heterocyclic group,
5) a 5- to 6-membered heteroaryl group,
6) an aryl group, or
7) an optionally substituted 5- to 7-membered nitrogen-containing heterocyclic group formed by integration of the formula, $NR^3R^4$ (the 5- to 7-membered nitrogen-containing heterocyclic group may be fused with a benzene ring or with a 5- to 6-membered heteroaryl group); (in the 5- to 7-membered saturated heterocyclic group, the 5- to 7-membered nitrogen-containing heterocyclic group and the 5- to 6-membered heteroaryl group in the above 2), 4), 5) and 7), a group having a cyclic secondary amine may be one wherein the amine is protected); and n: 0, 1 or 2).

The compounds of the present invention are characterized by having a chemical structure in which a difluoro group is present on a ring carbon atom adjacent to an azepine ring carbon atom substituted with a (substituted) methylidene group. Since the compounds of the present invention have a difluoro group, they are not isomerized but have good stability even in vivo.

Preferred compounds of the present invention are those in which $R^1$ is a group represented by the formula, $NR^3R^4$ wherein $R^3$ and $R^4$ are an optionally lower alkyl-substituted 5- to 7-membered saturated heterocyclic group or a 5- to 6-membered heteroaryl group, or the formula, $NR^3R^4$ may be integrated to form an optionally substituted 5- to 7-membered nitrogen-containing heterocyclic group. More preferred compounds are those in which $R^2$ is an optionally halogen atom-substituted lower alkyl group.

The compounds (I) of the present invention will be further illustrated below. Unless otherwise mentioned in the definitions for the formula in this specification, the term "lower" means a carbon chain, either straight or branched, having from 1 to 6 carbon atoms. The "lower alkylene group" stands for an alkylene group having one to six carbon atoms, and its preferred examples are a methylene group, an ethylene group, a propylene group, a butylene group, etc.

The "5-membered heteroarylene group" is a cyclic group where two linkages are available from a 5-membered monocyclic heteroaryl group, and specific examples thereof are furandiyl, thiophendiyl, pyrroldiyl, imidazoldiyl, thiazoldiyl, oxazoldiyl, pyrazoldiyl, isothiazoldiyl, isoxazoldiyl, oxadiazoldiyl, thiadiazoldiyl, triazoldiyl, tetrazoldiyl, etc. Preferred are furandiyl, thiophendiyl, imidazoldiyl, thiazoldiyl, oxazoldiyl, pyrazoldiyl, isoxazoldiyl, and triazoldiyl, with thiazoldiyl, imidazoldiyl, and pyrazoldiyl being particularly preferred.

With regard to the "cycloalkyl group", those having 3 to 8 carbon atoms are preferred, and specific examples thereof are cyclopropyl, cyclobutyl, cyclopentyl, cyclohexyl, cycloheptyl, cyclooctyl, etc.

With respect to the "aryl group", those having 6 to 14 carbon atoms are preferred, and specific examples thereof are phenyl, tolyl, xylyl, biphenyl, naphthyl, indenyl, anthryl, phenanthryl, etc. Preferred are phenyl and naphthyl, with phenyl being particularly preferred.

Examples of the substituent in the "optionally substituted aryl group" are a halogen atom, an optionally halogen atom-substituted lower alkyl, OH, a lower alkoxy, a lower alkanoyl, nitro, cyano, and amino, etc.

With respect to the "5- to 6-membered heteroaryl group", its specific examples are 5-membered heteroaryls such as furyl, thienyl, pyrrolyl, imidazolyl, thiazolyl, oxazolyl, pyrazolyl, isothiazolyl, isoxazolyl, oxadiazolyl, thiadiazolyl, triazolyl, tetrazolyl, etc.; 6-membered heteroaryls such as pyridyl, pyrimidyl, pyridazinyl, pyrazyl, triazyl, etc.; and the like.

With respect to the "lower alkyl group", its specific examples are methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, etc. Preferred are alkyls having 1 to 4 carbon atoms, with methyl, ethyl, propyl, and isopropyl being particularly preferred.

The "halogen atom" means a fluorine atom, a chlorine atom, bromine atom, or an iodine atom.

The "optionally halogen atom-substituted lower alkyl group" means an unsubstituted lower alkyl group or a group wherein one or more hydrogen atoms of a lower alkyl group are substituted with a halogen atom. Specific examples of the halogen atom-substituted lower alkyl group are fluoromethyl, chloromethyl, bromomethyl, iodomethyl, 1-chloroethyl, 2-chloroethyl, dichloromethyl, trifluoromethyl, dichlorobromomethyl, etc. Preferred is trifluoromethyl.

With respect to the "5- to 7-membered saturated heterocyclic group", its specific examples are pyrrolidinyl, imidazolidinyl, pyrazolidinyl, piperidinyl, piperazinyl, morpholyl, thiomorpholyl, tetrahydrofuranyl, tetrahydropyranyl, tetrahydrothienyl, oxathiolanyl, azepanyl, diazepanyl, etc. Preferred are pyrrolidinyl, piperidinyl, piperazinyl, morpholinyl, and diazepanyl.

The expression of the "5- to 7-membered nitrogen-containing heterocyclic group may be fused with a benzene ring or with a 5- to 6-membered heteroaryl group" means "a 5- to 7-membered nitrogen-containing heterocyclic group" or "a 5- to 7-membered nitrogen-containing heterocyclic group which is fused with a benzene ring or with a 5- to 6-membered heteroaryl group", and specific examples of the "5- to 7-membered nitrogen-containing heterocyclic group" are pyrrolidinyl, imidazolidinyl, pyrazolidinyl, piperidyl, piperazinyl, azepanyl, morpholyl, thiomorpholyl, diazepanyl, etc. Preferred are piperidyl, piperazinyl, morpholyl, thiomorpholyl, and diazepanyl.

Specific examples of the "5- to 7-membered nitrogen-containing heterocyclic group which is fused with a benzene ring or with a 5- to 6-membered heteroaryl group" are a nitrogen-containing saturated ring fused with a benzene ring, such as indolinyl, benzimidazolidinyl, benzopyrazodinyl, benzopiperidyl, benzopiperazinyl, benzazepinyl, etc.; a nitrogen-containing heterocyclic group fused with a 5- to 6-membered heteroaryl group, such as tetrahydronaphthylidinyl, tetrahydropyridoazepinyl, tetrahydroimidazopyridyl, tetrahydroimidazopyrimidyl, etc.; and the like. Preferred are tetrahydronaphthylidinyl, tetrahydropyridoazepinyl, and tetrahydroimidazopyridyl.

Examples of the substituent in the "optionally substituted 5- to 7-membered nitrogen-containing heterocyclic group formed by integration of NR³R⁴" are (1) oxo, (2) OH, (3) a lower alkylidene (the lower alkylidene may be substituted with carbamoyl, carboxyl, or a lower alkoxycarbonyl), (4) a lower alkoxy (the lower alkoxy may be substituted with a lower alkoxycarbonyl or carboxyl), (5) carboxyl, (6) a lower alkoxycarbonyl, (7) carbamoyl (the carbamoyl group may be substituted with a lower alkyl which may be substituted with a lower alkoxycarbonyl or carboxyl, or a lower alkoxy), (8) a lower alkanoyl (the lower alkanoyl may be substituted with a lower alkoxycarbonyl or carboxyl), (9) amino (the amino may be substituted with or protected by a lower alkyl which may be substituted with a lower alkoxycarbonyl, a lower carbamoyl or carboxyl, or a lower alkanoyl which may be substituted with a lower alkoxycarbonyl or carboxyl), (10) imino (the imino may be substituted with OH, an optionally substituted lower alkoxy, a lower alkanoyloxy, or a lower alkanoyloxy which may be substituted with an optionally lower alkyl-substituted amino; and examples of the substituent in the optionally substituted lower alkoxy are a lower alkoxycarbonyl, carboxyl, a lower carbamoyl which may be substituted with an optionally lower alkoxy-substituted aminoalkyl, a saturated heterocycle, an optionally protected heteroaryl, etc.), (11) an optionally lower alkyl-substituted aryl, (12) a heteroaryl, (13) morpholyl, (14) a cycloalkyl, (15) an optionally lower alkanoyl-substituted hydrazone, (16) an optionally substituted hydrazino, (17) a lower alkenyl which may be substituted with a lower alkoxycarbonyl or carboxyl, (18) a lower alkyl (the lower alkyl may be substituted with OH, an optionally OH-substituted lower alkoxy (the lower alkoxy may be substituted with a lower alkoxycarbonyl or carboxyl), carboxyl, a lower alkoxycarbonyl, carbamoyl (the carbamoyl may be substituted with an optionally substituted lower alkyl; and examples of the substituent in the optionally substituted alkyl are a lower alkoxycarbonyl, carboxyl, an optionally lower alkyl-substituted amino, etc.), cyano, amino (the amino may be substituted with or protected by a lower alkyl), morpholyl, a lower alkanoyloxy, an optionally OH-substituted imino, or an optionally substituted or protected heteroaryl), etc. Preferred are (1) OH, (2) carbamoyl, (3) carboxyl, (4) amino (the amino may be substituted with a lower alkyl or a lower alkanoyl), (5) oxo, (6) imino (the imino may be substituted with OH, a lower alkoxy, a lower alkanoyloxy, or an optionally carboxyl-substituted lower alkoxy), (7) an optionally lower alkoxycarbonyl-substituted lower alkanoyl, (8) an optionally carboxyl-substituted lower alkoxy, (9) an optionally carboxyl-substituted lower alkenyl, (10) an optionally lower alkanoyl-substituted hydrazone, and (11) a lower alkyl (the lower alkyl group which may be substituted with OH, a lower alkoxy, a lower alkoxycarbonyl, amino (the amino may be substituted with a lower alkyl), carboxyl or carbamoyl).

The protective group for the "optionally protected amino group" or the "optionally protected mono-lower alkylamino group" and the protective group in an expression of "in a group having a cyclic secondary amine, the amine may be protected" each means a protective group for the amino group which is usually used by those persons skilled in the art, and representative examples thereof are acyls such as formyl, acetyl, trifluoroacetyl, propionyl, methoxyacetyl, meth-oxypropionyl, benzoyl, thienylacetyl, thiazolylacetyl, tetrazolylacetyl, thiazolylglyoxyloyl, thienylglyoxyloyl, etc.; lower alkoxycarbonyls such as methoxycarbonyl, ethoxycarbonyl, tert-butoxycarbonyl, etc.; aralkyloxy-carbonyls such as benzyloxycarbonyl, p-nitrobenzyloxycarbonyl, etc.; lower alkanesulfonyls such as methanesulfonyl, ethanesulfonyl, etc.; aralkyls such as tosyl, benzyl, p-nitrobenzyl, benzhydryl, trityl, etc.; tri-lower alkylsilyls such as trimethylsilyl, etc.; and the like.

The compound of the present invention can form a salt, and examples of the acid addition salt are those with inorganic acids such as hydrochloric acid, hydrobromic acid, hydroiodic acid, sulfuric acid, nitric acid, phosphoric acid, etc.; those with organic acids such as formic acid, acetic acid, propionic acid, butyric acid, isobutyric acid, valeric acid, isovaleric acid, pivalic acid, oxalic acid, malonic acid, succinic acid, fumaric acid, maleic acid, lactic acid, citric acid, malic acid, tartaric acid, carbonic acid, methane-sulfonic acid, ethanesulfonic acid, glutamic acid, aspartic acid, etc.; and the like. Examples of the base addition salt are salts with inorganic bases of sodium, potassium, magnesium, calcium, aluminum, etc., organic bases such as methylamine, ethylamine, ethanolamine, ammonia, etc.; bases of basic amino acids such as lysine, ornithine, etc.; and the like.

In the compound of the present invention, there are tautomers due to conjugated double bonds, and with regard to a substituted methylidene group bound to a benzazepine ring, a (Z)-isomer is preferred. Depending upon the type of the substituent of the compound of the present invention, optical isomers due to the presence of asymmetric carbon atoms, or isomers due to the presence of a hydroxyimino group, a lower alkoxyimino group, or a lower alkanoyloxy-imino group, can be present. The present invention includes all of these isomers in a form of both separated and mixed ones.

Depending upon the physicochemical properties or manufacturing conditions, the compound of the present invention can be isolated as a hydrate, as a solvate with ethanol, etc. or as a substance having various crystalline forms giving crystalline polymorphism, and the present invention includes all of these hydrates, solvates with ethanol, etc. and substances in various crystalline forms.

(Manufacturing Methods)

The compound (I) of the present invention can be manufactured by applying various synthetic methods utilizing the characteristics due to its fundamental skeleton or to the type of the substituent. Representative manufacturing methods are given hereunder.

Incidentally, it is also possible in the synthesis that the functional group of the starting material or of the compound of the present invention is provided for a reaction after protecting with a suitable protective group. Examples of such a protecting group are those which are mentioned, for example, in Greene and Wuts, "Protective Groups in Organic Synthesis" (second edition), and they can be appropriately used depending upon the reaction conditions. In the case of an aldehyde, it can be reacted as an acetal, followed by returning to an aldehyde group.

First Manufacturing Method

First Step:

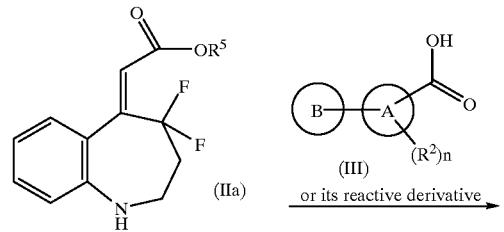

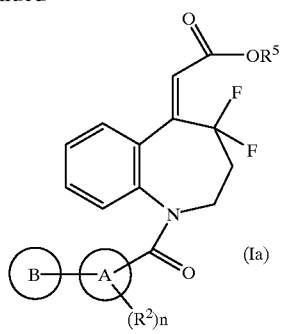

(Ia)

↓ hydrolysis

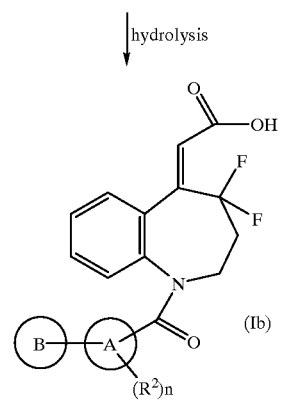

(Ib)

(In the formulae, ring A, ring B, $R^2$ and n have the same meanings as defined before; and $R^5$ is a protective group for hydroxyl group.)

This manufacturing method is a method wherein a benzoazepine compound of formula (IIa) is reacted with a carboxylic acid of formula (III) or a reactive derivative thereof to conduct an amidation reaction, whereby a compound (Ia) of the present invention is synthesized, followed by hydrolyzing to give a compound (Ib) of the present invention.

Examples of the reactive derivative of the compound (III) are conventionally used usual esters such as methyl ester, ethyl ester, isobutyl ester, tert-butyl ester, etc. of carboxylic acid; acid halides such as acid chloride or acid bromide; acid azides; active esters which are obtained by the reaction with a phenolic compound such as 2,4-dinitrophenol, etc. or with an N-hydroxylamine-based compound such as 1-hydroxysuccinic acid imide, 1-hydroxybenzotriazole, etc.; symmetric acid anhydrides; mixed anhydrides such as organic acid-based mixed acid anhydrides which are obtained by the reaction with a halogenocarboxylic acid alkyl ester such as alkyl carbonate halides, etc. or with a pivaloyl halide, and phosphoric acid-based mixed acid anhydrides which are obtained by the reaction with diphenyl chloride phosphoryl or N-methylmorpholine; and the like.

When a carboxylic acid is reacted in a form of free acid or without isolation of the active ester, it is preferred to use a condensing agent such as dicyclohexylcarbodiimide (DCC), 1,1'-carbonyldimidazole (CDI), diphenyl phosphoryl azide (DPPA), diethyl phosphoryl cyanide, 1-ethyl-3-(3-dimethylaminopropyl)carbodiimide hydrochloride (WSC.HCl), etc.

In particular, in the present invention, an acid chloride method, a method where the reaction is conducted in the presence of an active esterifying agent and a condensing agent, and a method where a usual ester is subjected to a treatment with an amine are convenient since they give the compound of the present invention in an easy and simple manner.

The reaction is usually conducted in an organic solvent which is inert to the reaction, such as halogenated hydrocarbons such as dichloromethane, dichloroethane, chloroform, etc.; aromatic hydrocarbons such as benzene, toluene, xylene, etc.; ethers such as diethyl ether, tetrahydrofuran, etc.; esters such as ethyl acetate, etc.; N,N-dimethylformamide; dimethyl sulfoxide; etc. with cooling, with cooling to ambient temperature, or at ambient temperature to heating, depending upon the type of the reactive derivatives used, although such can vary depending upon the reactive derivative and condensing agent used for the reaction, etc.

In conducting the reaction, it is sometimes advantageous for proceeding the reaction smoothly to use the benzazepine compound (IIa) excessively or to conduct the reaction in the presence of a base such as N-methylmorpholine, trimethylamine, triethylamine, N,N-dimethylaniline, pyridine, 4-(N,N-dimethylamino)pyridine, picoline, lutidine, etc. Pyridine can be used as a solvent as well.

In the reaction where the compound (Ia) is hydrolyzed to synthesize the compound (Ib), the hydrolysis is conducted with cooling, with cooling to at ambient temperature, or at ambient temperature to heating, in the presence of a suitable catalyst such as acids or bases in the above-mentioned inert solvent or in a mixed solvent of water with an alcoholic solvent such as methanol, ethanol, etc.

The protective group $R^5$ for the hydroxyl group means a protective group for hydroxyl group which is usually used by those persons skilled in the art, and its representative examples are lower alkyl groups such as methyl group, ethyl group, propyl group, isopropyl group, tert-butyl group, etc.; lower alkyl groups where the arbitrary hydrogen atom or atoms of the above lower alkyl group are substituted with a lower alkoxy group; lower alkoxy-lower alkoxy-lower alkyl groups; aryl methyl groups such as benzyl group, etc.; acyl groups such as benzoyl group, a lower alkanoyl group; etc.; and the like.

Second Step:

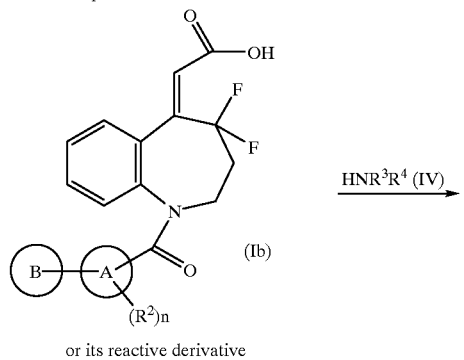

(Ib)

or its reactive derivative

HNR³R⁴ (IV)

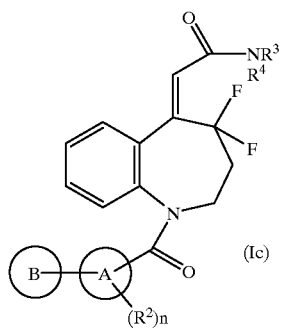

(Ic)

(In the formulae, ring A, ring B, $R^2$, $R^3$ and $R^4$ and n have the same meanings as defined already.)

This manufacturing method is a method for the manufacture of a compound (Ic) of the present invention by the reaction of the compound (Ib) with an amine of the formula (IV). The reaction conditions for this step are the same as those given for the amidation reaction shown in the first step of the first manufacturing method.

Second Manufacturing Method

First Step:

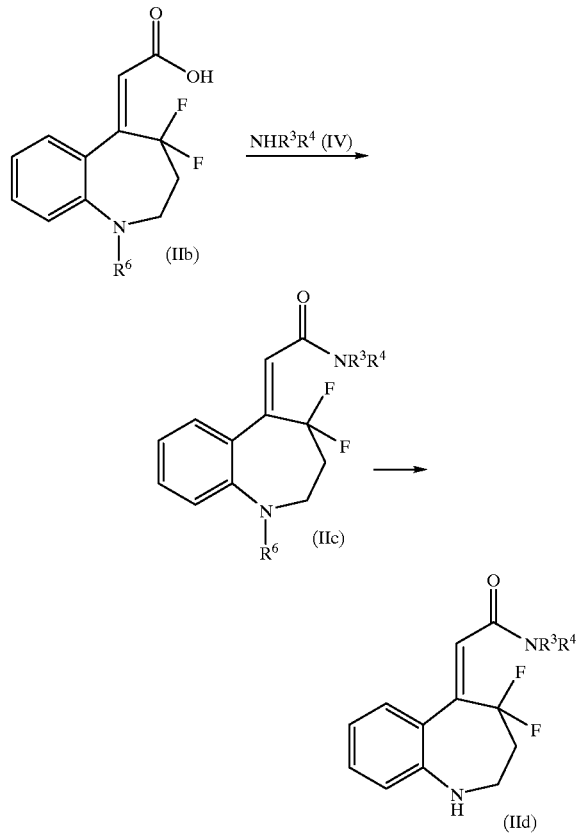

R$^6$: hydrogen atom or protective group

When R$^6$ is a protective group, removal of the protective group follows.

(In the formulae, R$^3$ and R$^4$ have the same meanings as defined already, and R$^6$ is a hydrogen atom or a protective group.)

This manufacturing method is a method where a compound (IIb) is reacted with an amine of the formula (IV) to give a compound (IIc). The reaction conditions for this step are the same as those mentioned for the amidation reaction given in the first step of the first manufacturing method.

In particular, in the present invention, a method where the reaction is conducted in the presence of both an active esterifying agent and a condensing agent, and a method where a usual ester is treated with an amine are simple and easy. When R$^6$ is a protective group, it can be subsequently removed by conventional means, if desired, to prepare (IId).

Second Step:

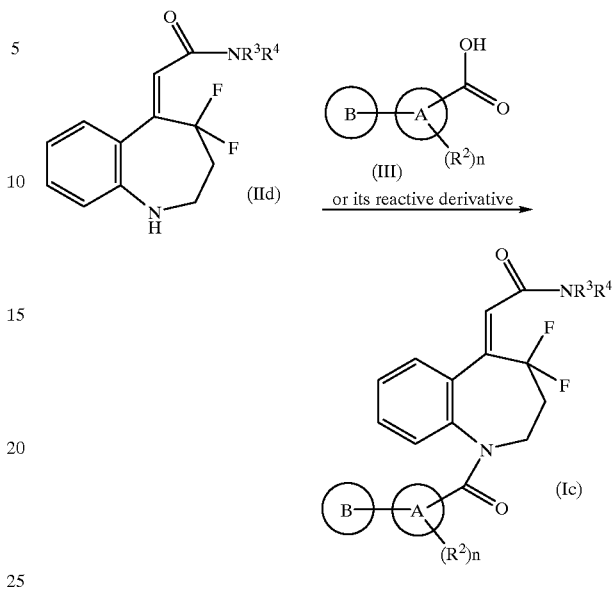

(In the formulae, ring A, ring B, R$^2$, R$^3$, R$^4$ and n have the same meanings as defined already.)

This manufacturing method is a method where a compound (IId) is reacted with a carboxylic acid of the formula (III) or a reactive derivative thereof to give the compound (Ic) of the present invention. The reaction conditions for this step are the same as those in the amidation reaction shown in the first step of the first manufacturing method.

An acid chloride method is particularly convenient and easy in the present invention.

Third Manufacturing Method

First Step:

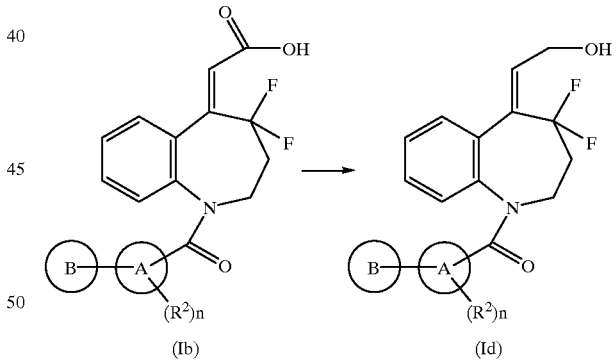

(In the formulae, ring A, ring B, R$^2$ and n have the same meanings as defined already.)

This manufacturing method is a method in which the compound (Ib) is esterified, followed by subjecting to reduction to give a compound (Id) of the present invention.

The esterification reaction is conducted using an N-hydroxyamine-based compound such as 1-hydroxysuccinimide, etc. in the presence of the condensing agent mentioned in the first step of the first manufacturing method while stirring in the above-mentioned inert solvent with cooling, with cooling to at room temperature, or at room temperature to heating (under refluxing).

The reduction reaction is conducted using a reducing agent (such as sodium borohydride, sodium cyanoborohydride, sodium triacetoxyborohydride, aluminum diisobutyl hydride, etc.) in an alcohol or in the above-mentioned inert solvent with cooling, with cooling to at room temperature, or at room temperature to heating (under refluxing).

Second Step:

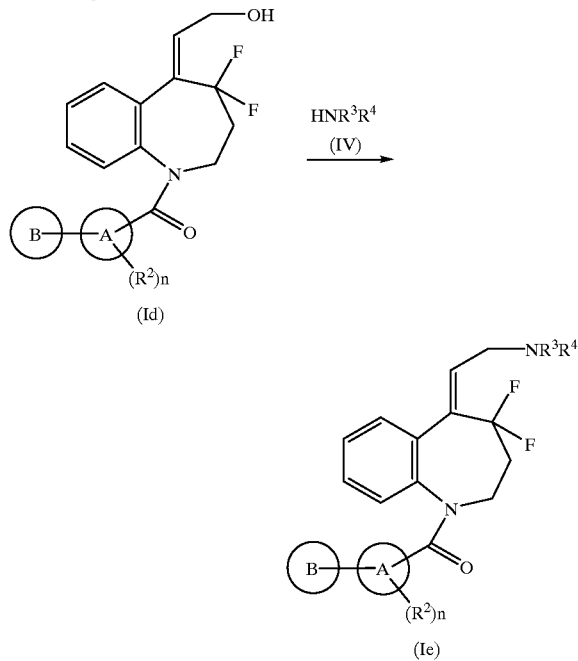

(In the formulae, ring A, ring B, $R^2$, $R^3$, $R^4$ and n have the same meanings as defined already.)

This manufacturing method is a method in which the compound (Id) is sulfonated, followed by subjecting to a reaction with the amine represented by the formula (IV) to give a compound (Ie) of the present invention.

The sulfonation reaction is conducted by a sulfonating reagent such as tosylic acid halides, methanesulfonic acid halides, etc. in the presence of the above-mentioned inert solvent with cooling, with cooling to at room temperature, or at room temperature to heating (with refluxing) with stirring. It is also possible to add a base (such as inorganic bases, e.g., potassium carbonate, sodium carbonate, etc., or organic bases, e.g., triethylamine, etc.) to promote the reaction.

The amination reaction is conducted in the above-mentioned inert solvent with cooling, with cooling to at room temperature, or at room temperature to heating (under refluxing) with stirring. It is also possible to add sodium iodide, potassium iodide, etc. to promote the reaction.

(Other Manufacturing Methods)

In addition to the above-mentioned methods, the compounds of the present invention can be manufactured by conversion of various substituents. For example, in the case of the compounds of formula, $NR^3R^4$, wherein $R^3$ and $R^4$ are an alkyl group-based substituent, or $R^3$ and $R^4$ are taken together to form an optionally substituted 5- to 7-membered nitrogen-containing hetero-cyclic group having a substituent at the nitrogen atom in the heterocyclic group, a conventional N-alkylating reaction by the reaction of the corresponding alkyl halide or alkyl sulfonate compound with the corresponding amine is conducted. Specifically, an alkyl halide or alkyl sulfonate compound and the amine in an amount corresponding to the reaction are stirred in the above-mentioned inert solvent with cooling, with cooling to at room temperature, or at room temperature to heating (under refluxing). It is also possible to add a base (such as inorganic bases, e.g., potassium carbonate, sodium carbonate, etc., and organic bases, e.g., triethylamine, etc.) to promote the reaction.

In the case of aromactic amino compounds, they can be manufactured by reducing the corresponding nitro compounds by conventional means. In the case of compounds substituted with a lower alkyl group, they can be manufactured by applying the conventional method mentioned for the above N-alkylation while, in the case of compounds having a saturated ring, they can be manufactured by applying the above N-alkylation using the corresponding dihalides.

Compounds having an amine structure at the end, they can be manufactured from the corresponding compounds having a hydroxyl group by an amination reaction mentioned in the above second step of the third manufacturing method. Compounds having a hydroxime or alkoxime structure at the end can be manufactured by conventional means, wherein the corresponding compound having a carbonyl group is condensed with hydroxylamine or with an alkoxylamine. Further, acyloxyimino compounds can be manufactured by subjecting the corresponding hydroxime compound to conventional acylation. In addition, the compounds having an acetylpiperidino group in $NR^3R^4$ can be manufactured from the corresponding N-methoxy-N-methyl-carbamoyl-substituted compound having a piperidino group.

In removing the protective group from the "optionally protected amino group" or the "optionally protected mono-lower alkylamino group" and the protective group from the case where "in a group having a cyclic secondary amine, the amine may be protected", the conventional methods mentioned in the above-mentioned references such as that by Greene, et al. can be used. Also, compounds having a hydrazone structure or an ether structure at the end can be manufactured by usual hydrazonation reaction or O-alkylation reaction.

The compound of the present invention manufactured as such can be isolated and purified as it is or as a salt thereof after subjecting to a salt formation process by conventional means. The isolation and purification can be conducted by applying usual chemical operations such as extraction, concentration, evaporation, crystallization, filtration, recrystallization, various chromatographic means, etc.

Each of the isomers can be isolated by usual methods utilizing the difference in physicochemical properties among the isomers. For example, in the case of racemic compounds, a sterically pure isomer can be prepared by means of usual racemic resolution [e.g., diastereomer salts with a usual optically active acid (such as tartaric acid, etc.) are prepared, followed by subjecting to optical resolution, etc.]. In the case of a mixture of diastereomers, they can be separated, for example, by means of fractional crystallization, chromatography, etc. It is also possible to manufacture an optically active compound starting from an appropriate optically active material.

Industrial Applicability 4,4-Difluoro-2,3,4,5-tetrahydro-1H-1-benzoazepine derivatives which are represented by the formula (I) and salts thereof according to the present invention have an antagonistic action to oxytocin and therefore, are useful as remedies for inhibiting threatened premature birth or abortion, or precesarean birth, dysmenorrhea, suppression of contraction of uterine smooth muscle, suppression of release of milk, etc. In addition, due to their nature as an oxytocin antagonist may be also applicable to endometriosis (*Adv.*

*Exp. Med. Biol.*, 395: 491–493, 1995), feeding control (*Neruosci. Biobehav. Rev.*, 15: 217–231, 1991), disturbance of memory (*Eur. J. Pharmacol.*, 94: 125–131, 1983; *J. Pharmacol. Exp. Ther.*, 241: 268–274, 1987), natriuresis (*J. Pharmacol. Exp. Ther.*, 246: 603–609, 1988), carbohydrate metanolism regulation (*Acta. Physiol. Scand.*, 144: 355–359, 1992), prostatic hypertrophy (*Adp. Exp. Med. Biol.*, 395: 529–538, 1995), breast cancer (*Endocrinology*, 137: 773–779, 1996), etc. Moreover, in view of the investigations at present, they also participate in the functions such as regulation of ovulatory and luteal functions in ovarium (*J. Reprod. Fert.*, 91: 49, 1991; *J. Reprod. Fert.*, 90: 625, 1990), regulation of sperm transportation (*Igaku Seirigaku Tenbo*, a book, 14th edition, 1990), regulation of sexual behavior (*J. Clin. Endocrinol. Metab.*, 64: 27, 1987; *Neurosci. Biobehav. Rev.*, 16: 131–144, 1992), regulation of maternal behavior (*Proc. Natl. Acad. Sci. USA*, 89: 5981, 1992), etc. Effects of the compounds of the present invention have been ascertained by the following tests.

(Oxytocin Receptor Binding Assay)

Preparation of Uterine membrane was prepared by a method of Soroff, et al. (*J. Biol. Chem.*, 249: 1376, 1974) while a binding assay was performed by a method of Pettibone, et al. (*Endocrinology*, 125: 217, 1989). Diethylstilbestrol dipropionate (0.3 mg/kg) was administered to a rat intraperitoneally, and after 18 to 24 hours, uterus was excised, and a membrane sample was prepared therefrom. [$^3$H]-Oxytocin (0.5 nM; specific activity=30 to 60 Ci/mmol), 50 μg of the membrane sample and a test drug ($10^{-8}$ to $10^{-5}$ M) were incubated at room temperature for 60 minutes in 250 μl (total volume) of 50 mM Tris hydrochloride buffer (pH 7.4) containing 10 mM of magnesium chloride and 0.1% of bovine serum albumin (BSA). After that, the incubated solution was sucked using a cell harvester and collected by filtration through a glass filter (GF/C) to remove a free ligand and an excessive buffer, and a labeled ligand bound to the receptor was trapped. The glass filter was taken out, well dried and mixed with a cocktail for liquid scintillation, the amount of [$^3$H]-oxytocin bound to the sample was determined by a liquid scintillation counter, and the inhibition rate was calculated from the following equation:

$$\text{Inhibition rate } (\%) = 100 - (C_1 - B_1/C_0 - B_1) \times 100$$

wherein
- $C_1$: The amount of [$^3$H]-oxytocin binding to the membrane sample when a known amount of the test drug and [$^3$H]-oxytocin coexisted and were treated with the membrane sample;
- $C_0$: The amount of [$^3$H]-oxytocin binding to the membrane sample when there was no test drug, but [$^3$H]-oxytocin and the membrane sample were treated with the membrane sample; and
- $B_1$: The amount of [$^3$H]-oxytocin binding to the membrane sample when excessive oxytocin ($10^{-6}$ M), [$^3$H]-oxytocin and the membrane sample were treated.

$IC_{50}$ was determined from the concentration of the test drug when the inhibition rate calculated above became 50%, and then the affinity of binding of the nonradioactive ligand, that is, a dissociation constant (Ki), was calculated by the following equation:

$$Ki = IC_{50}/(1 + [L]/Kd)$$

wherein [L] is a concentration of the radioactive ligand; and Kd is a dissociation constant calculated from the scattered plots.

Then, a negative logarithmic value of Ki calculated hereinabove was taken as pKi. Accordingly, the more the pKi, the stronger the bound to oxytocin receptor.

From the above-mentioned test, it was ascertained that the compounds of the present invention strongly bond to the oxytocin receptor. For example, the compound of Example 4-2 showed a binding activity of as strong as where pKi was 8.90 in the oxytocin receptor binding test. The compound of Example 4-7 showed a pKi of 8.87, and the compound of Example 10-1 showed a pKi of 8.68. Incidentally, the pKi value of atosiban was 7.93.

Further, some compounds of the present invention showed a binding activity to $V_1$ or $V_2$ receptor.

A drug composition containing one or more of the compounds of the present invention or salts thereof is prepared using a usual pharmaceutically acceptable carrier. Administration of the drug composition in accordance with the present invention can be in any of oral administration and parenteral administration by means of, e.g., injections, suppositories, percutaneous agents, inhalants, intravesical infusions, etc.

Dose can be appropriately decided for each case by taking symptom, age/sex of the patient, etc. into consideration, but usually, it is around 0.01 mg/kg to 100 mg/kg per day for adults in the case of oral administration, and it is administered at one time or divided into two to four times a day. When intravenous injection is conducted depending upon the symptom, 0.001 mg/kg to 100 mg/kg at a time for adults is usually administered once or more times a day. Examples of the carrier for the preparation are solid or liquid nontoxic substances for drugs.

With respect to the solid composition for oral administration in accordance with the present invention, tablets, pills, capsules, powder, granules, etc. can be used. In such solid compositions, one or more active substances are mixed with at least one inert diluent such as lactose, mannitol, glucose, hydroxypropyl cellulose, microcrystalline cellulose, starch, polyvinylpyrrolidone, agar, pectin, magnesium metasilicate aluminate and magnesium aluminate. The compositions can contain additives other than the inert diluent, such as lubricants, e.g., magnesium stearate, disintegrating agents, e.g., calcium cellulose glycolate, stabilizers, e.g., lactose, and auxiliary solubilizers, e.g., glutamic acid and aspartic acid, in accordance with a conventional means. Tablets or pills can be coated, if necessary, with sugar coat such as sucrose, gelatin, hydroxypropyl cellulose, hydroxypropylmethyl cellulose phthalate, etc., or with a film made of a substance which is soluble in gastric juice or intestinal juice.

Liquid compositions for oral administration include pharmaceutically acceptable emulsions, solutions, suspensions, syrups, elixiers, etc. and contain usually used inert diluents such as purified water and ethanol. In addition to the inert diluents, the compositions can further contain auxiliary agents such as moisturizers or suspending agents, sweeteners, tasting agents, aromatic agents, and antiseptics.

Injections for parenteral administration include sterile aqueous or nonaqueous solutions, suspensions and emulsions. Aqueous solutions and suspensions include, for example, distilled water for injection and physiological saline solution. Examples of nonaqueous solutions and suspensions are propylene glycol, polyethylene glycol, vegetable oils such as cacao butter, olive oil and sesame oil, alcohols such as ethanol, gum arabic, Polysolvate 80 (a trade name), etc. These compositions can further contain auxiliary agents such as isotonizing agents, antiseptics, moisturizers, emulsifiers, dispersing agents, stabilizers (e.g., lactose) and auxiliary solubilizers (e.g., glutamic acid and aspartic acid). These can be sterilized, for example, by filtration passing through a bacteria preserving filter, compounding with a bactericide or irradiation. These can also be used by manufacturing a sterile solid composition, followed by dissolving in sterile water or a sterile solvent for injection before use.

BEST MODE FOR CARRYING OUT THE INVENTION

The present invention is further illustrated by way of the following Examples. Compounds of the present invention are not limited to those which are mentioned in the following Examples only but they include all of the compounds represented by the above-mentioned formula (I) as well as salts, hydrates, geometric and optical isomers and crystalline polymorphism thereof. Furthermore, when the materials used in the present invention are novel, they are mentioned in the Referential Examples as hereunder.

Referential Example 1

(Table 1)

To 60 ml of a methanolic solution of 2.27 g of methyl (Z)-(4,4-difluoro-2,3,4,5-tetrahydro-1H-1-benzoazepin-5-ylidene)acetate was added 30 ml of a 1N aqueous solution of sodium hydroxide, and the mixture was stirred at room temperature for 18 hours. To the reaction solution was added 30 ml of 1N hydrochloric acid, and the solvent was evaporated therefrom. To the residue were added 30 ml of acetonitrile, 1.82 g of 1-hydroxybenzotriazole, 2.59 g of 1-ethyl-3-(3-dimethylaminopropyl)carbodiimide monohydrochloride and 1.76 g of 4-(2-aminoethyl)morpholine, and the mixture was stirred at room temperature for 18 hours. After evaporation of the solvent, ethyl acetate was added to the residue, and the mixture was washed with a saturated aqueous solution of sodium bicarbonate and a saturated aqueous solution of NaCl. This was dried over magnesium sulfate, and the solvent was evaporated therefrom. The residue was purified by silica gel column chromatography (eluting with ethyl acetate-methanol). The resulting residue was crystallized from diethyl ether to give 2.06 g of (Z)-(4,4-difluoro-2,3,4,5-tetrahydro-1H-1-benzoazepin-5-ylidene)-N-(2-morpholinoethyl)acetamide as a colorless powder.

Referential Example 2

(Table 1)

To a solution of 10 g of (Z)-(4,4-difluoro-1-tosyl-2,3,4,5-tetrahydro-1H-1-benzoazepin-5-ylidene)acetic acid in 100 ml of tetrahydrofuran were added 4.12 g of 1-hydroxybenzotriazole, 5.85 g of 1-ethyl-3-(3-dimethylaminopropyl)carbodiimide monohydrochloride and 3.36 ml of 1-methylpiperazine, followed by stirring for two hours at room temperature. After evaporation of the solvent, ethyl acetate was added to the residue, and the mixture was washed with a saturated aqueous solution of sodium bicarbonate and a saturated aqueous solution of NaCl. After drying over magnesium sulfate, the solvent was evaporated off. The resulting residue was collected by filtration to give 11.76 g of (Z)-4,4-difluoro-5-[2-(4-methylpiperazin-1-yl)-2-oxoethylidene]-1-tosyl-2,3,4,5-tetrahydro-1H-1-benzoazepine as a colorless amorphous solid.

Referential Example 3

(Table 1)

(Z)-4,4-Difluoro-5-[2-(4-methylpiperazin-1-yl)-2-oxoethylidene]-1-tosyl-2,3,4,5-tetrahydro-1H-1-benzoazepine (11.7 g) was dissolved in 20 ml of concentrated sulfuric acid, followed by stirring for 24 hours at room temperature. The reaction solution was poured over 700 ml of a 1N aqueous solution of sodium hydroxide and extracted with chloroform. The organic layer was washed with a saturated aqueous solution of NaCl, and after drying over magnesium sulfate, the solvent was evaporated off. The resulting residue was crystallized from diethyl ether to give 7.62 g of (Z)-4,4-difluoro-5-[2-(4-methylpiperazin-1-yl)-2-oxoethylidene]-2,3,4,5-tetrahydro-1H-1-benzoazepine as a colorless powder.

EXAMPLE 1

(Table 2)

A catalytic amount of N,N-dimethylformamide was added to a solution of 800 mg of 4-methyl-2-phenylthiazole-5-carboxylic acid in 30 ml of dichloromethane, and then 630 µl of oxalyl chloride was dropped thereinto with ice cooling. After stirring for 30 minutes with ice cooling and for an additional 30 minutes at room temperature, the solvent was evaporated off. The residue was dissolved in 25 ml of dichloromethane, and the solution was dropped into a solution of 760 mg of methyl (Z)-(4,4-difluoro-2,3,4,5-tetrahydro-1H-1-benzoazepin-5-ylidene)acetate and 500 µl of triethylamine in 40 ml of dichloromethane with ice cooling. After stirring the reaction solution at room temperature for 18 hours, it was washed with a saturated aqueous solution of sodium bicarbonate and a saturated aqueous solution of NaCl. After drying over magnesium sulfate, the solvent was evaporated off. The residue was purified by silica gel column chromatography (eluting with chloroform-hexane) to give 1,080 mg of methyl (Z)-[4,4-difluoro-1-(4-methyl-2-phenylthiazole-5-carbonyl)-2,3,4,5-tetrahydro-1H-1-benzoazepin-5-ylidene]acetate as a colorless amorphous solid.

Examples 1-1 to 1-3 were obtained in the same manner as in Example 1 (Table 2).

EXAMPLE 2

(Table 2)

A 1N aqueous solution of sodium hydroxide (5 ml) was added to a solution of 1,080 mg of methyl (Z)-[4,4-difluoro-1-(4-methyl-2-phenylthiazole-5-carbonyl)-2,3,4,5-tetrahydro-1H-1-benzoazepin-5-ylidene]acetate in 30 ml of methanol, followed by stirring at room temperature for 18 hours. After evaporating the reaction solution, 20 ml of water and 10 ml of 1N hydrochloric acid were added to the residue, and the resulting precipitate was collected by filtration and washed with water to give 1,000 mg of (Z)-[4,4-difluoro-1-(4-methyl-2-phenylthiazole-5-carbonyl)-2,3,4,5-tetrahydro-1H-1-benzoazepin-5-ylidene]acetic acid as a colorless powder.

Examples 2-1 to 2-3 were obtained in the same manner as in Example 2 (Table 2).

EXAMPLE 3

(Table 3)

To a solution of 8.26 g of (Z)-[4,4-difluoro-1-(4-methyl-2-phenylthiazole-5-carbonyl)-2,3,4,5-tetrahydro-1H-1-benzoazepin-5-ylidene]acetic acid in 150 ml of tetrahydrofuran were added 2.79 g of 1-hydroxybenzotriazole, 5.40 g of 1-ethyl-3-(3-dimethylaminopropyl)carbodiimide monohydrochloride and 3.18 g of 2-(piperazin-1-yl)ethanol, and the mixture was stirred at room temperature for 18 hours. A saturated aqueous solution of sodium bicarbonate was added to the reaction solution, the mixture was extracted with chloroform, and the solvent was evaporated from the extract. The residue was dissolved in 300 ml of 0.1N hydrochloric acid, washed with ethyl acetate, made alkaline with a 1N aqueous solution of sodium hydroxide, and extracted with chloroform. The organic layer was washed with a saturated aqueous solution of NaCl and dried over magnesium sulfate, and the solvent was evaporated off. The residue was crystallized from ethyl acetate, collected by filtration, and washed with ethyl acetate. The resulting crystals (9.0 g) were dissolved in 100 ml of chloroform, and 6 ml of a 4N HCl/ethyl acetate solution was added, followed by stirring at room temperature. The resulting crystals were collected by filtration and washed with chloroform. Those crude crystals (3.0 g of the above-obtained ones in 10.0 g) were recrystallized from a 90% aqueous ethanol solution to give 2.48 g of (Z)-2-(4-{[4,4-difluoro-1-(4-methyl-2-phenylthiazole-5-carbonyl)-2,3,4,5-tetrahydro-1H-1-benzoazepin-5-ylidene]acetyl}piperazin-1-yl)ethanol monohydrochloride as a colorless powder.

The compounds given in the following Examples and also the compounds of Examples 3-1 to 3-3, 3-5, 3-6, 3-8, 3-9, 3-12 and 3-14 to 3-91 were obtained in the same manner as in Example 3 (Table 3).

EXAMPLE 3-4

(Z)-4,4-Difluoro-1-(4-methyl-2-phenylthiazole-5-carbonyl)-5-[2-(4-methylpiperazin-1-yl)-2-oxoethylidene]-2,3,4,5-tetrahydro-1H-1-benzoazepine dihydrochloride

EXAMPLE 3-7

(Z)-2-(4-{[4,4-Difluoro-1-(4-methyl-2-phenylthiazole-5-carbonyl)-2,3,4,5-tetrahydro-1H-1-benzoazepin-5-ylidene]acetyl}piperazin-1-yl)ethanol dihydrochloride

EXAMPLE 3-10

(Z)-3-(4-{[4,4-Difluoro-1-(4-methyl-2-phenylthiazole-5-carbonyl)-2,3,4,5-tetrahydro-1H-1-benzoazepin-5-ylidene]acetyl}piperazin-1-yl)propan-1-ol dihydrochloride

EXAMPLE 3-11

(Z)-(4-{[4,4-Difluoro-1-(4-methyl-2-phenylthiazole-5-carbonyl)-2,3,4,5-tetrahydro-1H-1-benzoazepin-5-ylidene]acetyl}piperazin-1-yl)acetamide dihydrochloride

EXAMPLE 3-13

(Z)-3-(4-{[4,4-Difluoro-1-(4-methyl-2-phenylthiazole-5-carbonyl)-2,3,4,5-tetrahydro-1H-1-benzoazepin-5-ylidene]acetyl}piperazin-1-yl)propionamide dihydrochloride

EXAMPLE 4
(Table 4)

To a solution of 200 mg of (Z)-[4,4-difluoro-1-(1-phenyl-5-trifluoromethyl-1H-pyrazole-4-carbonyl)-2,3,4,5-tetrahydro-1H-1-benzoazepin-5-ylidene]acetic acid in 20 ml of tetrahydrofuran were added 90 mg of 1-hydroxybenzotriazole, 130 mg of 1-ethyl-3-(3-dimethylaminopropyl)carbodiimide monohydrochloride and 60 mg of 1-methylpiperazine, and the mixture was stirred at room temperature for 18 hours. A saturated aqueous solution of sodium bicarbonate was added to the reaction solution, followed by extracting with ethyl acetate. The organic layer was washed with a saturated aqueous solution of NaCl and dried over magnesium sulfate, followed by evaporating off the solvent. The residue was purified by silica gel column chromatography (eluting with chloroform-methanol). The resulting residue (190 mg) was dissolved in 5 ml of chloroform, and 0.5 ml of a 4N HCl/ethyl acetate solution was added thereto, followed by stirring at room temperature. The solvent was evaporated off, and the residue was crystallized from ethanol-diethyl ether to give 190 mg of (Z)-4,4-difluoro-5-[2-(4-methylpiperazin-1-yl)-2-oxoethylidene]-1-(1-phenyl-5-trifluoromethyl-1H-pyrazole-4-carbonyl)-2,3,4,5-tetrahydro-1H-1-benzoazepine monohydrochloride as a colorless powder.

The compounds given in the following Examples and also the compounds of Examples 4-7 and 4-8 were obtained in the same manner as in Example 4 (Table 4).

EXAMPLE 4-1

Ethyl (Z)-(1-{[4,4-Difluoro-1-(1-phenyl-5-trifluoromethyl-1H-pyrazole-4-carbonyl)-2,3,4,5-tetrahydro-1H-1-benzoazepin-5-ylidene]acetyl}-4-piperidyl)acetate

EXAMPLE 4-2

(Z)-2-(4-{[4,4-Difluoro-1-(1-phenyl-5-trifluoromethyl-1H-pyrazole-4-carbonyl)-2,3,4,5-tetrahydro-1H-1-benzoazepin-5-ylidene]acetyl}piperazin-1-yl)ethanol monohydrochloride

EXAMPLE 4-3

(Z)-(4-{[4,4-Difluoro-1-(1-phenyl-5-trifluoromethyl-1H-pyrazole-4-carbonyl)-2,3,4,5-tetrahydro-1H-1-benzoazepin-5-ylidene]acetyl}piperazin-1-yl)acetamide monohydrochloride

EXAMPLE 4-4

(Z)-3-(4-{[4,4-Difluoro-1-(1-phenyl-5-trifluoromethyl-1H-pyrazole-4-carbonyl)-2,3,4,5-tetrahydro-1H-1-benzoazepin-5-ylidene]acetyl}piperazin-1-yl)propan-1-ol monchydrochloride

EXAMPLE 4-5

(Z)-3-(4-{[4,4-Difluoro-1-(1-phenyl-5-trifluoromethyl-1H-pyrazole-4-carbonyl)-2,3,4,5-tetrahydro-1H-1-benzoazepin-5-ylidene]acetyl}piperazin-1-yl)propionamide monohydrochloride

EXAMPLE 4-6

(Z)-4,4-Difluoro-1-(5-methyl-1-phenyl-1H-pyrazole-4-carbonyl)-5-[2-(4-methylpiperazin-1-yl)-2-oxoethylidene]-2,3,4,5-tetrahydro-1H-1-benzoazepine monohydrochloride

EXAMPLE 5
(Table 5)

To a solution of 150 mg of ethyl (Z)-(1-{[4,4-difluoro-1-(4-methyl-2-phenylthiazole-5-carbonyl)-2,3,4,5-tetrahydro-1H-1-benzoazepin-5-ylidene]acetyl}-4-piperidyl)acetate in 5 ml of ethanol was added 1 ml of a 1N aqueous solution of sodium hydroxide, followed by stirring at room temperature for 18 hours. After evaporating off the reaction solution, 1 ml of 1N hydrochloric acid was added to the residue, and the resulting precipitate was collected by filtration and washed with water to give 120 mg of (Z)-(1-{[4,4-difluoro-1-(4-methyl-2-phenylthiazole-5-carbonyl)-2,3,4,5-tetrahydro-1H-1-benzoazepin-5-ylidene]acetyl}-4-piperidyl)acetic acid as a colorless powder.

The compounds given in the following Examples (Tables 5 and 4) and also the compounds of Examples 5-1, 5-2 and 5-4 to 5-24 were obtained in the same manner as in Example 5 (Table 5).

EXAMPLE 5-3
(Table 5)

(Z)-3-(1-{[4,4-Difluoro-1-(4-methyl-2-phenylthiazole-5-carbonyl)-2,3,4,5-tetrahydro-1H-1-benzoazepin-5-ylidene]acetyl}-4-piperidyl)propionic acid

EXAMPLE 5-25
(Table 4)

(Z)-(1-{[4,4-Difluoro-1-(1-phenyl-5-trifluoromethyl-1H-pyrazole-4-carbonyl)-2,3,4,5-tetrahydro-1H-1-benzoazepin-5-ylidene]acetyl}-4-piperidyl)acetic acid

EXAMPLE 6
(Table 8)

To a solution of 250 mg of 2-phenylthiazole-4-carboxylic acid in 15 ml of dichloromethane was added a catalytic amount of N,N-dimethylformaide, and then 175 μl of oxalyl chloride was dropped thereinto with ice cooling. The mixture was stirred for one hour with ice cooling and for 30 minutes at room temperature, and the solvent was evaporated therefrom. The residue was dissolved in 10 ml of acetonitrile, and the solution was dropped, with ice cooling, into a solution of 250 mg of methyl (Z)-(4,4-difluoro-2,3,4,5-tetrahydro-1H-1-benzoazepin-5-ylidene)acetate and 170 μl of triethylamine in 15 ml of acetonitrile. The reaction solution was stirred for two hours at room temperature and for three hours at 50° C., and 100 ml of a saturated aqueous solution of sodium bicarbonate was added. This was extracted with ethyl acetate, followed by washing with a saturated aqueous solution of NaCl. After drying over magnesium sulfate, the solvent was evaporated therefrom. The oily residue (500 mg) was dissolved in 10 ml of methanol, 3 ml of a 1N aqueous solution of sodium hydroxide was added, and the mixture was stirred at room temperature for 18 hours. After subjecting the reaction solution to evaporation, water was added to the residue, and the mixture was washed with ethyl acetate. The aqueous solution was acidified with 10 ml of 1N hydrochloric acid, extracted with ethyl acetate and washed with a saturated aqueous solution of NaCl. After drying over magnesium sulfate, the solvent was evaporated therefrom. The residue (400 mg) was dissolved in 10 ml of tetrahydrofuran, then 210 mg of 1-hydroxybenzotriazole, 280 mg of 1-ethyl-3-(3-dimethylaminopropyl)carbodiimide monohydrochloride and 210 μl of 4-(2-aminoethyl)morpholine were added thereto, and the mixture was stirred at room temperature for 18 hours. To the reaction solution was added 50 ml of a saturated aqueous solution of sodium bicarbonate, and the mixture was extracted with ethyl acetate. The organic layer was washed with a saturated aqueous solution of NaCl and dried over magnesium sulfate, and the solvent was evaporated therefrom. The residue was purified by silica gel column chromatography (eluting with ethyl acetate-methanol) and crystallized from ethanol to give 90 mg of (Z)-[4,4-difluoro-1-(2-phenylthiazole-4-carbonyl]-2,3,4,5-tetrahydro-1H-1-benzoazepin-5-ylidene]-N-(2-morpholinoethyl)acetamide as a colorless powder.

EXAMPLE 7
(Table 6)

A catalytic amount of N,N-dimethylformamide was added to a solution of 180 mg of 5-ethyl-1-phenyl-1H-pyrazole-4-carboxylic acid in 10 ml of dichloromethane, and then 150 μl of oxalyl chloride was dropped thereinto with ice cooling. The mixture was stirred for 30 minutes while elevating the temperature to room temperature, followed by evaporating off the solvent. The residue was dissolved in 10 ml of dichloromethane and dropped into a solution of 180 mg of (Z)-4,4-difluoro-5-[2-(4-methylpiperazin-1-yl)-2-oxoethylidene]-2,3,4,5-tetrahydro-1H-1-benzoazepine in 10 ml of dichloromethane. The reaction solution was stirred at room temperature for three days, and a saturated aqueous solution of sodium bicarbonate was added and extracted with chloroform. The organic layer was washed with a saturated aqueous solution of NaCl and dried over magnesium sulfate, followed by evaporating off the solvent. The residue was purified by silica gel column chromatography (eluting with chloroform-methanol). The resulting residue (200 mg) was dissolved in 2 ml of ethyl acetate, and 0.3 ml of a 4N HCl/ethyl acetate solution was added, followed by stirring at room temperature. The solvent was evaporated off, and the residue was crystallized from diethyl ether to give 150 mg of (Z)-4,4-difluoro-1-(5-ethyl-1-phenyl-1H-pyrazole-4-carbonyl)-5-[2-(4-methylpiperazin-1-yl)-2-oxoethylidene]-2,3,4,5-tetrahydro-1H-1-benzoazepine monohydrochloride as a colorless powder.

The compound given in the following Example (Table 6) and also the compounds of Examples 7-1 and 7-3 to 7-12 (Table 6), 7-13 to 7-29 (Table 7), 7-30 to 7-48 (Table 8), and 7-49 and 7-50 (Table 9) were obtained in the same manner as in Example 7.

EXAMPLE 7-2

(Z)-4,4-Difluoro-5-[2-(4-methylpiperazin-1-yl)-2-oxoethylidene]-1-(1-phenyl-5-trifluoromethyl-1H-imidazole-4-carbonyl)-2,3,4,5-tetrahydro-1H-1-benzoazepine monohydrochloride.

EXAMPLE 8
(Table 10)

To a solution of 1.19 g of (Z)-2-[4,4-difluoro-1-(4-methyl-2-phenylthiazole-5-carbonyl)-2,3,4,5-tetrahydro-1H-1-benzoazepin-5-ylidene]acetic acid in 100 ml of dichloromethane were added 623 mg of 1-ethyl-3-(3-dimethylaminopropyl)carbodiimide monohydrochloride and 374 mg of N-hydroxysuccinimide, and the mixture was stirred at room temperature for 14 hours. The reaction solution was washed with water and dried over anhydrous magnesium sulfate. The residue obtained by evaporation of the solvent was dissolved in 40 ml of tetrahydrofuran, and 112 mg of sodium borohydride was added with ice cooling, followed by stirring at 0° C. for 24 hours. To the reaction solution were added ethyl acetate and 0.5N hydrochloric acid to undergo liquid separation, the organic layer was washed with a saturated aqueous solution of sodium bicarbonate and a saturated aqueous solution of NaCl, followed by drying over anhydrous magnesium sulfate. The residue obtained by evaporation of the solvent was purified by silica gel column chromatography (eluting with ethyl acetate-n-hexane) to give 230 mg of (Z)-2-[4,4-difluoro-1-(4-methyl-2-phenylthiazole-5-carbonyl)-2,3,4,5-tetrahydro-1H-1-benzoazepin-5-ylidene]ethanol as a colorless amorphous solid.

EXAMPLE 9
(Table 10)

To a solution of 150 mg of (Z)-2-[4,4-difluoro-1-(4-methylthiazole-5-carbonyl)-2,3,4,5-tetrahydro-1H-1-benzoazepin-5-ylidene]ethanol in 15 ml of dichloromethane were added 100 μl of triethylamine and 30 μl of methanesulfonyl chloride with ice cooling, and the mixture was stirred at room temperature for 20 minutes. To the reaction solution was added 50 ml of toluene, and the mixture was washed with a saturated aqueous solution of sodium bicarbonate and a saturated aqueous solution of NaCl, followed by drying over anhydrous magnesium sulfate. The residue obtained by evaporating the solvent was dissolved in 10 ml of N,N-dimethylformamide, and 390 μl of 1-methylpiperazine was added, followed by stirring at 80° C. for one hour. To the reaction solution was added a saturated aqueous solution of sodium bicarbonate, followed by extracting with ethyl acetate. The organic layer was washed with a saturated aqueous solution of NaCl and dried over anhydrous magnesium sulfate. The residue obtained by evaporating the solvent was purified by silica gel column chromatography (eluting with chloroform-methanol). After the solvent was evaporated, the residue was dissolved in 5 ml of chloroform, 500 μl of a 4N HCl/ethyl acetate solution was added with ice cooling, and the mixture was stirred for 30 minutes. After evaporation of the solvent, the residue was crystallized from ethanol and diethyl ether to give 90 mg of (Z)-4,4-difluoro-1-(4-methyl-2-phenylthiazole-5-carbonyl)-5-[2-(4-methylpiperazine-1-yl)ethylidene]-2,3,4,5-tetrahydro-1H-1-benzoazepine dihydrochloride as a colorless powder.

The compounds of Examples 9-1 (Table 10) and 9-2 (Table 11) were obtained in the same manner as in Example 9.

EXAMPLE 10
(Table 11)

To 120 mg of ethyl (Z)-2-(1-{[4,4-difluoro-1-(4-methyl-2-phenylthiazole-5-carbonyl)-2,3,4,5-tetrahydro-1H-1-benzoazepin-5-ylidene]acetyl}-4-piperidyl)acetate in 10 ml of a 90% aqueous solution of methanol was added 33 mg of potassium carbonate, followed by stirring at room temperature for three hours. To the reaction solution was added ethyl acetate, and the mixture was washed with a saturated aqueous solution of sodium bicarbonate and a saturated aqueous solution of NaCl, followed by drying over anhydrous magnesium sulfate. The residue obtained by evaporation of the solvent was purified by silica gel column chromatography (eluting with chloroform-methanol). The resulting residue was crystallized from diethyl ether to give 110 mg of (Z)-2-(1-{[4,4-difluoro-1-(4-methyl-2-phenylthiazole-5-carbonyl)-2,3,4,5-tetrahydro)-1H-1-benzoazepine-5-ylidene]acetyl}-4-piperidyl)ethanol as a colorless powder.

The compounds of Examples 10-1 (Table 11) , 10-2 (Table 4) and 10-3 (Table 10) were obtained in the same manner as in Example 10.

EXAMPLE 11
(Table 11)

To a solution of 500 mg of (Z)-N-(1-benzyl-4-piperidyl)-[4,4-difluoro-1-(4-methyl-2-phenylthiazole-5-carbonyl)-2,3,4,5-tetrahydro-1H-1-benzoazepin-5-ylidene]-acetamide in 15 ml of dichloromethane was added 88 μl of 1-chloroethyl chloroformate, and the mixture was stirred for 3.5 hours with heating under refluxing. The solvent was evaporated, and 20 ml of methanol was added to the residue, followed by stirring at 50° C. for two hours. After this was cooled down to room temperature, a saturated aqueous solution of sodium bicarbonate was added thereto, followed by extracting with ethyl acetate. The organic layer was washed with a saturated aqueous solution of NaCl and dried over anhydrous magnesium sulfate, and the solvent was evaporated. The residue was purified by silica gel column chromatography (eluting with methanol-aqueous ammonia). After making into a hydrochloride using a 4N HCl/ethyl acetate solution, the salt was collected by filtration and washed with ethyl acetate to give 273 mg of (Z)-[4,4-difluoro-1-(4-methyl-2-phenylthiazole-5-carbonyl)-2,3,4,5-tetrahydro-1H-1-benzoazepin-5-ylidene]-N-(4-piperidyl)acetamide monohydrochloride as a colorless powder.

EXAMPLE 12
(Table 11)

To a solution of 60 mg of (Z)-[4,4-difluoro-1-(4-methyl-2-phenylthiazole-5-carbonyl)-2,3,4,5-tetrahydro-1H-1-benzoazepin-5-ylidene]-N-(4-piperidyl)acetamide in 5 ml of dichloromethane were added 70 μl of a 40% aqueous solution of formaldehyde, 74 μl of acetic acid and 30 mg of sodium triacetoxy borohydride, followed by stirring at room temperature for six hours. To the reaction solution was added a saturated aqueous solution of sodium bicarbonate, followed by extracting with ethyl acetate. The organic layer was washed with a saturated aqueous solution of NaCl and dried over anhydrous magnesium sulfate, followed by evaporating the solvent therefrom. The residue was purified by silica gel column chromatography (eluting with chloroform) and crystallized from diethyl ether to give 53 mg of (Z)-[4,4-difluoro-1-(4-methyl-2-phenylthiazole-5-carbonyl)-2,3,4,5-tetrahydro-1H-1-benzoazepin-5-ylidene]-N-(1methyl-4-piperidyl)acetamide as a colorless powder.

EXAMPLE 13
(Table 11)

To a solution of 420 mg of tert-butyl (Z)-{4-[({[4,4-difluoro-1-(4-methyl-2-phenylthiazole-5-carbonyl)-2,3,4,5-tetrahydro-1H-1-benzoazepin-5-ylidene]acetyl}amino)methyl]-piperidino}carboxylate in 6 ml of ethyl acetate was added 660 μl of a 4N HCl/ethyl acetate solution, followed by stirring at room temperature for 1.5 days. To the reaction solution was added a saturated aqueous solution of sodium bicarbonate, followed by extracting with ethyl acetate. The organic layer was washed with a saturated aqueous solution of NaCl and dried over anhydrous magnesium sulfate, followed by evaporating the solvent. The residue was purified by silica gel column chromatography (eluting with methanol) and, after making into a hydrochloride using a 4N HCl/ethyl acetate solution, the salt was collected by filtration and washed with ethyl acetate to give 97 mg of (Z)-[4,4-difluoro-1-(4-methyl-2phenyl-thiazole-5-carbonyl)-2,3,4,5-tetrahydro-1H-1-benzoazepin-5-ylidene]-N-[(4-piperidyl)methyl]acetamide dihydrochloride as a colorless powder.

The compounds of Examples 13-1 to 13-4 were obtained in the same manner as in Example 13 (Table 11).

EXAMPLE 14
(Table 11)

To a solution of 200 mg of (Z)-1-{[4,4-difluoro-1-(4-methyl-2-phenylthiazole-5-carbonyl)-2,3,4,5-tetrahydro-1H-1-benzoazepin-5-ylidene]acetyl}piperidin-4-one in a mixture of 6 ml of dichloromethane and 3 ml of methanol were added 29 mg of hydroxylamine monohydrochloride and 59 μl of triethylamine, followed by stirring at room temperature for 22 hours. After evaporating the solvent, the residue was purified by silica gel column chromatography (eluting with chloroform-methanol), followed by crystallizing from diethyl ether to give 61 mg of (Z)-4,4-difluoro-5-{2-[4-(hydroxyimino)piperidino]-2-oxo-ethylidene}-1-(4-methyl-2-phenylthiazole-5-carbonyl)-2,3,4,5-tetrahydro-1H-1-benzoazepine as a colorless powder.

The compounds of Examples 14-1 to 14-8 were obtained in the same manner as in Example 14 (Table 11).

EXAMPLE 15
(Table 11)

(Z)-1-{[4,4-Difluoro-1-(4--methyl-2-phenylthiazole-5-carbonyl)-2,3,4,5-tetrahydro-1H-1-benzoazepin-5-ylidine]-acetyl}piperidin-4-one (150 mg) was dissolved in 10 ml of ethanol, and 26 mg of acetic acid hydrazide was added thereto, followed by stirring under refluxing for 9 hours. The solvent was evaporated, and the residue was purified by silica gel chromatography (eluting with chloroform-methanol). The resulting residue was crystallized from diethyl ether to give 100 mg of (Z)-N-acetyl-N'-(1-{[4,4-difluoro-1-(4-methyl-2-phenylthiazole-5-carbonyl)-2,3,4,5-tetrahydro-1H-1-benzoazepin-5-ylidene]acetyl}piperidin-4-ylidene)hydrazide as a colorless powder.

EXAMPLE 16

(Table 11)

A solution of 51 mg of (Z)-4,4-difluoro-5-{2-[4-(hydroxyimino)piperidino]-2-oxoethylidene}-1-(4-methyl-2-phenylthiazole-5-carbonyl)-2,3,4,5-tetrahydro-1H-1-benzoazepine in a mixture of 800 μl of acetic anhydride and 800 μl of pyridine was stirred at room temperature for eight hours. The solvent was evaporated, the residue was dissolved in ethyl acetate, and the solution was washed with 1N hydrochloric acid and a saturated aqueous solution of NaCl. After drying over anhydrous magnesium sulfate, the solvent was evaporated therefrom. The residue was purified by silica gel column chromatography (eluting with chloroform) to give 36 mg of (Z)-4,4-difluoro-5-{2-[4-(acetoxyimino)piperidino]-2-oxoethylidene}-1-(4-methyl-2-phenylthiazole-5-carbonyl)-2,3,4,5-tetrahydro-1H-1-benzoazepine as a colorless solid.

The compounds of Examples 16-1 to 16-3 were obtained in the same manner as in Example 16 (Table 11).

EXAMPLE 17

(Table 11)

A solution of 190 mg of (Z)-[4,4-difluoro-1-(4-methyl-2-phenylthiazole-5-carbonyl)-2,3,4,5-tetrahydro-1H-1-benzoazepin-5-ylidene]-N-[(1-trityl-1H-imidazol-4-yl)methyl]-acetamide in 20 ml of a 90% aqueous solution of acetic acid was stirred at 60° C. for 1.5 hours. After evaporating the solvent therefrom, ethyl acetate and 3N hydrochloric acid were added to undergo liquid separation. The aqueous layer was neutralized with potassium carbonate and extracted with ethyl acetate. The organic layer was washed with a saturated aqueous solution of NaCl and dried over anhydrous magnesium sulfate, and the solvent was evaporated. The residue was collected by filtration and washed with ethyl acetate to give 110 mg of (Z)-[4,4-difluoro-1-(4-methyl-2-phenylthiazole-5-carbonyl)-2,3,4,5-tetrahydro-1H-1-benzoazepin-5-ylidene]-N-[(1H-imidazol-4-yl)methyl]acetamide as a colorless powder.

The compounds of Examples 17-1 and 17-2 were obtained in the same manner as in Example 17 (Table 11).

EXAMPLE 18

(Table 11)

To a solution of 140 mg of (Z)-(1-{[4,4-difluoro-1-(4-methyl-2-phenylthiazole-5-carbonyl)-2,3,4,5-tetrahydro-1H-1-benzoazepin-5-ylidene]acetyl}-4-piperidyl)-N-methoxy-N-methylcarboxamide in 10 ml of tetrahydrofuran was added 280 μl of a solution of 1.05N methyl lithium in diethyl ether at −30° C. This was stirred at −30° C. for three hours together while adding 200 μl of the above-mentioned methyl lithium solution thereto every 40 minutes. To the reaction solution was added 1N hydrochloric acid, followed by extracting with ethyl acetate. The organic layer was washed with a saturated aqueous solution of NaCl and dried over anhydrous magnesium sulfate, followed by evaporating the solvent therefrom. The residue was purified by silica gel column chromatography (eluting with chloroform) to give 20 mg of (Z)-4,4-difluoro-5-[2-(4-acetylpiperidino)-2-oxoethylidene]-1-(4-methyl-2-phenylthiazole-5-carbonyl)-2,3,4,5-tetrahydro-1H-1-benzoazepine as a yellow amorphous solid.

EXAMPLE 19

(Table 11)

To a solution of 260 mg of (Z)-[4,4-difluoro-1-(4-methyl-2-phenylthiazole-5-carbonyl)-2,3,4,5-tetrahydro-1H-1-benzoazepin-5-ylidene]acetic acid in 20 ml of tetrahydrofuran were added 118 mg of 1-hydroxybenzotriazole, 167 mg of 1-ethyl-3-(3-dimethylaminopropyl)carbodiimide monohydro-chloride, 600 mg of (dibenzyl) [2-(4-piperidyl)ethyl]amine and 310 μl of triethylamine, and the mixture was stirred at room temperature for 18 hours. To the reaction solution was added a saturated aqueous solution of sodium bicarbonate, and the mixture was extracted with ethyl acetate. The organic layer was washed with a saturated aqueous solution of NaCl and dried over magnesium sulfate, and the solvent was evaporated therefrom. The resulting residue (385 mg) was dissolved in 10 ml of dichloroethane, 64 μl of 1-chloroethyl chloroformate was added thereto, and the mixture was stirred with heating under refluxing for 4.5 hours. The solvent was evaporated, 10 ml of methanol was added to the residue, and the mixture was stirred with heating under refluxing for 4.5 hours. After cooling to room temperature, a saturated aqueous solution of sodium bicarbonate was added, and the mixture was extracted with ethyl acetate. The organic layer was washed with a saturated aqueous solution of NaCl and dried over anhydrous magnesium sulfate, and the solvent was evaporated therefrom. The residue was purified by silica gel column chromatography (eluting with chloroform-methanol). The resulting residue (22 mg) was dissolved in 0.1 ml of ethyl acetate, then 30 μl of a 4N HCl/ethyl acetate solution was added to the solution, and the mixture was stirred at room temperature. The solvent was evaporated therefrom, and the resulting solid was collected by filtration to give 14 mg of (Z)-4,4-difluoro-5-(2-{4-[2-(benzylamino)ethyl]piperidino)-2-oxoethylidene)-1-(4-methyl-2-phenylthiazole-5-carbonyl)-2,3,4,5-tetrahydro-1H-1-benzoazepine monohydrochloride as a colorless powder.

EXAMPLE 20

(Table 11)

To a solution of 250 mg of ethyl (Z)-[(1-{[4,4-difluoro-1-(4-methyl-2-phenylthiazole-5-carbonyl)-2,3,4,5-tetrahydro-1H-1-benzoazepin-5-ylidene]acetyl}-4-piperidyl)-(trifluoroacetyl)amino]acetate in 5 ml of ethanol was added a solution of 100 mg of potassium carbonate in 2 ml of water, and the mixture was stirred at room temperature for three days. After evaporation of the solvent, water was added to the residue, and the mixture was washed with ethyl acetate (a washing A) The aqueous layer was acidified and extracted with ethyl acetate. The organic layer was washed with a saturated aqueous solution of NaCl and dried over anhydrous magnesium sulfate, and the solvent was evaporated therefrom. The resulting residue was collected by filtration to give 60 mg of (Z)-[(1-{[4,4-difluoro-1-(4-methyl-2-phenylthiazole-5-carbonyl)-2,3,4,5-tetrahydro-1H-1-benzoazepin-5-ylidene]acetyl}-4-piperidyl)(trifluoroacetyl)amino]acetic acid as a colorless amorphous powder.

EXAMPLE 21

(Table 11)

The washing A in Example 20 was extracted with 0.5N hydrochloric acid. The resulting aqueous layer was made alkaline and extracted with ethyl acetate. The organic layer was washed with a saturated aqueous solution of NaCl and dried over anhydrous magnesium sulfate, and the solvent was evaporated therefrom. The resulting residue was collected by filtration to give 30 mg of ethyl(Z)-[(1-{[4,4- difluoro-1-(4-methyl-2-phenylthiazole-5-carbonyl)-2,3,4,5-tetrahydro-1H-1-benzoazepin-5-ylidene]acetyl}-4-piperidyl)amino]acetate as a colorless amorphous solid.

EXAMPLE 22
(Table 11)

To a solution of 240 mg of ethyl (Z)-[(1-{[4,4-difluoro-1-(4-methyl-2-phenylthiazole-5-carbonyl)-2,3,4,5-tetrahydro-1H-1-benzoazepin-5-ylidene]acetyl}-4-piperidyl)-(trifluoroacetyl)amino]acetate in 5 ml of ethanol was added a solution of 100 mg of potassium carbonate in 4 ml of water, and the mixture was stirred at 40° C. for 18 hours. After evaporation of the solvent, 1N hydrochloric acid was added to the residue, and the mixture was washed with ethyl acetate. The aqueous layer was neutralized and extracted with ethyl acetate. The organic layer was washed with a saturated aqueous solution of NaCl and dried over anhydrous magnesium sulfate, and the solvent was evaporated therefrom. The resulting residue was crystallized from diethyl ether to give 40 mg of (Z)-[(1-{[4,4-difluoro-1-(4-methyl-2-phenylthiazole-5-carbonyl)-2,3,4,5-tetrahydro-1H-1-benzoazepin-5-ylidene]acetyl}-4-piperidyl)amino]acetic acid as a pale yellow powder.

EXAMPLE 23
(Table 11)

Ethyl (Z)-(1-{[4,4-difluoro-1-(4-methyl-2-phenylthiazole-5-carbonyl)-2,3,4,5-tetrahydro-1H-1-benzoazepin-5-yl-idene]acetyl}piperidin-4-ylidene)acetate (150 mg) was dissolved in 5 ml of acetic acid, 1 ml of concentrated hydrochloric acid was added to the solution, and the mixture was stirred at 50° C. for 18 hours. The reaction solution was diluted with water and extracted with ethyl acetate. The organic layer was washed with a saturated aqueous solution of NaCl and dried over anhydrous magnesium sulfate, and the solvent was evaporated therefrom. The resulting oily residue (180 mg) was dissolved in 10 ml of tetrahydrofuran, then 60 mg of 1-hydroxybenzotriazole, 90 mg of 1-ethyl-3-(3-dimethylamino-propyl) carbodiimide monohydrochloride and 200 µl of 28% aqueous ammonia were added thereto, and the mixture was stirred at room temperature for 18 hours. A saturated aqueous solution of sodium bicarbonate was added to the reaction solution, and the mixture was extracted with ethyl acetate. The organic layer was washed with a saturated aqueous solution of NaCl and dried over magnesium sulfate, and the solvent was evaporated therefrom. The residue was purified by silica gel column chromatography (eluting with ethyl acetate-hexane). The resulting residue was crystallized from ethanol to give 40 mg of (Z)-(1-{[4,4-difluoro-1-(4-methyl-2-phenylthiazole-5-carbonyl)-2,3,4,5-tetrahydro-1H-1-benzoazepin-5-ylidene]acetyl}piperidin-4-ylidene)acetamide as a colorless powder.

EXAMPLE 24
(Table 11)

Sodium hydride (47 mg) and 58 mg of bromoacetamide were added to a solution of 150 mg of (Z)-4,4-difluoro-5-{2-[4-(hydroxyimino)piperidino]-2-oxoethylidene}-1-(4-methyl-2-phenylthiazole-5-carbonyl)-2,3,4,5-tetrahydro-1H-1-benzoazepine in 10 ml of tetrahydrofuran, and the mixture was stirred at 0° C. for three hours. The reaction solution was diluted with ethyl acetate and washed with a saturated aqueous solution of NaCl and dried over magnesium sulfate, and the solvent was evaporated therefrom. The residue was purified by silica gel column chromatography (eluting with chloroform-methanol). The resulting residue was crystallized from diethyl ether to give 110 mg of (Z)-[(1-{[4,4-difluoro-1-(4-methyl-2-phenylthiazole-5-carbonyl)-2,3,4,5-tetrahydro-1H-1-benzoazepin-5-ylidene]acetyl}piperidin-4-ylidene)aminoxy]acetamide as a pale yellow powder.

The compounds of Examples 24-1 and 24-2 were obtained in the same manner as in Example 24 (Table 11).

EXAMPLE 25
(Table 11)

Potassium carbonate (30 mg) and 50 µl of ethyl bromoacetate were added to a solution of 200 mg of (Z)-4,4-difluoro-5-(2-[4-(methylamino)piperidino]-2-oxoethylidene-1-(4-methyl-yl2-phenylthiazole-5-carbonyl)-2,3,4,5-tetrahydro-1H-1-benzoazepine in 5 ml of acetonitrile, and the mixture was stirred at room temperature for 18 hours. To the reaction solution was added a saturated aqueous solution of sodium bicarbonate, and the mixture was extracted with ethyl acetate. The organic layer was washed with a saturated aqueous solution of NaCl and dried over magnesium sulfate, and th e solvent was evaporated therefrom. The residue was purified by silica gel column chromatography (eluting with chloroform-methanol) . The resulting residue (200 mg) was dissolved in 10 ml of chloroform, then 500 µl of a 4N HCl/ethyl acetate solution was added thereto, and the mixture was stirred at room temperature. The solvent was evaporated therefrom, and the resulting residue was crystallized from ethanol-diethyl ether to give 140 mg of ethyl (Z)-[(1-{[4,4-difluoro-1-(4-methyl-2-phenylthiazole-5-carbonyl)-2,3,4,5-tetrahydro-1H-1-benzoazepin-5-ylidene]-acetyl}-4-piperidyl)(methyl)amino]acetate monohydrochloride as a colorless powder.

The compounds of Examples 25-1 to 25-3 were obtained in the same manner as in Example 25 (Table 11).

EXAMPLE 26
(Table 11)

Sodium hydride (40 mg) was added to a solution of 220 mg of (Z)-4,4-difluoro-1-(4-methyl-2-phenylthiazole-5-carbonyl-yl)-5-[2-oxo-2-(3-oxopiperazin-1-yl)ethylidene]-2,3,4,5-tetrahydro-1H-1-benzoazepine in 8 ml of tetrahydrofuran with ice cooling, and the mixture was stirred at room temperature for 20 minutes. To the reaction solution was added 110 µl of ethyl bromoacetate, and the mixture was stirred at room temperature for five hours. To the reaction solution was added a saturated aqueous solution of sodium bicarbonate, and the mixture was washed with ethyl acetate (a washing B). The aqueous layer was acidified and extracted with ethyl acetate. The organic layer was washed with a saturated aqueous solution of NaCl and dried over magnesium sulfate, and the solvent was evaporated therefrom. The residue was purified by silica gel column chromatography (eluting with chloroform-methanol). The resulting residue was crystallized from diethyl ether to give 90 mg of (Z)-(4-{[4,4-difluoro-1-(4-methyl-2-phenylthiazole-5-carbonyl)-2,3,4,5-tetrahydro-1H-1-benzoazepin-5-ylidene]acetyl}-2-oxopiperazin-1-yl)acetic acid as a colorless powder.

EXAMPLE 27
(Table 11)

The washing B of Example 26 was washed with a saturated aqueous solution of NaCl and dried over magnesium sulfate, and the solvent was evaporated therefrom. The residue was purified by silica gel column chromatography (eluting with chloroform-methanol). The resulting solid was collected by filtration to give 80 mg of ethyl (Z)-(4-{[4,4-difluoro-1-(4-methyl-2-phenylthiazole-5-carbonyl)-2,3,4,5-tetrahydro-1H-1-benzoazepin-5-ylidene]acetyl}-2-oxopiperazin-1-yl)acetate as a colorless amorphous solid.

EXAMPLE 28

(Table 11)

(Z)-3-(4-{[4,4-Difluoro-1-(4-methyl-2-phenylthiazole-5-carbonyl)-2,3,4,5-tetrahydro-1H-1-benzoazepin-5-ylidene]-acetyl}piperazin-1-yl)-3-oxopropionic acid (190 mg) was dried in vacuo at 50° C. The residue was extracted with ethyl acetate. The organic layer was washed with a saturated aqueous solution of NaCl and dried over magnesium sulfate, and the solvent was evaporated therefrom. The resulting residue was collected by filtration to give 20 mg of (Z)-4,4-difluoro-5-[2-(4-acetylpiperazin-1-yl)-2-oxoethylidene]-1-(4-methyl-2-phenylthiazole-5-carbonyl)-2,3,4,5-tetrahydro-1H-1-benzoazepine as a colorless amorphous solid.

EXAMPLE 29

(Table 11)

Sodium borohydride (36 mg) was added to a solution of 400 mg of ethyl (Z)-3-(1-{[4,4-difluoro-1-(4-methyl-2-phenylthiazole-5-carbonyl)-2,3,4,5-tetrahydro-1H-1-benzoazepin-5-ylidene]acetyl}-4-piperidyl)-3-oxopropionate in 10 ml of tetrahydrofuran-ethanol (1:1), and the mixture was stirred at room temperature for 28 hours. The reaction solution was diluted with ethyl acetate, washed with a saturated aqueous solution of NaCl and dried over magnesium sulfate, and the solvent was evaporated therefrom. The residue was purified by silica gel column chromatography (eluting with chloroform-methanol). The resulting residue was collected by filtration to give 300 mg of (Z)-1-(1-{[4,4-difluoro-1-(4-methyl-2-phenylthiazole-5-carbonyl)-2,3,4,5-tetrahydro-1H-1-benzoazepin-5-ylidene]acetyl}-4-piperidyl)propane-1,3-diol (29a) as a colorless amorphous solid and 90 mg of ethyl (Z)-3-(1-{[4,4-difluoro-1-(4-methyl-2-phenylthiazole-5-carbonyl)-2,3,4,5-tetrahydro-1H-1-benzoazepin-5-ylidene]acetyl}-4-piperidyl)-3-hydroxypropionate (29b) as a colorless amorphous solid.

Structural formulae and physicochemical properties of the compounds of the above Examples are shown in Tables 2 to 11. (For the compounds of the Referential Examples, their physicochemical properties are shown in Table 1.)

Symbols used in the tables have the following meanings.

Rf.: Referential Example No.
Ex.: Example No.
Sal.: salt
-: free base
For.: form
NMR: nucleomagnetic resonance spectrum (internal standard is TMS, unless otherwise mentioned)
m/z: mass spectrometric data (m/z)
pow.: colorless powder
amo.: colorless amorphous substance
oil: colorless oily substance
ypow.: pale yellow powder
opow.: yellowish brown powder
yamo.: pale yellow amorphous substance
oamo.: yellowish brown amorphous substance
Me: methyl group
Et: ethyl group
Pr: propyl group
iPr: isopropyl group
Ac: acetyl group
Boc: tert-butoxycarbonyl group
Tr: trityl group
Bzl: benzyl group

TABLE 1

| Rf. | For. | |
|---|---|---|
| 1 | pow. | NMR: (CDCl$_3$); 2.3–2.8(5H,m), 3.3–3.6(3H,m), 3.6–4.1(3H,m), 6.23(1H,s), 6.5–7.3(4H,m). |
| 2 | amo. | NMR: (CDCl$_3$); 2.32(3H,s), 2.41(3H,s), 3.5–3.8(2H,m) 3.9–4.0(1H,m), 5.89(1H,s), 7.1–7.4(6H,m), 7.65(2H,d). |
| 3 | pow. | NMR: (CDCl$_3$); 2.33(3H,s), 2.4–2.6(1H,m), 3.3–3.8(3H,m), 6.23(1H,s), 6.5–6.9(2H,m), 7.0–7.3(2H,m). |

TABLE 2

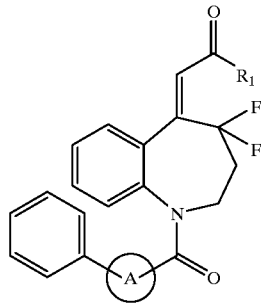

| Ex. | R$_1$ | A | Sal. | For. | |
|---|---|---|---|---|---|
| 1 | —OMe | (thiazole with Me) | — | amo. | NMR: (CDCl$_3$); 2.43–2.63(5H, m), 3.27(1H, br), 3.81(3H, s), 5.02(1H, br), 6.21(1H, s), 6.99(1H, d), 7.24–7.28(1H, m), 7.36–7.45(5H, m), 7.68–7.70(2H, m). |

TABLE 2-continued
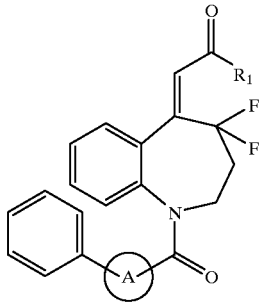
| Ex. | R₁ | A | Sal. | For. | |
|---|---|---|---|---|---|
| 1-1 | —OMe | 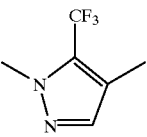 | — | amo. | NMR: (CDCl₃); 2.41(1H, br), 2.74(1H, br), 3.28(1H, br), 3.83(3H, s), 5.00(1H, br), 6.18(1H, s), 6.9–7.0(2H, m), 7.3–7.6(8H, m). |
| 1-2 | —OMe | 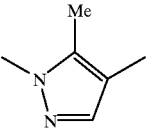 | — | pow. | NMR: (CDCl₃); 2.3–2.5(1H, br), 2.54(3H, s), 2.6–2.8(1H, br), 3.2–3.3(1H, br), 3.79(3H, s), 5.03(1H, br), 6.15(1H, s), 6.21(1H, s), 7.06(1H, d), 7.3–7.5(8H, m). |
| 1-3 | —OMe | 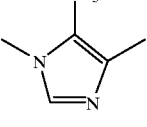 | — | amo. | NMR: (CDCl₃,); 2.15–3.00(3H, br), 3.30(1H, br), 3.80(3H, s), 4.98(1H, br), 6.12(1H, s), 7.06(1H, d), 7.14–7.58(8H, m). |
| 2 | —OH | 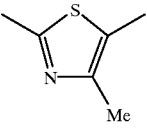 | — | pow. | NMR: (CDCl₃); 2.64(3H, s), 6.24(1H, s), 7.00(1H, d), 7.25–7.46(7H, m), 7.68–7.70(2H, m). |
| 2-1 | —OH | 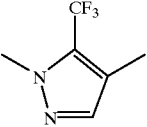 | — | amo | NMR: (CDCl₃); 2.44(1H, br), 2.79(1H, br), 3.29(1H, br), 4.99(1H, br), 6.22(1H, s), 6.9–7.0(2H, m), 7.3–7.5(8H, m). |
| 2-2 | —OH | 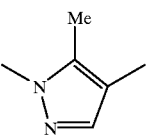 | — | pow. | NMR: (CDCl₃); 2.3–2.5(1H, br), 2.54(3H, s), 2.6–2.8(1H, br), 3.2–3.3(1H, br), 4.9–5.1(1H, br), 6.1–6.2(2H, m), 7.07(1H, d), 7.3–7.5(8H, m). |
| 2-3 | —OH | 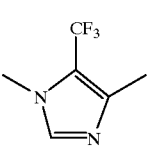 | — | amo. | NMR: (CDCl₃); 2.37(1H, br), 2.84(1H, br), 3.30(1H, br), 5.00(1H, br), 6.17(1H, s), 7.18–7.60(9H, m). |

TABLE 3

[Structure: benzazepine with gem-difluoro, exocyclic =CH–C(=O)–R1, N-acyl with 4-methyl-2-phenylthiazole-5-carbonyl]

| Ex. | R₁ | Sal. | For. | Data |
|---|---|---|---|---|
| 3 | -N(piperazine)N-CH₂CH₂OH | HCl | pow. | m/z: 553(FAB, M⁺+1) NMR: (DMSO-d₆); 2.4–2.5(1H, br), 2.50(3H, s), 2.9–3.4(4H, m), 4.0–4.4(4H, m), 4.08(1H, br), 4.42(1H, d), 4.83(1H, br), 5.38(1H, br), 6.80(1H, s), 7.15(1H, d), 7.33(1H, t), 7.4–7.5(4H, m), 7.64(1H, d), 7.73(2H, d), 10.86(1H, br). |
| 3-1 | -N(piperidin-4-one) | — | amo. | m/z: 522(FAB, M⁺+1) NMR: (CDCl₃); 1.60(3H, br), 2.51–2.54(6H, m), 2.64(4H, br), 3.84(2H, br), 6.40(1H, s), 7.01(1H, d), 7.26–7.46(6H, m), 7.68–7.70(2H, m). |
| 3-2 | -N(piperidin-4-ol) | — | amo. | m/z: 524(FAB, M⁺+1) NMR: (CDCl₃); 1.5–1.6(2H, m), 1.8–1.9(2H, m), 2.3–2.6(1H, m), 2.63(3H, s), 3.32(2H, br), 3.7–3.8(2H, m), 4.0–4.2(2H, m), 6.34(1H, s), 6.98(1H, d), 7.2–7.5(6H, m), 7.70(2H, d). |
| 3-3 | -N(piperidin-4-yl)-CONH₂ | — | pow. | m/z: 551(FAB, M⁺+1) NMR: (CDCl₃); 1.65–1.80(2H, m), 1.85–2.00(2H, m), 2.39–2.47(2H, m), 2.63(3H, s), 2.84(1H, m), 3.18(1H, m), 3.94(1H, d), 4.56(1H, br), 5.41–5.50(2H, br), 6.32(1H, s), 6.98(1H, d), 7.24(1H, m), 7.34–7.42(4H, m), 7.45(1H, m), 7.68–7.70(2H, m). |
| 3-4 | -N(piperazine)N-Me | 2HCl | pow. | m/z: 523(FAB, M⁺+1) NMR: (DMSO-d₆); 2.4–2.5(1H, m), 2.54(3H, s), 2.79(3H, s), 2.9–3.3(3H, m), 3.45(2H, d), 3.64(1H, br), 4.09(1H, d), 4.43(1H, d), 4.83(1H, br), 6.80(1H, s), 7.14(1H, d), 7.33(1H, t), 7.4–7.6(4H, m), 7.66(1H, d), 7.73(2H, d), 11.58(1H, br). |
| 3-5 | -N(piperazine)N-Et | 2HCl | pow. | m/z: 537(FAB, M⁺+1) NMR: (DMSO-d₆); 1.27(3H, t), 2.76–2.94(2H, m), 3.16(4H, m), 3.51(2H, m), 4.10(1H, m), 4.44(1H, d), 4.90(1H, br), 6.79(1H, s), 7.15(1H, d), 7.34(1H, t), 7.42–7.48(4H, m), 7.62–7.64(2H, m), 11.20(1H, br). |
| 3-6 | -N(piperazine)N-iPr | HCl | pow. | m/z: 551(FAB, M⁺+1) NMR: (CDCl₃); 1.4–1.5(6H, m), 2.73(3H, s), 3.3–3.5(3H, m), 3.77(1H, t), 4.34(1H, br), 4.73(1H, d), 6.42(1H, br), 7.01(1H, d), 7.3–7.5(6H, m), 7.86(2H, d), 12.97(1H, br). |
| 3-7 | -N(piperazine)N-CH₂CH₂OH | 2HCl | pow. | m/z: 553(FAB, M⁺+1) NMR: (DMSO-d₆); 2.88–3.08(2H, m), 3.25(6H, br), 3.55–3.58(2H, m), 3.79(2H, br), 4.09(1H, m), 4.40(2H, d), 6.79(1H, s), 7.15(1H, d), 7.33(1H, t), 7.44–7.48(4H, m), 7.64(1H, d), 7.73(2H, d), 10.60(1H, br). |
| 3-8 | -N(piperazine)N-CH₂CH₂OMe | 2HCl | pow. | m/z: 567(FAB, M⁺+1) NMR: (DMSO-d₆); 2.44(1H, m), 2.51(3H, s), 2.99(1H, m), 3.36(2H, br), 3.54(2H, d), 3.76(3H, br), 4.10(1H, m), 4.35–4.60(8H, m), 4.83(1H, br), 6.80(1H, s), 7.15(1H, d), 7.33(1H, t), 7.40–7.50(4H, m), 7.65(1H, d), 7.73(2H, d), 11.32(1H, br). |
| 3-9 | -N(homopiperazine)N-Me | HCl | pow. | m/z: 537(FAB, M⁺+1) NMR: (DMSO-d₆); 2.51(3H, s), 2.71(3H, s), 6.81(1H, s), 7.14(1H, d), 7.2–7.6(6H, m), 7.6–7.7(2H, m), 10.9–11.2(1H, br). |

TABLE 3-continued

| Ex. | R₁ | Sal. | For. | |
|---|---|---|---|---|
| 3-10 | −N(piperazine)N−CH₂CH₂CH₂−OH | 2HCl | pow. | m/z: 567(FAB, M⁺+1)<br>NMR: (DMSO-d₆); 1.8–1.9(2H, m), 2.50(3H, s), 3.0–3.3(2H, m), 4.0–4.1(1H, br), 4.43(1H, d), 4.8–5.0(1H, br), 6.79(1H, s), 7.14(1H, d), 7.3–7.5(5H, m), 7.63(1H, d), 7.73(2H, d), 11.27(1H, br). |
| 3-11 | −N(piperazine)N−CH₂CONH₂ | 2HCl | pow. | m/z: 566(FAB, M⁺+1)<br>NMR: (DMSO-d₆); 2.51(3H, s), 3.17(3H, br), 3.54(1H, br), 4.02(2H, s), 6.79(1H, s), 7.15(1H, d), 7.31–7.35(1H, m), 7.42–7.50(4H, m), 7.63–7.66(1H, m), 7.72–7.74(3H, m), 8.09(1H, br). |
| 3-12 | −N(piperidine)−CH₂CONH₂ | — | pow. | m/z: 565(FAB, M⁺+1)<br>NMR: (CDCl₃); 1.1–1.3(3H, m), 1.81(2H, d), 2.1–2.2(3H, m), 2.3–2.7(3H, m), 2.63(3H, s), 3.13(1H, t), 3.87(1H, d), 4.62(1H, d), 5.52(2H, d), 6.33(1H, s), 6.98(1H, d), 7.2–7.5(6H, m), 7.70(2H, d). |
| 3-13 | −N(piperazine)N−CH₂CH₂CONH₂ | 2HCl | pow. | m/z: 580(FAB, M⁺+1)<br>NMR: (DMSO-d₆); 2.58(3H, s), 2.67(2H, d), 6.11(1H, s), 7.09–7.16(2H, m), 7.31–7.36(1H, m), 7.41–7.46(4H, m), 7.63–7.65(2H, m), 7.72–7.74(2H, m). |
| 3-14 | −N(piperazine)N−CH₂CH₂CO₂Me | HCl | pow. | m/z: 595(FAB, M⁺+1)<br>NMR: (CDCl₃); 2,.44(3H, s), 3.12(2H, m), 3.34(2H, m), 3.48(1H, m), 3.66(1H, m), 3.75(3H, s), 4.74(1H, d), 6.32(1H, s), 7.01(1H, d), 7.2–7.5(6H, m), 7.69(2H, d). |
| 3-15 | −N(piperazine)N−C(O)CH₂CO₂Et | — | amo. | m/z: 623(FAB, M⁺+1)<br>NMR: (CDCl₃); 1.29(3H, t), 2.63(3H, s), 4.21(2H, q), 6.32(1H, s), 7.00(1H, d), 7.3–7.5(6H, m), 7.69(2H, d). |
| 3-16 | −NH−CH₂CH₂−OH | HCl | pow. | NMR: (DMSO-d₆); 2.49(3H, s), 2.78(3H, s), 2.79(3H, s), 3.12–3.18(3H, m), 3.52(2H, br), 4.22(2H, br), 4.86(1H, br), 6.61(1H, s), 7.09(1H, d), 7.27–7.31(1H, m), 7.42–7.47(5H, m), 7.75–7.78(2H, m), 8.62–8.65(1H, m). |
| 3-17 | −NH−CH₂CH₂−OH | — | amo. | NMR: (CDCl₃); 1.5–1.7(2H, m), 1.8–1.9(2H, m), 2.3–2.7(1H, br), 2.63(3H, s), 3.3–3.4(2H, m), 3.7–3.8(1H, m), 3.9–4.2(2H, m), 6.34(1H, m), 6.98(1H, d), 7.2–7.5(6H, m), 7.68(2H, d). |
| 3-18 | −NH−CH₂CH₂CH₂CH₂−OH | — | amo. | NMR: (CDCl₃); 1.6–1.7(4H, m), 2.65(3H, s), 3.4–3.5(2H, m), 3.6–3.7(2H, m), 6.32(1H, s), 6.72(1H, br), 6.99(1H, d), 7.2–7.5(6H, m), 7.68(2H, d). |
| 3-19 | −N(CH₂CH₂OH)₂ | — | amo. | NMR: (CDCl₃); 2.64(3H, s), 3.5–3.6(4H, m), 3.7–3.8(2H, m), 3.9–4.0(2H, m), 6.49(1H, s), 6.99(1H, d), 7.2–7.5(6H, m), 7.21(2H, d). |

TABLE 3-continued

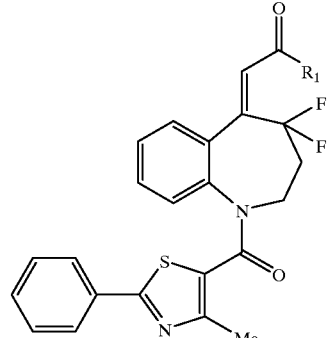

| Ex. | R₁ | Sal. | For. | |
|---|---|---|---|---|
| 3-20 | 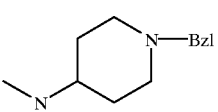 | HCl | pow. | NMR: (DMSO-d₆); 1.85–1.98(4H, m), 2.48(3H, s), 2.99–3.15(3H, m), 3.31–3.33(2H, m), 3.81–3.90(1H, m), 4.23–4.32(2H, m), 6.53(1H, s), 7.07(1H, d), 7.25–7.29(1H, m), 7.39–7.51(8H, m), 7.62–7.64(2H, m), 7.74–7.75(2H, m), 8.51(1H, d). |
| 3-21 | 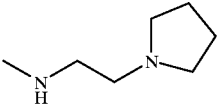 | HCl | pow. | NMR: (CDCl₃); 2.1–2.2(2H, m), 2.2–2.3(2H, m), 2.63(3H, s), 2.8–2.9(2H, m), 3.3–3.4(2H, m), 3.7–3.9(4H, m), 6.45(1H, s), 6.92(1H, d), 7.2–7.4(5H, m), 7.55(1H, m), 7.73(2H, d), 8.44(1H, m), 12.08(1H, br). |
| 3-22 | 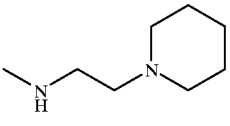 | HCl | pow. | NMR: (DMSO-d₆); 1.6–1.8(4H, m), 2.50(3H, s), 2.9–3.0(2H, m), 3.1–3.2(2H, m), 3.33(3H, br), 3.4–3.6(4H, m), 6.59(1H, s), 7.08(1H, d), 7.3–7.5(6H, m), 7.76(2H, d), 8.65(1H, t), 10.15(1H, br). |
| 3-23 | 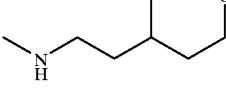 | — | pow. | NMR: (CDCl₃); 1.2–1.4(2H, m), 1.5–1.7(2H, m), 2.3–2.5(1H, br), 2.64(3H, s), 3.8–3.9(4H, m), 3.95(2H, m), 6.28(1H, s), 6.98(1H, d), 7.3–7.5(6H, m), 7.68(2H, d). |
| 3-24 | 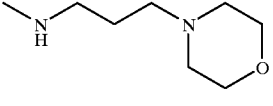 | HCl | pow. | NMR: (CDCl₃); 1.98–2.19(4H, m), 2.62(3H, s), 2.87(2H, br), 3.11–3.14(2H, m), 3.30–3.51(5H, m), 3.97(2H, br), 4.24(2H, br), 4.95(1H, br), 6.39(1H, s), 6.94(1H, d), 7.23(1H, m), 7.33–7.41(4H, m), 7.52(1H, m), 7.69–7.72(2H, m), 7.87(1H, t). |
| 3-25 | 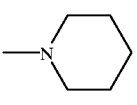 | — | amo. | NMR: (CDCl₃); 1.55–1.66(12H, m), 2.63(3H, s), 3.46(2H, br), 6.33(1H, s), 6.98(1H, m), 7.34–7.42(5H, m), 7.45(1H, m), 7.68–7.70(2H, m). |
| 3-26 | 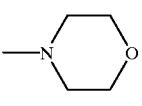 | — | amo. | NMR: (CDCl₃); 2.63(3H, s), 3.5–3.6(2H, m), 3.6–3.7(6H, m), 6.30(1H, s), 6.99(1H, d), 7.2–7.5(6H, m), 7.69(2H, d). |
| 3-27 | 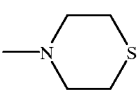 | — | amo. | NMR: (CDCl₃); 1.25–1.32(2H, m), 2.63(6H, br), 3.80(2H, br), 6.30(1H, s), 6.99(1H, d), 7.28(1H, m), 7.34–7.41(4H, m), 7.44(1H, m), 7.68–7.70(2H, m). |
| 3-28 | 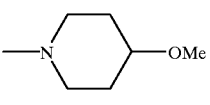 | — | amo. | NMR: (CDCl₃); 1.57(3H, br), 1.61–1.63(2H, m), 1.83–1.87(2H, m), 2.63(3H, s), 3.36(6H, br), 3.36–3.48(2H, m), 3.70(1H, m), 6.97(1H, d), 7.23(1H, m), 7.34–7.42(5H, m), 7.45(1H, m), 7.68–7.70(2H, m). |

TABLE 3-continued

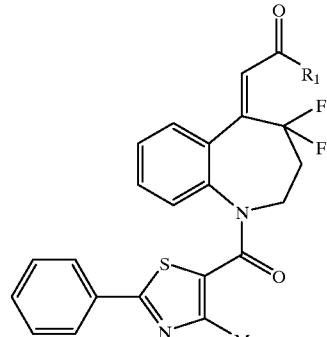

| Ex. | R₁ | Sal. | For. | |
|---|---|---|---|---|
| 3-29 | 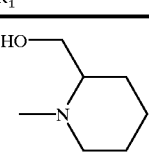 | — | amo. | NMR: (CDCl₃); 1.5–2.0(4H, br), 2.3–2.7(2H, br), 2.67(3H, s), 4.5–5.0(2H, m), 6.2–6.5(1H, m), 6.97(1H, d), 7.2–7.5(6H, m), 7.69(2H, d). |
| 3-30 | 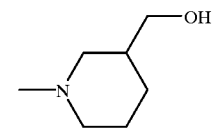 | — | amo. | NMR: (CDCl₃); 1.5–2.0(4H, br), 2.3–3.0(2H, br), 2.63(3H, s), 3.2–3.4(2H, br), 4.9–5.1(1H, br), 635(1H, d), 6.97(1H, t), 7.2–7.5(6H, m), 7.69(2H, d). |
| 3-31 | 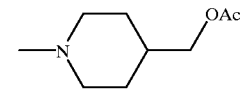 | — | amo. | NMR: (CDCl₃); 1.57(4H, br), 1.77(2H, m), 1.91(1H, m), 2.05(3H, s), 2.63(3H, s), 2.69(1H, m), 3.11(1H, t), 3.90(1H, br), 3.94(2H, m), 4.65(1H, m), 6.98(1H, d), 7.23–7.27(5H, m), 7.45(1H, m), 7.68–7.70(2H, m). |
| 3-32 | 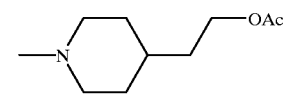 | — | pow. | NMR: (DMSO-d₆); 0.98–1.18(2H, m), 1.52(2H, br), 1.64–1.72(3H, m), 1.99(3H, s), 2.52(3H, s), 2.59–2.65(2H, m), 3.02(2H, br), 3.85–3.88(1H, m), 4.04(1H, br), 4.35(1H, br), 4.70(1H, br), 6.78(1H, s), 7.12(1H, d), 7.29–7.33(1H, m), 7.41–7.54(5H, m), 7.75–7.60(2H, m). |
| 3-33 | 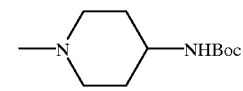 | — | yamo. | NMR: (CDCl₃); 1.44(9H, s), 1.89–2.11(4H, m), 2.63(3H, s), 2.77–2.83(1H, m), 3.16–3.23(1H, m), 6.32(1H, s), 6.98(1H, d), 7.18–7.44(7H, m), 7.68–7.70(2H, m). |
| 3-34 | 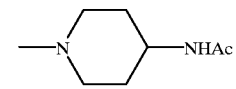 | — | pow. | NMR: (DMSO-d₆); 0.84–0.88(1H, m), 1.22–1.40(4H, m), 1.74–1.79(4H, m), 2.52(3H, s), 2.85(1H, br), 3.21(2H, br), 3.81(2H, br), 4.20(1H, br), 4.82(1H, br), 6.81(1H, s), 7.13(1H, d), 7.29–7.33(1H, m), 7.41–7.49(4H, m), 7.54–7.56(1H, m), 7.74–7.76(2H, m), 7.88(1H, d). |
| 3-35 | 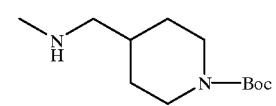 | — | amo | NMR: (DMSO-d₆); 1.11–1.20(2H, m), 1.45(9H, s), 1.71–1.78(3H, m), 2.63(3H, s), 2.65–2.75(2H, m), 3.25(2H, br), 4.12(2H, br), 6.07(1H, br), 6.35(1H, br), 6.98(1H, d), 7.26–7.30(1H, m), 7.33–7.45(5H, m), 7.67–7.70(2H, m). |
| 3-36 | 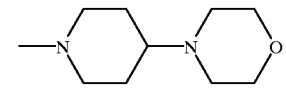 | HCl | pow. | NMR: (CDCl₃); 2.64(3H, s), 2.6–2.7(1H, m), 3.1–3.4(4H, m), 4.0–4.2(3H, m), 3.4–3.5(2H, m), 4.8–4.9(1H, m), 6.34(1H, s) 7.00(1H, d), 7.2–7.5(6H, m), 7.70(2H, d). |
| 3-37 | 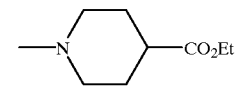 | — | amo. | NMR: (CDCl₃); 1.57(3H, t), 1.68–1.74(2H, m), 1.92–2.00(2H, m), 2.56(1H, m), 2.63(3H, s), 2.95(1H, br), 3.9–3.25(2H, m), 3.86(1H, m), 4.15(2H, q), 4.44(1H, br), 6.32(1H, s), 6.98(1H, d), 7.25(1H, m), 7.34–7.40(4H, m), 7.45(1H, m), 7.70(2H, m). |
| 3-38 | 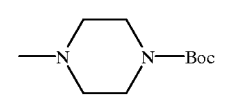 | — | amo. | NMR: (CDCl₃); 1.47(9H, s), 1.55(6H, br), 2.63(3H, s), 3.49(6H, br), 6.32(1H, s), 6.99(1H, d), 7.33–7.40(5H, m), 7.43(1H, m), 7.68–7.70(2H, m). |

TABLE 3-continued

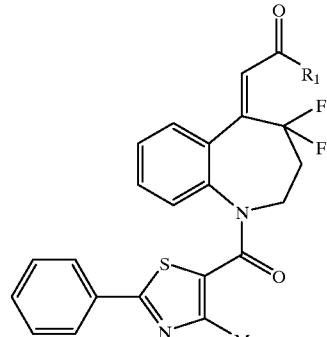

| Ex. | R₁ | Sal. | For. | |
|---|---|---|---|---|
| 3-39 | 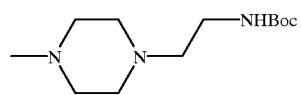 | — | amo. | NMR: (DMSO-d$_6$); 1.46(9H, s), 1.80(1H, br), 2.42–2.56(7H, m), 2.63(3H, s), 3.24–3.56(7H, m), 6.34(1H, br), 6.49(1H, br), 6.98–7.00(1H, m), 7.23–7.30(1H, m), 7.34–7.47(5H, m), 7.68–7.71(2H, m). |
| 3-40 | 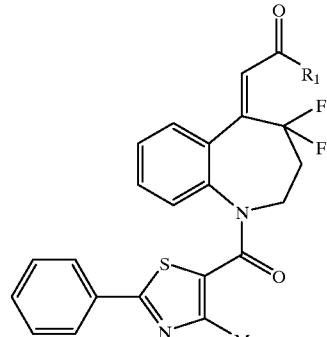 | 2HCl | pow. | NMR: (DMSO-d$_6$); 2.52(3H, s), 2.69–2.75(3H, m), 3.65(3H, br), 4.03(2H, br), 6.82(1H, s), 7.13(1H, d), 7.30–7.34(1H, m), 7.41–7.49(4H, m), 7.60(1H, m), 7.74–7.76(2H, m). |
| 3-41 | 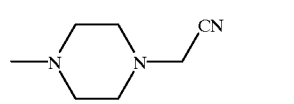 | HCl | pow. | NMR: (DMSO-d$_6$); 1.25(3H, t), 2.51(3H, s), 3.19(4H, br), 4.24(2H, q), 4.30(2H, br), 6.80(1H, s), 7.14(1H, d), 7.31–7.35(1H, m), 7.42–7.50(4H, m), 7.63–7.65(1H, m), 7.72–7.74(2H, m). |
| 3-42 | 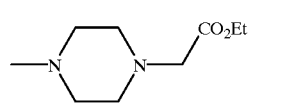 | HCl | pow. | NMR: (DMSO-d$_6$); 2.52(3H, s), 3.25(4H, br), 3.74(4H, br), 7.13–7.16(3H, m), 7.29–7.34(3H, m), 7.41–7.49(4H, m), 7.60(1H, m), 7.74–7.76(2H, m). |
| 3-43 | 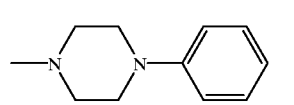 | HCl | pow. | NMR: (DMSO-d$_6$); 2.30(3H, s), 2.51(3H, s), 2.8–2.9(4H, m), 3.6–3.7(4H, m), 6.84(1H, s), 7.0–7.5(9H, m), 7.74(1H, d), 7.76(2H, d). |
| 3-44 | 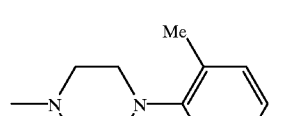 | HCl | pow. | NMR: (DMSO-d$_6$); 2.53(3H, s), 3.18(1H, br), 3.69–4.55(1H, br), 4.83(1H, br), 6.86(1H, s), 6.93(1H, t), 7.14(1H, d), 7.29–7.35(2H, m), 7.41–7.49(4H, m), 7.61(1H, m), 7.75(2H, d), 7.94(1H, t), 8.08(1H, m). |
| 3-45 | 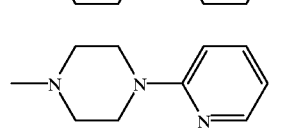 | HCl | pow. | NMR: (CDCl$_3$); 2.69(3H, s), 3.8–3.9(2H, m), 6.36(1H, s), 6.89(1H, br), 7.00(1H, d), 7.2–7.5(7H, m), 7.78(2H, d), 8.59(2H, d). |
| 3-46 | 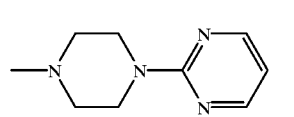 | HCl | pow. | NMR: (DMSO-d$_6$); 2.51(3H, s), 6.78(1H, s), 7.09(1H, d), 7.18–7.21(1H, m), 7.28–7.32(1H, m), 7.41–7.48(4H, m), 7.56–7.57(1H, m), 7.76–7.77(2H, m), 7.87–7.91(1H, m), 8.09(1H, d), 8.36(1H, d), 11.35(1H, br). |
| 3-47 | 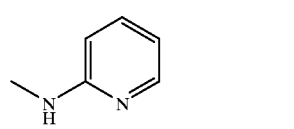 | — | pow. | NMR: (DMSO-d$_6$); 2.52(3H, s), 2.56(1H, br), 3.18(1H, br), 4.90(1H, br), 6.81(1H, s), 7.12(1H, d), 7.30–7.34(1H, m), 7.37–7.52(6H, m), 7.76–7.78(2H, m), 8.06–8.08(1H, m), 8.31(1H, d), 8.78(1H, d), 10.54(1H, br). |
| 3-48 | 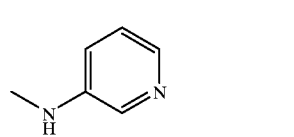 | — | amo. | NMR: (CDCl$_3$); 2.58(3H, s), 4.55(2H, d), 6.25(1H, m), 6.37(1H, s), 6.94(1H, d), 7.2–7.5(1H, m), 7.66(2H, d). |

TABLE 3-continued

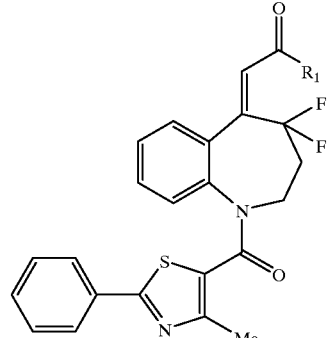

| Ex. | R₁ | Sal. | For. | |
|---|---|---|---|---|
| 3-49 | 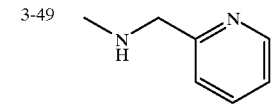 | HCl | pow. | NMR: (DMSO-d₆); 2.40(1H, br), 2.49(3H, s), 2.67(1H, br), 3.15(1H, br), 4.69(2H, br), 4.87(1H, br), 6.69(1H, s), 7.09(1H, d), 7.28–7.31(1H, m), 7.41–7.47(5H, m), 7.75–7.82(4H, m), 8.41(1H, t), 8.79(1H, m), 9.20(1H, t). |
| 3-50 | 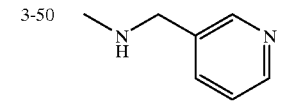 | HCl | pow. | NMR(DMSO-d₆); 2.40(1H, br) 2.49(3H, s), 3.20(1H, br), 3.70(1H, br), 4.60(2H, br), 4.80(1H, br), 6.68(1H, s), 7.09(1H, d), 7.29(1H, t), 7.40–7.47(5H, m), 7.74–7.76(2H, m), 8.08–8.12(1H, m), 8.53(1H, d), 8.86(1H, m), 9.18(1H, t). |
| 3-51 | 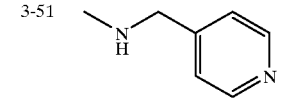 | HCl | pow. | NMR: (CDCl₃); 2.70(3H, s), 4.75(2H, br), 6.56(1H, s), 6.97(1H, d), 7.2–7.7(5H, m), 7.9–8.0(4H, m), 8.60(2H, br), 9.13(1H, br). |
| 3-52 | 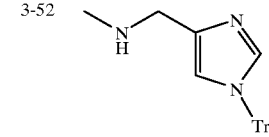 | — | amo. | NMR: (DMSO-d₆); 2.62(3H, s), 4.45(2H, br), 6.35(1H, s), 6.50–6.53(1H, m), 6.81(1H, d), 6.95(1H, d), 7.11–7.43(22H, m), 7.68–7.70(2H, m). |
| 3-53 | 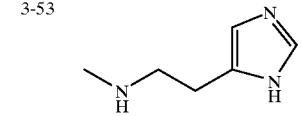 | HCl | amo. | NMR: (DMSO-d₆); 2.49(3H, s), 2.83–2.87(2H, m), 3.40–3.55(5H, m), 6.53(1H, s), 7.07(1H, d), 7.26–7.30(1H, m), 7.38–7.49(6H, m), 7.74–7.76(2H, m), 8.50(1H, t), 9.02(1H, d). |
| 3-54 | 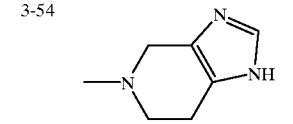 | HCl | pow. | NMR: (DMSO-d₆); 2.4–2.5(2H, br), 2.51(3H, s), 2.7–2.9(2H, m), 2.6–2.7(1H, m), 3.87(2H, s), 4.6–4.9(3H, m), 6.94(1H, s), 7.15(1H, d), 7.3–7.8(8H, m), 8.98(1H, d). |
| 3-55 | 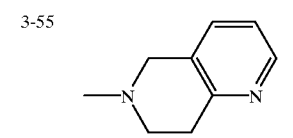 | HCl | pow. | NMR: (DMSO-d₆); 2.53(3H, s), 3.10–3.20(2H, m), 3.94(2H, br), 4.86(2H, br), 6.93(1H, s), 7.14–7.17(1H, m); 7.32–7.36(1H, m), 7.40–7.49(5H, m), 7.66–7.81(4H, m), 8.67–8.70(1H, m). |
| 3-56 | 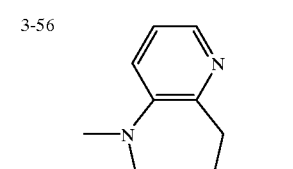 | — | pow. | NMR: (DMSO-d₆); 1.42(1H, br), 1.82(4H, br), 2.33(1H, br), 2.67(1H, br), 2.93(3H, br), 4.62(1H, br), 6.69(1H, s), 7.03–7.78(11H, m), 8.25(1H, d). |

TABLE 3-continued

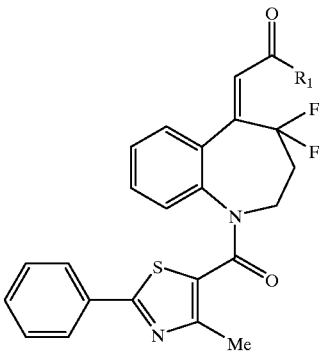

| Ex. | R₁ | Sal. | For. | |
|---|---|---|---|---|
| 3-57 | —N(piperazine)N—CH₂CH₂—O—CH₂CH₂—OH | 2HCl | pow. | NMR: (DMSO-d₆); 2.51(3H, s), 2.8–3.9(14H, m), 4.0–4.2(1 H, br), 4.40(1H, d), 4.8–5.0(1H, br), 6.80(1H, s), 7.15(1 H, d), 7.3–7.5(5H, m), 7.64(1H, d), 7.73(2H, d), 11.13( 1H, br). |
| 3-58 | —N(piperazine)N—CH₂CH₂—N(morpholine) | 3HCl | pow. | NMR: (DMSO-d₆); 2.50(3H, s), 2.7–5.0(24H, m), 6.80(1H, s), 7.15(1H, d), 7.3–7.6(5H, m), 7.66(1H, d), 7.73(2H, d). |
| 3-59 | —N(piperazine)N—CH₂CH₂—NMe₂ | 2HCl | pow. | NMR: (CDCl₃); 2.60(3H, s), 2.95(6H, s), 3.0–3.7(6H, br), 3.85 (4H, d), 4.02(2H, br), 4.97(1H, br), 6.39(1H, s), 7.01(1H, d), 7.2–7.5(6H, m), 7.72(2H, d), 12.36(1H, br). |
| 3-60 | —N(piperidine)-NMe₂ | 2HCl | pow. | NMR: (DMSO-d₆); 2.08–2.11(2H, m), 2.52(3H, s), 3.16(1H, br), 3.40–3.45(1H, m), 4.49–4.53(1H, m), 6.80(1H, s), 7.13 (1H, d), 7.30–7.34(1H, m), 7.41–7.49(4H, m), 7.57–7.59(1 H, m), 7.74–7.76(2H, m). |
| 3-61 | —N(piperidine)-C(=O)-N(OMe)(Me) | — | yamo. | NMR: (CDCl₃); 1.67–1.86(3H, m), 2.63(3H, s), 2.80–2.92(2H, m), 3.14–3.24(4H, m), 3.71(3H, s), 3.94–3.97(1H, m), 4.5 8(1H, br), 6.34(1H, s), 6.97(1H, d), 7.23–7.24(1H, m), 7.3 5–7.40(4H, m), 7.45–7.47(1H, m), 7.69–7.70(2H, m). |
| 3-62 | —N(piperidine)=CH—CO₂Et | — | amo. | NMR: (CDCl₃); 1.28(3H, t), 1.59(3H, s), 2.3–2.4(2H, m), 2.64 (3H, m), 3.61(1H, br), 4.16(2H, q), 5.75(1H, d), 6.36(1H, d), 6.99(1H, d), 7.3–7.5(6H, m), 7.69(2H, d). |
| 3-63 | —N(piperidine)-CH₂-CO₂Et | — | amo. | NMR: (CDCl₃); 1.2–1.3(6H, m), 1.6–1.7(2H, br), 2.0–2.1(1H, m), 2.2–2.7(8H, m), 3.13(2H, t), 3.88(1H, d), 4.13(2H, q), 4.61(1H, d), 6.32(1H, s), 6.97(1H, d), 7.2–7.5(6H, m), 7.7 0(2H, d). |
| 3-64 | —N(piperazine)N—CH₂CH₂CH₂—CO₂Et | HCl | pow. | NMR: (DMSO-d₆); 1.20(3H, t), 1.92(2H, b), 2.4 9(3H, s), 4.08(2H, q), 6.77(1H, s), 7.15(1 H, d), 7.34(1H, t), 7.4–7.5(4H, m), 7.61(1 H, d), 7.72(2H, d). |
| 3-65 | —N(piperazinone)NH | — | amo. | NMR: (CDCl₃); 2.63(3H, s), 3.4–3.5(2H, m), 3. 8–3.9(1H, br), 4.3–4.4(2H, m), 6.1–6.2(1H, m), 6.32(1H, d), 7.00(1H, t), 7.3–7.5(6H, m), 7.6–7.7(2H, m). |

TABLE 3-continued

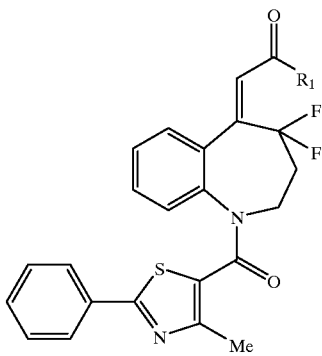

| Ex. | R₁ | Sal. | For. | |
|---|---|---|---|---|
| 3-66 | -N(piperazine)-CH₂CONHMe₂ | HCl | pow. | NMR: (DMSO-d₆); 2.51(3H, s), 2.92(3H, s), 2.95(3H, s), 4.39(2H, s), 6.81(1H, s), 7.15(1H, d), 7.31–7.36(1H, m), 7.41–7.48(4H, m), 7.62–7.65(1H, m), 7.72–7.75(2H, m). |
| 3-67 | MeHN-(piperazine)-CH₂CH₂OH | HCl | pow. | NMR: (DMSO-d₆); 2.20(1H, br), 2.66(1H, m), 3.06(2H, br), 3.15–3.25(2H, m), 3.33(2H, s), 3.52(1H, br), 3.76(2H, d), 4.82(1H, m), 5.32(1H, br), 6.51(0.5H, s), 6.71(0.5H, s), 7.07(0.5H, d), 7.15(0.5H, d), 7.31(1H, m), 7.39–7.53(4H, m), 7.75(2H, d), 9.31(0.5H, br), 9.71(0.5H, br), 10.51(1H, br). |
| 3-68 | Me-piperidine-C(O)N(Et)CH₂CO₂Et | — | amo. | NMR: (CDCl₃); 0.88(3H, t), 1.09(1H, t), 1.19–1.32(7H, m), 1.60(4H, m), 1.77–1.82(3H, m), 2.63(3H, s), 2.79(1H, m), 3.22(1H, m), 3.37–3.52(2H, m), 3.94–4.06(3H, m), 4.16(1H, q), 4.24(1H, q), 6.33(1H, s), 6.96(1H, d), 7.24(1H, m), 7.34–7.46(5H, m), 7.69(2H, m). |
| 3-69 | Me-piperidine-C(O)N(Me)CH₂CH₂CO₂Et | — | amo. | NMR: (CDCl₃); 1.23–1.29(4H, m), 1.57(3H, s), 1.68–1.82(3H, m), 2.55–2.61(3H, m), 2.63(3H, s), 2.85–2.95(2H, m), 3.09(2H, s), 3.19(1H, m), 3.55–3.70(2H, m), 3.96(1H, m), 4.06–4.19(2H, m), 4.57(1H, m), 6.33(1H, s), 6.96(1H, d), 7.23(1H, m), 7.35–7.52(5H, m), 7.69(2H, m). |
| 3-70 | Me-piperidine-C(O)NHCH₂CO₂Et | — | amo. | NMR: (CDCl₃); 1.27(3H, t), 1.6–1.8(2H, m), 1.8–2.0(2H, m), 2.4–2.5(2H, m), 2.63(3H, s), 2.8–2.9(1H, br), 3.19(1H, t), 3.95(1H, d), 4.03(2H, d), 4.22(2H, q), 4.54(1H, b), 4.97(1H, b), 6.00(1H, b), 6.32(1H, s), 6.97(1H, d), 7.3–7.5(6H, m), 7.69(2H, d). |
| 3-71 | Me-piperidine-CH₂CH₂CO₂Et | — | yamo. | NMR: (CDCl₃); 1.16–1.29(5H, m), 1.69–1.78(2H, m), 2.30–2.35(2H, m), 2.60–2.68(4H, m), 3.85–3.90(1H, m), 4.13(2H, q), 4.58–4.62(1H, m), 6.32(1H, s), 6.97(1H, d), 7.21–7.27(1H, m), 7.34–7.47(5H, m), 7.68–7.71(2H, m). |
| 3-72 | Me-piperidine-C(O)N(Me)CH₂CO₂Et | — | amo. | NMR: (CDCl₃); 1.2–1.3(3H, m), 1.7–1.8(3H, m), 2.63(3H, s), 2.7–2.8(1H, br), 3.13(3H, s), 3.2–3.3(1H, m), 3.9–4.0(1H, m), 4.1–4.3(4H, m), 6.33(1H, s), 6.96(1H, d), 7.3–7.5(6H, m), 7.70(2H, d). |
| 3-73 | Me-piperidine-C(O)CH₂CO₂Et | — | amo. | NMR: (CDCl₃); 1.24–1.32(4H, m), 1.88–1.94(2H, m), 2.63(3H, s), 3.16–3.23(1H, m), 3.50(2H, s), 3.90–3.95(1H, m), 4.19(2H, q), 6.31(1H, s), 6.98(1H, d), 7.23–7.28(1H, m), 7.34–7.45(5H, m), 7.68–7.71(2H, m). |
| 3-74 | Me-piperidine-NHC(O)CH₂CO₂Et | — | amo. | NMR: (CDCl₃); 1.28(3H, t), 1.4–1.5(2H, m), 1.99(2H, d), 2.63(3H, s), 4.20(2H, q), 6.32(1H, s), 6.98(1H, d), 7.2–7.5(6H, m), 7.69(2H, d). |

TABLE 3-continued

| Ex. | R₁ | Sal. | For. | NMR |
|---|---|---|---|---|
| 3-75 | N-methylpiperidin-4-yl-O-CH₂-CO₂Et | — | yamo. | NMR: (CDCl₃); 1.24–1.31(4H, m), 2.63(3H, s), 4.11(2H, s), 4.21(2H, q), 6.33(1H, s), 6.96–6.99(1H, m), 7.21–7.27(1H, m), 7.34–7.40(4H, m), 7.44–7.46(1H, m), 7.68–7.71(2H, m). |
| 3-76 | N-methylpiperidin-4-yl-CH₂-O-CH₂-CO₂Et | — | yamo. | NMR: (CDCl₃); 1.25–1.31(4H, m), 2.63(3H, s), 3.06–3.12(1H, m), 3.39–3.41(1H, m), 4.04–4.25(4H, m), 6.33(1H, s), 6.96–6.99(1H, m), 7.20–7.26(1H, m), 7.36–7.46(5H, m), 7.68–7.71(2H, m). |
| 3-77 | N-methylpiperidin-4-yl-CH=CH-CO₂Et | — | amo. | NMR: (CDCl₃); 1.29(3H, t), 2.63(3H, s), 4.19(2H, q), 5.81(1H, d), 6.32(1H, s), 6.84–6.92(1H, m), 6.98(1H, d), 7.22–7.28(1H, m), 7.35–7.39(4H, m), 7.44–7.46(1H, m), 7.68–7.71(2H, m). |
| 3-78 | N-methylpiperazin-1-yl-C(Me)₂-CO₂Et | HCl | pow. | NMR: (CDCl₃); 1.32(3H, t), 1.89(6H, s), 2.66(3H, s), 2.7–4.0(3H, m), 4.28(2H, q), 4.73(1H, d), 6.34(1H, s), 7.00(1H, s), 7.3–7.5(6H, m), 7.73(2H, d). |
| 3-79 | N-methylpiperazin-1-yl-cyclopropyl | HCl | pow. | NMR: (CDCl₃); 0.93(2H, m), 1.60(2H, m), 2.4–2.7(5H, m), 2.9–3.2(2H, m), 3.5–3.7(4H, m), 3.9–4.3(4H, m), 4.69(1H, d), 6.39(1H, s), 7.02(1H, d), 7.3–7.5(6H, m), 7.72(2H, d). |
| 3-80 | N-methylpiperazin-1-yl-CH(Me)-CO₂Et | HCl | pow. | NMR: (CDCl₃); 1.33(3H, t), 1.6–1.9(4H, m), 2.3–2.6(1H, br), 2.64(3H, s), 3.42(4H, br), 4.02(2H, br), 4.28(2H, q), 4.75(1H, br), 6.33(1H, s), 6.99(1H, d), 7.3–7.5(6H, m), 7.69(2H, d). |
| 3-81 | N-methylpiperazin-1-yl-CH₂CH₂-CO₂Et | 2HCl | pow. | NMR: (DMSO-d₆); 1.21(3H, t), 2.4–2.6(4H, m), 2.97(4H, m), 3.23(1H, br), 3.3–3.6(4H, m), 4.11(2H, q), 4.42(1H, d), 6.80(1H, s), 7.14(1H, d), 7.3–7.5(5H, m), 7.64(1H, br), 7.73(2H, d), 11.85(1H, br). |
| 3-82 | N-methylpiperidin-4-yl-NH-C(=O)-CH₂CH₂-CO₂Et | — | amo. | NMR: (CDCl₃); 1.25(3H, t), 1.39(2H, m), 1.97(2H, br), 2.45(3H, t), 2.63–2.68(6H, m), 3.22(1H, m), 3.87(1H, m), 4.02(1H, m), 4.14(2H, q), 4.55(1H, br), 5.63(1H, d), 6.32(1H, s), 6.98(1H, d), 7.36–7.40(6H, m), 7.69–7.70(2H, m). |
| 3-83 | N-methylpiperidin-4-yl-N(Me)-C(=O)-CH₂-CO₂Et | — | amo. | NMR: (CDCl₃); 1.26–1.30(4H, m), 1.36–1.45(4H, m), 1.61(3H, s), 1.98(1H, br), 2.63(3H, s), 2.88(1H, m), 3.21–3.30(2H, m), 3.85(1H, br), 4.02(1H, m), 4.19(2H, q), 4.50(1H, br), 6.32(1H, s), 6.57(1H, br), 6.98(1H, d), 7.34–7.45(5H, m), 7.69(2H, d). |

TABLE 3-continued

[Structure: a benzazepine core with gem-difluoro group, connected via an exocyclic alkene to CH-C(=O)-R₁; the benzazepine nitrogen bears a 2-phenyl-4-methylthiazole-5-carbonyl group]

| Ex. | R₁ | Sal. | For. | NMR |
|---|---|---|---|---|
| 3-84 | [1-methylpiperidin-4-yl-C(=O)-NH-CH₂CH₂-CO₂Et] | — | amo. | NMR: (CDCl₃); 1.27(3H, t), 1.61–1.71(6H, m), 1.80–1.93(2H, m), 2.31(1H, m), 2.52(2H, t), 2.63(3H, s), 2.79(1H, m), 3.16(1H, m), 3.51(2H, q), 3.94(1H, d), 4.13–4.18(2H, m), 4.55(1H, m), 6.18(1H, m), 6.32(1H, s), 6.97(1H, d), 7.22(1H, m), 7.34–7.69(5H, m), 7.70(2H, m) |
| 3-85 | [1-methylpiperidin-4-yl-N(Me)-CH₂-CONH₂] | — | pow. | NMR: (CDCl₃); 1.4–1.5(2H, m), 1.7–1.8(2H, m), 2.33(3H, s), 3.06(3H, s), 3.94(1H, d), 4.70(1H, d), 6.33(1H, s), 6.99(1H, d), 7.3–7.5(6H, m), 7.69(2H, d). |
| 3-86 | [1-methylpiperidin-4-yl-CH₂CH₂-C(=O)-NH-CH₂CH₂-NMe₂] | HCl | pow. | NMR: (DMSO-d₆); 0.96–1.15(1H, m), 1.47(3H, m), 1.68–1.72(1H, m), 2.14(2H, m), 2.52(3H, s), 2.75(3H, s), 2.77(3H, s), 3.07–3.13(4H, m), 3.87(3H, m), 4.33–4.37(1H, m), 6.78(1H, s), 7.12(1H, d), 7.29–7.33(1H, m), 7.40–7.47(4H, m), 7.52–7.54(1H, m), 7.74–7.77(2H, m), 8.20(1H, m). |
| 3-87 | [1-methylpiperidin-4-yl-CH₂CH₂-C(=O)-NH-CH₂CH₂-CO₂Et] | — | amo. | NMR: (CDCl₃); 1.16–1.29(5H, m), 2.18(2H, t), 2.52(2H, t), 2.63(3H, s), 3.48–3.54(2H, m), 4.15(2H, q), 6.32(1H, s), 6.96–6.98(1H, m), 7.21–7.26(1H, m), 7.34–7.46(5H, m), 7.68–7.71(2H, m). |
| 3-88 | [4-methylpiperazin-1-yl-CH₂CH₂CH₂-CONH₂] | HCl | pow. | NMR: (DMSO-d₆); 1.91(2H, m), 2.18(2H, m), 2.50(3H, s), 2.7–3.3(2H, m), 2.9–3.2(2H, m), 2.43(1H, d), 6.78(1H, s), 6.92(1H, s), 7.15(1H, d), 7.33(1H, t), 7.4–7.5(4H, m), 7.63(1H, d), 7.73(2H, d). |
| 3-89 | [4-methylpiperazin-1-yl-CH₂-C(=O)-NHMe] | HCl | pow | NMR: (DMSO-d₆); 2.51(3H, s), 2.67(3H, d), 4.00(2H, s), 6.78(1H, s), 7.14(1H, d), 7.31–7.36(1H, m), 7.41–7.48(4H, m), 7.62–7.64(1H, m), 7.72–7.74(2H, m) |
| 3-90 | [4-methylpiperazin-1-yl-CH₂-C(=O)-NH-CH₂-CO₂Et] | HCl | pow. | NMR: (DMSO-d₆); 1.19(3H, t), 2.51(3H, s), 3.34–3.41(2H, m), 4.00(2H, s), 4.07(2H, q), 6.78(1H, s), 7.14(1H, d), 7.30–7.36(1H, m), 7.41–7.48(4H, m), 7.62–7.65(1H, m), 7.72–7.74(2H, m). |
| 3-91 | [1-methylpiperidin-4-ylidene=N-O-CH₂-NMe₂] | HCl | pow | NMR: (DMSO-d₆); 2.53(3H, s), 2.83–2.87(6H, m), 6.86(1H, s), 7.12–7.15(1H, m), 7.29–7.33(1H, m), 7.42–7.45(4H, m), 7.58–7.60(1H, m), 7.74–7.76(2H, m). |

TABLE 4

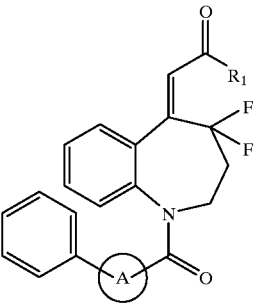

| Ex. | R₁ | A | Sal. | For. | |
|---|---|---|---|---|---|
| 4 | 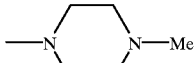 | 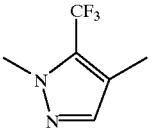 | HCl | pow. | m/z: 560(FAB, M⁺+1)<br>NMR: (CDCl₃); 2.42(1H, br), 2.85(3H, s), 3.27(1H, br), 3.5–3.7(4H, m), 4.0–4.2(3H, m), 4.73(1H, br), 5.02(1H, br), 6.34(1H, br), 6.9–7.1(2H, m), 7.3–7.6(8H, m), 13.37(1H, br). |
| 4-1 | 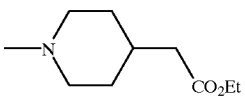 | 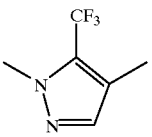 | — | amo. | m/z: 631(FAB, M⁺+1)<br>NMR: (CDCl₃); 1.28(3H, t), 1.19(2H, d), 2.07(1H, br), 2.2–2.3(2H, m), 2.6–2.7(1H, m), 3.16(1H, t), 3.90(1H, d), 4.14(2H, q), 4.60(1H, br), 6.32(1H, s), 6.92(1H, d), 7.00(1H, s), 7.2–7.5(8H, m). |
| 4-2 | 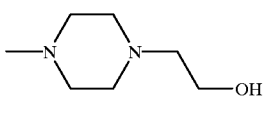 | 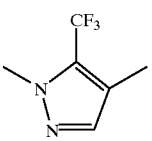 | HCl | pow. | m/z: 631(FAB, M⁺+1)<br>NMR: (DMSO-d₆); 3.00(1H, br), 3.2–3.3(3H, br), 3.5–3.7(3H, m), 3.80(3H, s), 4.08(1H, br), 4.42(1H, d), 5.38(1H, br), 6.82(1H, s), 7.01(1H, d), 7.09(1H, s), 7.3–7.4(3H, m), 7.44(1H, t), 7.5–7.6(3H, m), 7.63(1H, d), 10.65(1H, br). |
| 4-3 | 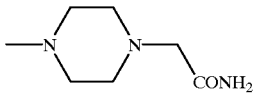 | 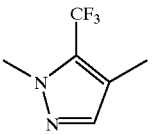 | HCl | amo. | m/z: 603(FAB, M⁺+1)<br>NMR: (DMSO-d₆); 4.00(2H, s), 6.82(1H, s), 7.02(1H, d), 7.09(1H, s), 7.37–7.71(9H, m), 8.08(1H, br). |
| 4-4 | 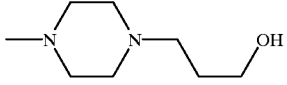 | 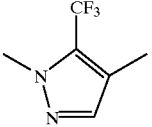 | HCl | amo. | m/z: 604(FAB, M⁺+1)<br>NMR: (DMSO-d₆); 1.85–1.89(2H, m), 2.46(2H, br), 6.83(1H, s), 7.02(1H, d), 7.10(1H, s), 7.37–7.64(8H, m). |
| 4-5 | 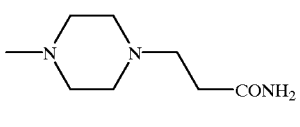 | 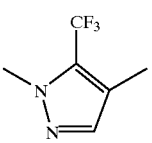 | HCl | oamo. | m/z: 617(FAB, M⁺+1)<br>NMR: (DMSO-d₆); 3.02(2H, m), 6.89–6.92(1H, m), 6.98(1H, s), 7.23–7.50(9H, m). |
| 4-6 | 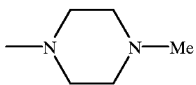 | 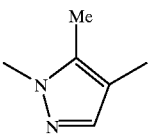 | HCl | pow. | m/z: 506(FAB, M⁺+1)<br>NMR: (DMSO-d₆); 2.45(3H, s), 2.79(3H, s), 2.8–3.2(4H, m), 3.4–3.7(3H, m), 4.0–4.2(1H, br), 4.4–4.5(1H, br), 4.8–4.9(1H, br), 6.23(1H, br), 6.75(1H, s), 7.16(1H, br), 7.3–7.6(7H, m), 7.67(1H, d), 11.16(1H, br). |
| 4-7 |  | 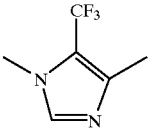 | — | amo. | m/z: 559(FAB, M⁺+1)<br>NMR: (CDCl₃); 2.43(1H, br), 2.45(2H, t), 2.51(2H, t), 2.53(1H, br), 3.40(1H, br), 3.83–3.99(4H, m), 4.90(1H, br), 6.35(1H, s), 6.99(1H, d), 7.16–7.54(9H, m). |

TABLE 4-continued

| Ex. | R₁ | A | Sal. | For. | |
|---|---|---|---|---|---|
| 4-8 | N-piperidinyl-CH₂-OAc | CF₃, methylimidazole | — | pow. | NMR: (CDCl₃); 1.10–1.32(2H, m), 1.65(3H, s), 1.72–1.81(2H, m), 1.89(1H, m), 2.05(3H, s), 3.67(1H, m), 3.06(1H, m), 3.92(2H, br), 4.67(1H, d), 6.67(1H, s), 6.96(1H, d), 7.16–7.22(3H, m), 7.28–7.35(1H, m), 7.39–7.52(5H, m). |
| 5-25 | N-piperidinyl-CH₂-CO₂H | Me, methylpyrazole | — | pow. | m/z: 603(FAB, M⁺+1) NMR: (CDCl₃); 1.2–1.4(2H, m), 1.83(2H, d), 2.0–2.1(1H, m), 2.3–2.5(3H, m), 2.70(2H, t), 3.17(2H, t), 3.91(1H, t), 4.62(1H, d), 4.98(1H, br), 6.33(1H, s), 6.92(1H, d), 7.00(1H, s), 7.2–7.5(8H, m). |
| 10-2 | N-piperidinyl-CH₂-OH | CF₃, methylimidazole | — | amo. | m/z: 575(FAB, M⁺+1) NMR: (CDCl₃); 1.64–1.85(4H, m), 2.30–2.75(4H, m), 3.06(1H, t), 3.31(1H, br); 3.45–3.51(2H, m), 4.24(1H, br), 4.67(2H, d), 4.89(1H, br), 6.29(1H, t), 6.96(1H, d, 7.16–7.54(9H, m). |

TABLE 5

| Ex. | R₁ | Sal. | For. | |
|---|---|---|---|---|
| 5 | N-piperidinyl-CH₂-CO₂H | — | pow. | m/z: 566(FAB, M⁺+1) NMR: (DMSO-d₆); 1.0–1.2(1H, m), 1.5–2.2(5H, m), 2.4–2.7(5H, m), 2.68(1H, br), 3.86(1H, d), 4.35(1H, d), 4.83(1H, br), 6.77(1H, s), 7.12(1H, d), 7.3–7.6(6H, m), 7.75(2H, d), 12.10(1H, s). |

TABLE 5-continued

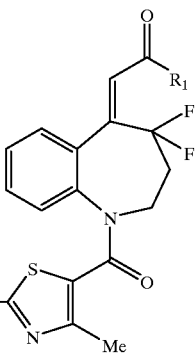

| Ex. | R₁ | Sal. | For. | |
|---|---|---|---|---|
| 5-1 | 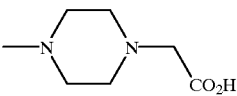 | — | pow. | m/z: 567(FAB, M⁺+1)<br>NMR: (DMSO-d₆); 2.41(2H, br), 2.52(3H, s), 3.08(2H, s), 3.50(4H, br), 6.77(1H, s), 7.12(1H, d), 7.29–7.32(1H, m), 7.41–7.49(4H, m), 7.55–7.57(1H, m), 7.74–7.76(2H, m). |
| 5-2 | 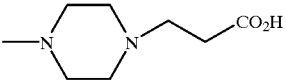 | — | amo. | m/z: 581(FAB, M⁺+1)<br>NMR: (CDCl₃); 2.57(2H, t), 2.64(3H, s), 2,80(2H, t), 3.64(1H, br), 6.31(1H, s), 7.01(1H, d), 7.3–7.5(6H, m), 7.69(2H, d). |
| 5-3 | 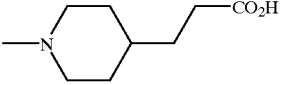 | — | pow. | m/z: 580(FAB, M⁺+1)<br>NMR: (DMSO-d₆); 0.98–1.18(1H, m), 1.46(2H, m), 1.67(2H, m), 2.23–2.25(2H, m), 2.52(3H, s), 3.85–3.89(1H, m), 4.33–4.37(1H, m), 6.78(1H, s), 7.12(1H, d), 7.28–7.33(1H, m), 7.40–7.47(4H, m), 7.54(1H, m), 7.74–7.77(2H, m), 12.02(1H, s). |
| 5-4 | 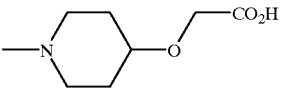 | — | amo. | m/z: 582(FAB, M⁺+1)<br>NMR: (DMSO-d₆); 2.52(3H, s), 3.86(2H, s), 6.79(1H, s), 7.12(1H, d), 7.28–7.33(1H, m), 7.40–7.45(4H, m), 7.53–7.56(1H, m), 7.74–7.76(2H, m). |
| 5-5 | 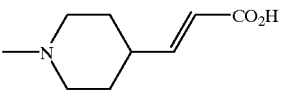 | — | amo. | m/z: 578(FAB, M⁺+1)<br>NMR: (CDCl₃); 2.60(3H, s), 5.77(1H, d), 6.33(1H, s), 6.76–6.84(1H, m), 6.95(1H, d), 7.19–7.42(6H, m), 7.66–7.68(2H, m). |
| 5-6 | 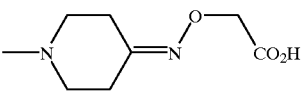 | — | amo. | m/z: 595(FAB, M⁺+1)<br>NMR: (DMSO-d₆); 2.31–2.32(2H, m), 2.51(3H, s), 2.57–2.63(2H, m), 3.58–3.60(4H, m) 4.22(2H, s), 6.73(1H, s), 7.11(1H, d), 7.30–7.33(1H, m), 7.40–7.45(4H, m), 7.53–7.54(1H, m), 7.72–7.73(2H, m). |
| 5-7 | 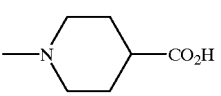 | — | pow. | NMR: (CDCl₃); 1.64–1.82(2H, m), 1.90–2.06(2H, m), 2.59(1H, m), 2.63(3H, s), 3.23(1H, m), 3.86(1H, d), 6.32(1H, br), 6.68(1H, d), 7.24(1H, m), 7.33–7.41(4H, m), 7.44(1H, m), 7.69(2H, m). |
| 5-8 | 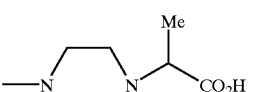 | — | amo. | NMR: (CDCl₃); 1.33(3H, d), 2.66(3H, s), 3.6–3.8(3H, m), 6.31(1H, s), 6.99(1H, d), 7.3–7.5(6H, m), 7.69(2H, d). |
| 5-9 | 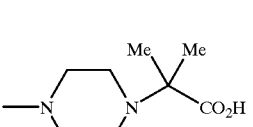 | — | pow. | NMR: (CDCl₃); 1.34(6H, s), 2.63(3H, s), 3.64(1H, br), 6.31(1H, s), 7.00(1H, d), 7.3–7.5(6H, m), 7.69(2H, d). |

TABLE 5-continued

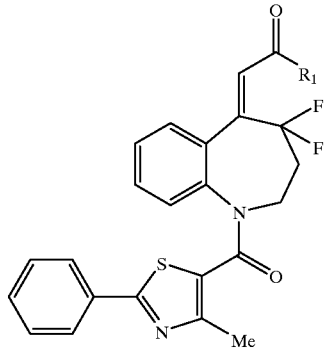

| Ex. | R₁ | Sal. | For. | |
|---|---|---|---|---|
| 5-10 | N-methylpiperazinyl-C(O)-CH₂-CO₂H | — | amo. | NMR: (CDCl₃); 2.64(3H, s), 6.33(1H, s), 7.01(1H, d), 7.3–7.5(6H, m), 7.69(2H, d). |
| 5-11 | N-methylpiperazinyl-(CH₂)₃-CO₂H | — | amo. | NMR: (DMSO-$d_6$); 1.6–1.7(2H, m), 2.5(3H, s), 6.77(1H, s), 7.12(1H, d), 7.31(1H, t), 7.4–7.5(4H, m), 7.56(1H, d), 7.75(2H, d). |
| 5-12 | N-methylpiperazinyl-CH₂-C(O)NH-CH₂CH₂-CO₂H | — | amo. | NMR: (DMSO-$d_6$); 2.51(3H, s), 2.95(2H, s), 6.79(1H, s), 7.12(1H, d), 7.29–7.33(1H, m), 7.40–7.42(4H, m), 7.56–7.58(1H, m), 7.73–7.76(2H, m), 7.90(1H, br). |
| 5-13 | N-methylpiperidin-4-yl-C(O)NH-CH₂-CO₂H | — | pow. | NMR: (CDCl₃); 1.4–2.0(4H, m), 2.3–2.5(2H, m), 2.62(3H, s), 2.8–2.9(1H, m), 3.19(1H, t), 3.93(3H, br), 4.51(1H, br), 4.97(1H, br), 6.35(1H, s), 6.49(1H, s), 6.96(1H, d), 7.3–7.5(6H, m), 7.68(2H, d). |
| 5-14 | N-methylpiperidin-4-yl-C(O)N(Me)-CH₂-CO₂H | — | pow. | NMR: (CDCl₃); 1.7–1.9(3H, m), 2.63(3H, s), 2.3–2.6(3H, m), 3.13(3H, s), 3.2–3.3(1H, m), 3.9–4.2(2H, m), 6.34(1H, s), 6.97(1H, d), 7.3–7.5(6H, m), 7.69(2H, d). |
| 5-15 | N-methylpiperidin-4-yl-NH-C(O)-CH₂-CO₂H | — | pow. | NMR: (CDCl₃); 1.46(2H, m), 1.98(2H, m), 2.62(3H, s), 2.90(1H, m), 3.88(1H, br), 4.04(1H, br), 4.49(1H, br), 6.34(1H, s), 6.98(1H, d), 7.3–7.5(6H, m), 7.68(2H, d). |
| 5-16 | N-methylpiperidin-4-yl-CH₂-O-CH₂-CO₂H | — | amo. | NMR: (CDCl₃); 1.77–1.89(3H, m), 2.63(3H, s), 3.06–3.15(1H, m), 3.36–3.40(2H, m), 3.88–3.92(1H, m), 4.06(2H, s), 4.59–4.63(1H, m) 6.34(1H, s), 6.97(1H, d), 7.22–7.46(6H, m), 7.68–7.70(2H, m). |
| 5-17 | N-methylpiperidin-4-yl-NH-C(O)-CH₂CH₂-CO₂H | — | amo. | NMR: (CDCl₃); 1.35–1.43(2H, m), 1.92–1.94(2H, m), 2.42(3H, t), 2.64(6H, br), 2.87(1H, br), 3.21(2H, t), 3.86(1H, m), 4.00(1H, m), 4.47(1H, m), 6.17(1H, m), 6.34(1H, s), 6.98(2H, d), 7.33–7.52(5H, m), 7.69(2H, d). |

TABLE 5-continued
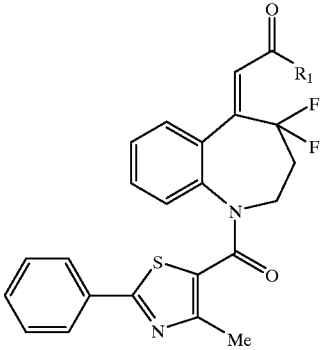
| Ex. | R₁ | | Sal. | For. | |
|---|---|---|---|---|---|
| 5-18 | 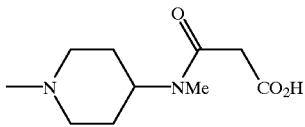 | | — | amo. | NMR: (CDCl₃); 1.19–1.47(10H, m), 1.94–1.97(2H, m), 2.61(3H, d), 2.92(1H, m), 3.46–3.51(2H, m), 3.88(1H, m), 4.03(1H, m), 4.51(1H, m), 6.35(1H, s), 6.92–7.00(2H, m), 7.33–7.52(5H, m), 7.65–7.89(2H, m). |
| 5-19 | 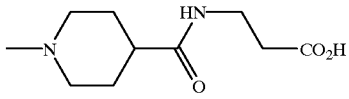 | | — | amo. | NMR: (CDCl₃); 1.64–1.83(4H, m), 2.34–2.37(4H, m), 2.62(3H, s), 2.78(1H, m), 3.16(1H, t), 3.48(2H, br), 3.57(1H, d), 4.51(1H, br), 6.34(1H, s), 6.49(1H, br), 6.97(1H, d), 7.23–7.27(1H, m), 7.33–7.52(5H, m), 7.68(2H, m). |
| 5-20 | 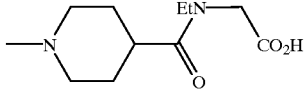 | | — | amo. | NMR: (CDCl₃); 1.22(3H, t), 1.60–1.94(4H, m), 2.45–2.65(4H, m), 2.78(1H, br), 2.88(1H, br), 3.07–3.30(2H, m), 3.32–3.52(2H, m), 3.86–4.10(3H, m), 4.35–4.75(2H, br), 6.35(1H, br), 6.96(1H, d), 7.24(1H, m), 7.32–7.41(4H, m), 7.45(1H, m), 7.69(2H, m). |
| 5-21 | 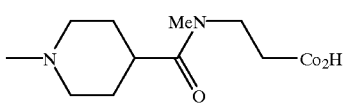 | | — | amo. | NMR: (CDCl₃); 1.76(4H, br), 2.55–2.62(2H, m), 2.63(3H, s), 2.86–2.94(2H, br), 3.08(2H, s), 3.18(1H, t), 3.53–3.75(2H, m), 3.93(1H, d), 4.55(1H, br), 6.34(1H, s), 6.98(1H, m), 7.24(1H, m), 7.33–7.41(4H, m), 7.47(1H, m), 7.69(2H, m). |
| 5-22 | 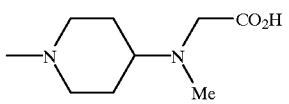 | | — | pow. | NMR: (CDCl₃); 1.5–1.7(2H, m), 2.0–2.2(2H, br), 2.60(3H, s), 2.6–2.8(4H, br), 3.22(1H, br), 3.5–3.7(1H, br), 4.02(1H, br), 4.71(1H, br), 6.36(1H, s), 6.96(1H, d), 7.2–7.5(6H, m), 7.69(2H, d). |
| 5-23 | 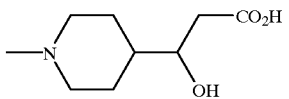 | | — | amo. | NMR: (CDCl₃); 1.26(2H, m), 1.62(2H, m), 2.61(3H, s), 6.33(1H, s), 6.96(1H, d), 7.21–7.26(1H, m), 7.34–7.38(4H, m), 7.43–7.46(1H, m), 7.67–7.69(2H, m). |
| 5-24 | 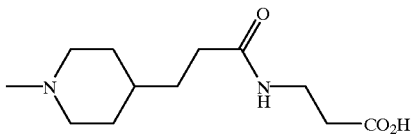 | | — | amo. | NMR: (DMSO-d₆); 1.43(2H, m), 2.36(2H, t), 2.51(3H, s), 3.18–3.24(2H, m), 6.77(1H, s), 7.10–7.13(1H, m), 7.27–7.33(1H, m), 7.39–7.46(4H, m), 7.52–7.54(1H, m), 7.74–7.76(2H, m), 7.88(1H, br), 12.17(1H, s). |

TABLE 6

| Ex. | A | Sal. | For. | |
|---|---|---|---|---|
| 7 | 1,5-dimethyl-4-ethyl-pyrazol-3-yl (Et, Me on pyrazole) | HCl | pow. | m/z: 520(FAB, M⁺+1)<br>NMR: (DMSO-d₆); 1.03(3H, t), 3.45(3H, s), 4.39–4.44(1H, m), 6.24(1H, s), 6.78(1H, s), 7.09(1H, d), 7.37–7.69(7H, m), 7.69–7.95(1H, m). |
| 7-1 | N-methylmorpholin-2-yl | HCl | amo. | m/z: 534(FAB, M⁺+1)<br>NMR: (DMSO-d₆); 0.74–0.76(3H, m), 3.34(3H, s), 4.06(1H, m), 4.39(1H, m), 6.23(1H, s), 6.79(1H, s), 7.06(1H, d), 7.36–7.55(7H, m), 7.67–7.69(1H, m). |
| 7-2 | 1-methyl-5-trifluoromethyl-imidazol-4-yl | HCl | amo. | m/z: 560(FAB, M⁺+1)<br>NMR: (DMSO-d₆); 2.72–2..86(4H, m) 2.94(2H, br), 3.16(2H, br), 3.35–4.00(4H, br), 4.23(1H, br), 4.43(1H, br), 4.75(1H, br), 6.39(1H, s), 6.92(1H, d), 7.25–7.40(4H, m), 7.44–7.66(5H, m), 7.91(1H, s), 11.20(1H, br). |
| 7-3 | 1-methyl-pyrazol-4-yl | HCl | oamo. | NMR: (DMSO-d₆); 3.34(3H, s), 4.02(1H, br), 4.37–4.41(1H, m), 4.80(1H, br), 6.67(1H, br), 6.73(1H, s), 7.25(1H, d), 7.34(1H, m), 7.45–7.50(3H, m), 7.58(1H, t), 7.66–7.69(2H, m), 7.72–7.75(1H, m). |
| 7-4 | 1-methyl-pyrazol-3-yl | HCl | yamo. | NMR: (DMSO-d₆); 3.34(3H, s), 4.37–4.41(1H, m), 6.43(1H, br), 6.45(1H, s), 7.06–7.09(1H, m), 7.28–7.35(2H, m), 7.40–7.45(5H, m), 7.61–7.63(1H, m), 8.36(1H, s). |
| 7-5 | 1,5-dimethyl-pyrazol-3-yl | HCl | amo. | NMR: (DMSO-d₆); 2.73(3H, s), 3.34(3H, s), 3.99–4.06(2H, m), 4.35–4.40(1H, m), 6.13(1H, br), 6.34(1H, br), 7.06–7.16(3H, m), 7.39–7.57(6H, m). |
| 7-6 | 1,3,4,5-tetramethyl-pyrazol-3-yl | HCl | yamo. | NMR: (DMSO-d₆); 2.07(3H, s), 2.15(3H, s), 3.40(3H, s), 4.02–4.04(2H, m), 4.35–4.39(2H, m), 6.18(1H, s), 7.00–7.50(9H, m). |
| 7-7 | 3,4-dimethyl-5-trifluoromethyl-thiophen-2-yl | HCl | pow. | NMR: (DMSO-d₆); 2.66–2.85(5H, br), 3.04(1H, m), 3.22(1H, m), 3.37–3.50(3H, m), 4.05(1H, m), 4.37(1H, m), 4.78(1H, m), 6.44(1H, s) 6.60(1H, s), 7.20(2H, d), 7.38–7.46(4H, m), 7.52(1H, t), 7.60(1H, t), 7.73(1H, d), 10.76(1H, br). |
| 7-8 | 2,4-dimethyl-5-methyl-oxazolyl | — | amo. | NMR: (CDCl₃); 2.22–2.30(4H, m), 2.47(3H, br), 2.55–2.85(2H, m), 3.33(1H, m), 3.42–3.54(2H, m), 3.65(2H, br), 4.91(1H, m), 6.22(1H, s), 7.02(1H, d), 7.22–7.36(5H, m), 7.38–7.50(3H, m). |

TABLE 6-continued

| Ex. | A | Sal. | For. | |
|---|---|---|---|---|
| 7-9 | 2,4-dimethyl-5-methylthiazole | — | amo. | NMR: (CDCl₃); 2.08(4H, m), 2.23(3H, s), 2.33(4H, br), 2.55(3H, s), 3.29(3H, br), 3.38–3.68(3H, m), 4.88(1H, m), 6.06(1H, s), 7.02–7.66(9H, m). |
| 7-10 | 1,5-dimethylpyrazole | HCl | amo. | NMR: (DMSO-d₆); 3.34(3H, s), 4.41–4.43(1H, m), 5.68(1H, s), 6.79(1H, s), 7.14(1H, d), 7.32–7.37(1H, m), 7.42–7.55(7H, m), 7.63–7.65(1H, m). |
| 7-11 | 1,3-dimethylpyrazole | HCl | amo. | NMR: (DMSO-d₆); 2.81(3H, s), 3.44(3H, s), 4.06–4.11(1H, m), 4.42–4.47(1H, m), 5.47(1H, s), 6.78(1H, s), 7.13(1H, d), 7.39–7.49(7H, m), 7.62–7.65(1H, m). |
| 7-12 | 3,4-dimethylisoxazole | — | amo. | NMR: (CDCl₃); 2.22(3H, s), 2.34(3H, s), 2.38–2.50(5H, m), 2.67(1H, br), 3.54(3H, br), 3.60–3.80(2H, br), 6.47(1H, d), 7.02(1H, m), 7.20(2H, br), 7.25–7.60(4H, br), 7.62–7.90 2H, m). |

TABLE 7

| Ex. | R₂ | R₃ | Sal. | For. | |
|---|---|---|---|---|---|
| 7-13 | —H | —H | HCl | pow. | NMR: (DMSO-d₆); 2.39(1H, br), 2.67(1H, m), 3.0–3.6(9H, m), 3.7–4.0(4H, m), 4.84(1H, d), 6.59(1H, s), 7.27(1H, s), 7.29(1H, s), 7.4–7.6(6H, m), 7.84(2H, m), 8.64(1H, t), 11.16(1H, br). |

TABLE 7-continued

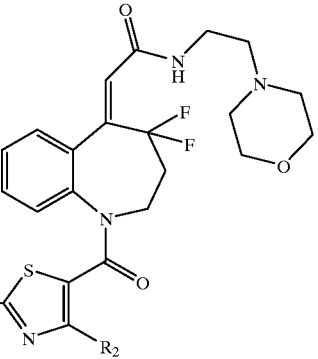

| Ex. | R₂ | R₃ | Sal. | For. |  |
|---|---|---|---|---|---|
| 7-14 | —Me | —H | HCl | pow. | NMR: (CDCl₃); 2.0–2.5(2H,br), 2.66(3H,s), 2.92–2.94(2H, m), 3.24(2H,br) 3.52–3.55(2H, m), 3.82(2H,br), 3.97–4.0(2H, m),4.24–4.3(2H, m), 6.44(1H, s), 6.93(1H, d), 7.2–7.4(4H, m), 7.56(1H, d), 7.78(2H, d), 8.48(1H, br), 12.49(1H, br). |
| 7-15 | —Et | —H | HCl | pow. | NMR: (DMSO-d₆); 1.23(3H, t), 2.40(1H, br), 2.67(1H, br), 2.87(2H, m), 3.0–3.25(4H, m), 3.3–3.7(5H, m), 3.8–4.0(4H, m), 5.87(1H, br), 6.63(1H, s), 7.04(1H, d), 7.2–7.5(5H, m), 7.79(2H, m), 8.67(1H, t), 11.39(1H, br). |
| 7-16 | —OMe | —H | HCl | pow. | NMR: (DMSO-d₆); 2.45(2H, m), 3.05–3.25(4H, m), 3.3–3.6(5H, m), 3.71 (3H, s), 3.75–4.0(4H, m), 4.82(1H, br), 6.48(1H, s) 7.06(1H, d), 7.25–7.55(5H, m), 7.83(2H, m), 8.56(1H, t), 11.08(1H, br). |
| 7-17 | —CF₃ | —H | HCl | pow. | NMR: (CDCl₃); 2.4–2.5(1H, br), 2.9–3.0(1H, br), 3.3–3.4(4H, m), 3.5–3.6(2H, m), 3.84(2H, d), 3.9–4.1(2H, m), 4.2–4.3(2H, m), 4.9–5.0(1H, br), 6.46(1H, s), 6.97–6.99(1H, m), 7.2–7.5(5H, m), 7.79–7.81 (2H, m), 8.52(1H, br,), 12.56(1H, br). |
| 7-18 | —Me | 2-Me | HCl | pow. | NMR: (DMSO-d₆); 2.32(3H, s), 2.39(1H, m), 2.53(3H, s), 2.89(1H, m), 3.05–3.25(4H, m), 3.4–3.6(5H, m), 3.7–4.0(4H, m), 4.86(1H, br), 6.47(1H, s), 7.11(1H, d), 7.2–7.6(7H, m), 8.64(1H, t), 11.11(1H, br). |
| 7-19 | —Me | 3-Me | HCl | pow. | NMR: (DMSO-d₆); 2.33(3H, s), 2.41(1H, m), 2.48(3H, s), 2.68(1H, m), 3.05–3.25(5H, m), 3.4–3.6(4H, m), 3.8–4.0(4H, m), 4.86(1H, br), 6.62(1H, s), 7.07(1H, d), 7.2–7.7(7H, m), 8.66(1H, t), 11.32(1H, br). |
| 7-20 | —Me | 4-Me | HCl | pow. | NMR: (DMSO-d₆); 2.32(3H, s), 2.39(1H, m), 2.48(3H, s), 2.67(1H, m), 3.05–3.25(5H, m), 3.4–3.65(4H, m), 3.75–4.0(4H, m), 4.86(1H, br), 6.40(1H, br), 6.61 (1H, s), 7.07(1H, d), 7.2–7.35(3H, m), 7.42(2H, m), 7.66(2H, d), 8.66(1H, t), 11.37(1H, br). |
| 7-21 | —Me | 2-CF₃ | HC | pow. | NMR: (DMSO-d₆); 2.41(1H, m), 2.50(3H, s), 2.8(1H, m), 3.0–3.25(5H, m), 3.5–3.7(4H, m), 3.75–4.0(4H, m), 4.87(1H, br), 6.41(1H, s), 7.09(1H, d), 7.30(1H, m), 7.35–7.55(3H, m), 7.70(2H, m), 7.85(1H, m), 8.67(1H, t), 11.28(1H, br). |
| 7-22 | —Me | 4-CF₃ | HCl | pow. | NMR: (DMSO-d₆); 2.51(3H, s) 3.1–3.2(4H, m), 3.4–3.6(4H, m), 3.79–3.85(2H, m), 3.93–3.97(2H, m), 6.64(1H, s), 7.10(1H, d), 7.26–7.45(3H, m), 7.78(2H, d), 8.01(2H, d), 8.64(1H, m), 11.06(1H, br). |
| 7-23 | —Me | 2-OMe | HCl | ypow. | NMR: (DMSO-d₆); 2.46(1H, br), 2.49(3H, s), 2.65(1H, br), 3.0–3.25(5H, m), 3.46(2H, d), 3.60(2H, br), 3.8–4.0(7H, m), 4.88(1H, br), 6.37(1H, s), 7.0–7.5(7H, m), 8.15(1H, m), 8.77(1H, t), 11.58(1H, br). |
| 7-24 | —Me | 3-OMe | HCl | pow. | NMR: (DMSO-d₆); 2.45(1H, br), 2.48(3H, s), 2.67(1H, br), 3.0–3.3(5H, m), 3.46(2H, d), 3.59(2H, m), 3.79(3H, s), 3.8–4.0(4H, m), 4.86(1H, br), 6.23(1H, br), 6.61(1H, s), 7.0–7.1(2H, m), 7.25–7.45(6H, m), 8.68(1H, t), 11.48(1H, br). |
| 7-25 | —Me | 4-OMe | HCl | ypow. | NMR: (DMSO-d₆); 2.43(1H, m), 2.47(3H, s), 2.67(1H, m), 3.05–3.25(5H, m), 3.46(2H, d), 3.58(2H, br), 3.79(3H, s), 3.8–4.0(4H, m), 4.86(1H, br), 6.07(1H, br), 6.59(1H, s), 6.97(2H, m), 7.07(1H, d), 7.29(1H, m) 7.4(2H, m), 7.70(2H, m), 8.66(1H, t), 11.34(1H, br). |

TABLE 7-continued

| Ex. | R₂ | R₃ | Sal. | For. | NMR |
|---|---|---|---|---|---|
| 7-26 | —Me | 2-F | HCl | ypow. | NMR: (DMSO-d₆); 2.42(1H, br), 2.50(3H, s), 2.67(1H, m), 3.05–3.25(5H, m), 3.47(2H, d), 3.59(2H, m), 3.8–4.0(4H, m), 4.87(1H, br), 6.35(1H, s), 7.11(1H, d), 7.25–7.6(6H, m), 8.10(1H, m), 8.73(1H, t), 11.35(1H, br). |
| 7-27 | —Me | 3-F | HCl | pow. | NMR: (DMSO-d₆); 2.41(1H, br), 2.66(1H, m), 3.05–3.25(5H, m), 3.35(3H, s), 3.47(2H, d), 3.56(2H, br), 3.80(2H, t), 3.95(2H, m), 6.67(1H, s), 7.08(1H, d), 7.25–7.65(7H, m), 8.63(1H, t), 10.98(1H, br). |
| 7-28 | —Me | 4-F | HCl | pow. | NMR: (DMSO-d₆); 2.40(1H, m), 2.49(3H, s), 2.70(1H, m), 3.05–3.25(4H, m), 3.3–3.65(5H, m), 3.75–4.0(4H, m), 4.87(1H, br), 6.64(1H, s), 7.07(1H, d), 7.2–7.35(3H, m), 7.43(2H, m), 7.84(2H, m), 8.67(1H, t), 11.37(1H, br). |
| 7-29 | —Me | 3-Cl | HCl | pow. | NMR: (DMSO-d₆); 2.40(1H, m), 2.49(3H, s), 2.75(1H, m), 3.0–3.25(4H, m), 3.4–3.7(5H, m), 3.75–4.0(4H, m), 4.86(1H, br), 6.67(1H, s), 7.08(1H, d), 7.29(1H, m), 7.35–7.55(4H, m), 7.74(1H, m), 7.81(1H, m), 8.66(1H, t), 11.27(1H, br). |

TABLE 8

| Ex. | A | R₃ | Sal. | For. | NMR |
|---|---|---|---|---|---|
| 6 | 2,4-dimethylthiazolyl | —H | — | pow. | NMR: (CDCl₃); 2.4–2.6(6H, m), 3.3–3.6(2H, m), 3.6–3.7(4H, m), 4.93(1H, br), 6.28(1H, s), 6.40(1H, br), 6.92(1H, br), 7.2–7.5(8H, m), 7.80(1H, br). |
| 7-30 | 2,5-dimethylthiazolyl | —H | — | amo. | NMR: (CDCl₃); 2.3–2.6(6H, m), 3.3–3.7(5H, m), 6.26(1H, s), 7.3–7.7(10H, m). |
| 7-31 | 3,5-dimethylisoxazolyl | —H | — | pow. | NMR: (CDCl₃); 2.5–3.3(6H, m), 3.3–3.6(4H, m), 3.6–3.7(4H, m), 6.30(1H, s), 6.58(1H, s), 7.03(1H, d), 7.2–7.5(6H, m), 7.64–7.67(2H, m). |

TABLE 8-continued

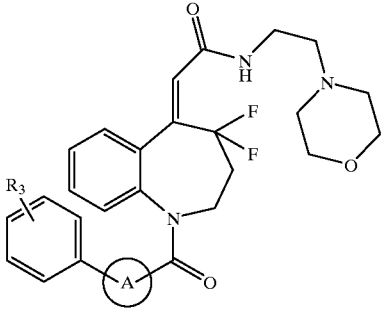

| Ex. | A | R₃ | Sal. | For. | |
|---|---|---|---|---|---|
| 7-32 | 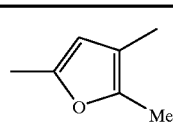 | —H | HCl | pow. | NMR: (CDCl₃); 2.52(3H, s), 2.92(2H, br), 3.22(2H, br), 3.5–3.54(2H, m), 3.8–3.82(2H, m), 3.99–4.00(2H, m), 4.25–4.28(2H, m), 5.36(1H, br), 6.39(1H, s). |
| 7-33 | 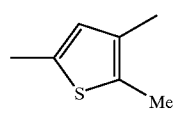 | —H | HCl | pow. | NMR: (DMSO-d₆); 3.11–3.21(4H, m), 3.35(3H, s), 3.46–3.57(4H, m), 3.76–3.83(2H, m), 3.94–4.06(2H, m), 6.45(1H, s), 6.57(1H, br), 6.97(1H, br), 7.25–7.40(8H, m), 8.68(1H, br), 10.92(1H, br). |
| 7-34 | 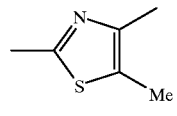 | —H | HCl | pow. | NMR: (DMSO-d₆); 2.3–2.8(6H, m), 3.0–3.25(4H, m), 3.35–3.65(4H, m), 3.75–4.0(4H, m), 4.87(1H, br), 6.38(1H, s), 6.92(1H, d), 7.15(1H, t), 7.27(1H, t), 7.35–7.5(5H, m), 8.63(1H, t), 11.18(1H, br). |
| 7-35 | 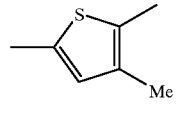 | —H | HCl | pow. | NMR: (DMSO-d₆); 2.31(3H, s), 3.0–3.2(4H, m), 3.3–3.6(6H, m), 3.75–3.8(2H, m), 3.94–4.04(2H, m), 6.49(1H, s), 7.02(1H, d), 7.2–7.5(8H, m), 8.60(1H, br), 10.80(1H, br). |
| 7-36 | 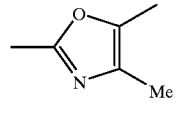 | —H | HCl | pow. | NMR: (CDCl₃); 2.53(3H, s), 2.6–2.7(3H, m), 3.20(2H, m), 3.47–3.49(2H, m), 3.79(2H, br), 3.99(2H, br), 4.2–4.3(2H, m), 6.31(1H, s), 7.00(1H, d), 7.2–7.5(6H, m), 7.66(1H, d), 8.34(1H, br), 12.56(1H, br). |
| 7-37 | 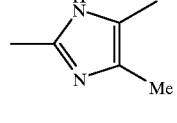 | —H | 2HCl | pow. | NMR: (DMSO-d₆); 2.50(3H, s), 3.1–3.2(4H, m), 3.46(2H, d), 3.57(2H, m), 3.79–3.85(2H, m), 3.94–4.0(2H, m), 6.39(1H, s), 7.2–7.5(8H, m), 7.96(1H, br), 8.68(1H, br), 11.18(1H, br). |
| 7-38 | 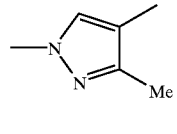 | —H | HCl | pow. | NMR: (CDCl₃; 2.50(3H, s), 2.7–3.0(2H, m), 3.1–3.3(2H, m), 3.4–3.6(2H, m), 3.7–3.8(2H, m), 3.9–4.3(4H, m), 6.36(1H, s), 6.56(1H, br), 7.01(1H, d), 7.3–7.5(6H, m), 7.61(1H, d), 8.38(1H, br), 12.42(1H, br). |
| 7-39 | 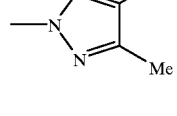 | —H | HCl | pow. | NMR: (DMSO-d₆); 2.50(3H, s), 3.1–3.2(4H, m), 3.3–3.7(6H, m), 3.78–3.83(2H, m), 3.96–3.99(2H, m), 6.54(1H, s), 6.87(1H, br), 7.1–7.6(7H, m), 8.71(1H, br), 10.92(1H, br). |
| 7-40 | 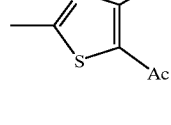 | —H | — | pow. | NMR: (CDCl₃); 2.41(3H, s), 2.4–2.6(6H, m), 3.3–3.8(7H, m), 5.03(1H, br), 5.96(1H, s), 7.1–7.6(7H, m), 7.91(2H, d). |

TABLE 8-continued

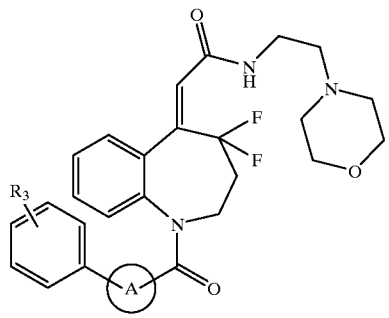

| Ex. | A | R₃ | Sal. | For. | |
|---|---|---|---|---|---|
| 7-41 | (1-methyl-4-methyl-3-SMe-pyrazole) | —H | — | pow. | NMR: (CDCl₃); 2.4–2.5(6H, m), 2.57(3H, s), 3.41(1H, br ), 3.72–3.40(4H, m), 6.17(1H, s), 6.26(1H, s), 6.40(1H, br), 7.2–7.6(8H, m). |
| 7-42 | (1-methyl-4-methyl-5-Me-pyrazole) | —H | HCl | pow. | NMR: (DMSO-d₆); 2.45(3H, s), 3.0–3.3(4H, m), 3.4–3.7 (5H, m), 3.8–3.9(2H, m), 3.9–4.0(2H, m), 6.28(1H, br), 6.55(1H, s), 7.10(1H, d), 7.3–7.6(7H, m), 8.62(1H, d), 10.94(1H, br). |
| 7-43 | (1-methyl-4-methyl-5-CF₃-pyrazole) | —H | HCl | pow. | NMR: (DMSO-d₆); 3.1–3.3(4H, m), 3.4–3.6(4H, m), 3.57–3.81(2H, m), 3.95–3.98(2H, m), 6.60(1H, s), 6.96(1H, d), 7.32–7.51(7H, m), 8.61(1H, br), 10.81(1H, br). |
| 7-44 | (1-methyl-4-methyl-3,5-diMe-pyrazole) | —H | — | amo. | NMR: (CDCl₃); 2.04(3H, br), 2.14(3H, br), 2.4–2.6(6H, m), 3.44–3.49(3H, m), 3.70–3.73(5H, m), 6.23(1H, s), 6.50(1H, br), 6.85(1H, br), 7.2–7.5(7H, m). |
| 7-45 | (1-methyl-4-methyl-imidazole) | —H | HCl | opow. | NMR: (DMSO-d₆); 3.0–3.2(4H, m), 3.3–3.6(4H, m), 3.7–3.8(2H, m), 3.9–4.0(2H, m), 6.42(1H, s), 7.3–7.6(10H, m), 8.57(1H, t), 10.82(1H, br). |
| 7-46 | (3,5-dimethyl-2-CHO-furan) | 4-Cl | HCl | pow. | NMR: (CDCl₃); 2.94(2H, br), 3.24(2H, br), 3.58(2H, br), 4.02(2H, br), 4.29(2H, br), 6.08(1H, s), 6.40(1H, s), 6.98(1H, d), 7.2–7.6(7H, m), 8.44(1H, br), 9.92(1H, s). |
| 7-47 | (3,5-dimethyl-2-CF₃-furan) | 4-Cl | HCl | pow. | NMR: (DMSO-d₆); 3.1–3.3(4H, m), 3.5–3.7(4H, m), 3.8–4.0(4H, m), 6.42(1H, s), 6.64(1H, s), 7.02(1H, d), 7.3–7.7(7H, m), 8.64(1H, br), 10.88(1H, br). |
| 7-48 | (3-methyl-2,5-diMe-furan) | 3-NO₂ | HCl | pow. | NMR: (DMSO-d₆); 2.42(3H, s), 3.0–3.3(4H, m), 3.4–3.6(4H, m), 3.7–3.8(2H, m), 3.9–4.0(2H, m), 6.65(1H, s), 7.07(1H, d), 7.29(1H, t), 7.4–7.5(2H, m), 7.63(1H, t), 7.84(1H, d), 8.1–8.2(2H, m), 8.62(1H, m), 10.83(1H, br). |

TABLE 9

| Ex. | B | Sal. | For. | |
|---|---|---|---|---|
| 7-49 | 3-methylpyridyl | 2HCl | pow. | NMR: (DMSO-d₆); 2.41(1H, m), 2.52(3H, s), 2.70(1H, m), 3.0–3.25(5H, m), 3.4–3.7(4H, m), 3.8–4.0(4H, m), 4.87(1H, br), 6.73(1H, s), 6.86(1H, br), 7.09(1H, d), 7.28(1H, m), 7.42(2H, m), 7.67(1H, m), 8.44(1H, d), 8.65–8.8(2H, m), 9.09(1H, s), 11.54(1H, br). |
| 7-50 | 4-methylpyridyl | 2HCl | pow. | NMR: (DMSO-d₆); 2.41(1H, m), 2.55(3H, s), 2.71(1H, m), 3.05–3.25(5H, m), 3.4–3.7(4H, m), 3.8–4.0(4H, m), 4.86(1H, br), 6.73(1H, s), 7.10(1H, d), 7.27(1H, m), 7.43(2H, m), 8.14(2H, m), 8.6–8.85(3H, m), 11.51(1H, br). |

TABLE 10

| Ex. | R₁ | Sal. | For. | |
|---|---|---|---|---|
| 8 | —OH | — | amo. | NMR: (CDCl₃; 1.57(2H, br), 1.75(1H, t), 2.66(3H, s), 4.65(2H, br), 6.19(1H, m), 6.93–7.00(1H, d), 7.21–7.30(1H, m), 7.34–7.52(5H, m). |
| 9 | N-methylpiperazinyl | 2HCl | pow. | NMR: (DMSO-d₆); 2.69(3H, s), 3.2–4.7(13H, m), 6.51(1H, br), 7.11(1H, d), 7.3–7.9(8H, m). |
| 9-1 | 4-(acetoxymethyl)piperidinyl | — | oil. | NMR: (CDCl₃); 1.6–1.8(2H, br), 2.02(3H, s), 2.0–2.5(3H, m), 2.63(3H, s), 2.96(2H, br), 3.3–3.4(1H, br), 3.90(2H, d), 4.78(1H, br), 6.18(1H, br), 6.92(1H, d), 7.2–7.4(6H, m), 7.68(2H, d). |
| 10-3 | 4-(hydroxymethyl)piperidinyl | HCl | pow. | NMR: (DMSO-d₆); 1.4–1.9(5H, m), 2.52(3H, s), 3.0–3.3(4H, m), 3.5–3.7(1H, br), 4.22(1H, br), 6.56(1H, br), 7.14(1H, d), 7.3–7.6(6H, m), 7.80(2H, d), 10.71(1H, br). |

TABLE 11

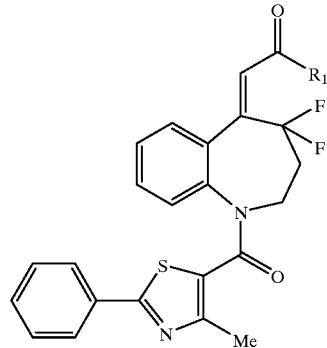

| Ex. | R₁ | Sal. | For. | |
|---|---|---|---|---|
| 9-2 | 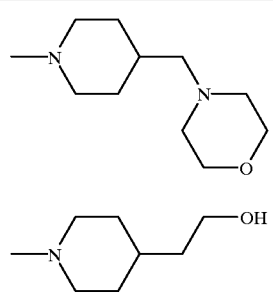 | HCl | pow. | NMR: (DMSO-d₆); 1.36(1H, br), 1.8–1.9(2H, m), 2.13(1H, br), 2.33(2H, br), 2.50(3H, s), 2.69(1H, t), 3.0–3.3(6H, m), 3.4–3.5 (2H, m), 3.8–4.0(6H, m), 4.34(1H, br), 4.82(1H, br), 6.79(1H, s), 7.12(1h, d), 7.3–7.6(6H, m), 7.75(2H, d), 10.36(1H, br). |
| 10 | 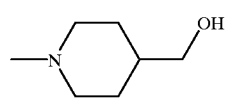 | — | pow. | m/z: 552(FAB, M⁺+1)<br>NMR: (DMSO-d₆); 1.67(3H, m), 2.52(3H, s), 3.84–3.88(1H, m), 4.33–4.35(1H, m), 6.77(1H, s), 7.12(1H, d), 7.28–7.33(1H, m), 7.40–7.54(5H, m), 7.74–7.76(2H, m). |
| 10-1 | 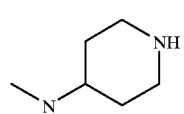 | — | amo. | m/z: 538(FAB, M⁺+1)<br>NMR: (CDCl₃); 1.27(2H, br), 1.41(1H, br), 1.59(3H, br), 1.73–1.84(3H, m), 2.63(3H, s), 2.64–2.70(2H, m), 3.11(1H, t), 3.46–3.58(2H, m), 3.92(1H, d), 4.65(1H, d), 6.33(1H, s), 6.98(1H, d), 7.23(1H, m), 7.34–7.42(4H, m), 7.45(1H, m), 7.68(1H, d), 7.70(1H, d). |
| 11 | 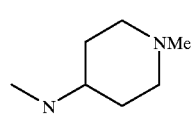 | HCl | pow. | NMR: (DMSO-d₆); 1.65–1.77(2H, m), 1.90–1.93(2H, m), 2.48(3H, s), 2.93–3.02(2H, m), 3.14(1H, br), 3.24–3.28(2H, m), 4.80(1H, br), 6.56(1H, s), 7.07(1H, d), 7.26–7.29(1H, m), 7.39–7.47(5H, m), 7.75(2H, d), 8.49(1H, d), 9.00(1H, br). |
| 12 | 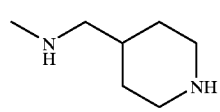 | — | pow. | NMR: (DMSO-d₆), 1.41–1.51(2H, m), 1.71–1.73(2H, m), 1.89–1.95(2H, m), 2.48(3H, s), 2.71–2.73(2H, m), 3.32(3H, s), 3.54–3.63(1H, m), 6.51(1H, s), 7.06(1H, d), 7.25–7.29(1H, m), 7.38–7.47(5H, m), 7.41–7.48(4H, m), 7.56–7.57(1H, m), 7.73–7.75(2H, m), 8.18(1H, d). |
| 13 |  | 2HCl | pow. | NMR: (DMSO-d₆); 1.32–1.40(2H, m), 1.75–1.83(3H, m), 2.49(3H, s), 2.77–2.80(2H, m), 3.00–3.06(2H, m), 3.22–3.26(2H, m), 6.54(1H, s), 7.07(1H, d), 7.28(1H, m), 7.39–7.49(6H, m), 7.73–7.75(2H, m), 8.47(1H, t). |
| 13-1 | 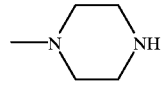 | HCl | pow. | NMR: (DMSO-d₆); 1.37–1.53(2H, m), 1.94–1.97(2H, m), 2(3H, s), 2.72–2.78(1H, m), 3.18–3.29(2H, m), 3.92–3.95(1H, m), 4.36(1H, br), 4.80(1H, br), 6.82(1H, s), 7.13(1H, d), 7.30–7.34(1H, m), 7.42–7.47(4H, m), 7.58(1H, d), 7.75–7.76(2H, m), 8.23(2H, br). |
| 13-2 | 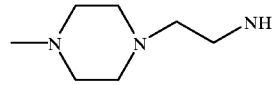 | — | pow. | NMR: (CDCl₃); 1.60(6H, br), 2.63(3H, s), 2.82–2.93(4H, m), 3.50(2H, t), 3.65(1H, br), 6.31(1H, s), 6.98(1H, d), 7.25–7.27(2H, br), 7.34–7.40(3H, m), 7.44(1H, m), 7.68–7.70(2H, m). |
| 13-3 |  | 2HCl | pow. | NMR: (DMSO-d₆); 2.49(3H, s), 3.24(1H, br), 3.50(5H, br), 3.90(4H, br), 6.65(1H, s), 7.08(1H, d), 7.27–7.31(1H, m), 7.39–7.48(4H, m), 7.77–7.79(2H, m), 8.60–8.63(1H, m), 9.66(2H, br). |

TABLE 11-continued

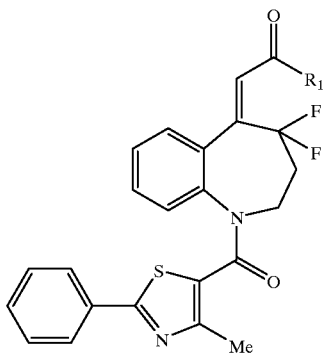

| Ex. | R₁ | Sal. | For. | |
|---|---|---|---|---|
| 13-4 | ⟨N-piperidine-NHMe⟩ | — | amo. | NMR: (CDCl₃); 1.8–1.9(1H, m), 2.45(3H, s), 2.63(3H, s), 3.18(1H, m), 3.87(1H, d), 6.33(1H, s), 6.97(1H, d), 7.3–7.4(5H, m), 7.45(1H, d), 7.69(2H, d). |
| 14 | ⟨N-piperidine=NOH⟩ | — | pow. | NMR: (DMSO-d₆); 2.27–2.31(2H, m), 2.53(3H, s), 3.59–3.63(2H, m), 6.85(1H, s), 7.13(1H, d), 7.30–7.34(1H, m), 7.41–7.49(4H, m), 7.56–7.60(1H, m), 7.75(1H, d), 10.54(1H, s). |
| 14-1 | ⟨N-piperidine=NOMe⟩ | — | pow. | NMR: (DMSO-d₆); 2.31 (2H, br), 2.42(2H, br), 2.52(3H, s), 3.60–3.65(3H, br), 3.75(3H, d), 6.84(1H, s), 7.13(1H, d), 7.30–7.34(1H, m), 7.41–7.49(4H, m), 7.58(1H, d), 7.74–7.76(2H, m). |
| 14-2 | ⟨N-piperidine=NOEt⟩ | — | pow. | NMR: (CDCl₃); 1.23–1.27(3H, m), 2.39–2.43(2H, m), 2.63(3H, d), 3.60–3.66(3H, br), 4.06–4.11(2H, m), 6.36(1H, s), 6.99(1H, d), 7.24–7.28(1H, m), 7.34–7.46(5H, m), 7.68–7.70(2H, m). |
| 14-3 | ⟨N-piperidine=N-O-CH₂CH₂-morpholine⟩ | 2HCl | pow. | NMR: (DMSO-d₆); 2.34–3.91(22H, m), 2.52(3H, s), 4.38–4.41(2H, m), 6.85(1H, s), 7.14(1H, d), 7.30–7.35(1H, m), 7.40–7.45(4H, m), 7.56–7.59(1H, m), 7.73–7.76(2H, m). |
| 14-4 | ⟨N-piperidine=N-O-CH₂-4-pyridyl⟩ | 2HCl | pow. | NMR: (DMSO-d₆); 2.53(3H, s), 3.66–3.68(2H, m), 5.30–5.36(2H, m), 6.85(1H, d), 7.15(1H, d), 7.33–7.36(1H, m), 7.43–7.48(4H, m), 7.56–7.60(1H, m), 7.75(2H, m), 7.90–7.94(2H, m), 8.85–8.86(2H, m). |
| 14-5 | ⟨N-piperidine=N-O-CH₂-3-pyridyl⟩ | HCl | yamo. | NMR: (DMSO-d₆); 2.32–2.34(1H, m), 2.52(3H, s), 3.63–3.65(2H, m), 5.23(2H, s), 6.85(1H, s), 7.12–7.15(1H, m), 7.30–7.35(1H, m), 7.40–7.47(4H, m), 7.56–7.59(1H, m), 7.73–7.77(2H, m), 7.92–7.97(1H, m), 8.37–8.42(1H, m), 8.80–8.84(2H, m). |
| 14-6 | ⟨N-piperidine=N-O-CH₂-2-pyridyl⟩ | HCl | amo. | NMR: (DMSO-d₆); 2.31–2.33(1H, m), 2.53(3H, s), 3.65(2H, br), 5.32(2H, s), 6.85(1H, d), 7.14(1H, d), 7.30–7.35(1H, m), 7.41–7.47(4H, m), 7.56–7.60(1H, m), 7.73–7.83(4H, m), 8.29–8.36(1H, m), 8.76–8.78(2H, m). |
| 14-7 | ⟨N-piperidine-CH(Me)-NOH⟩ | — | pow. | NMR: (DMSO-d₆); 1.72(3H, s), 2.52(3H, s), 2.65–2.73(1H, m), 3.89–3.93(1H, m), 4.36–4.40(1H, m), 6.80(1H, s), 7.12(1H, d), 7.29–7.34(1H, m), 7.41–7.47(4H, m), 7.53–7.56(1H, m), 7.74–7.77(2H, m). |

TABLE 11-continued

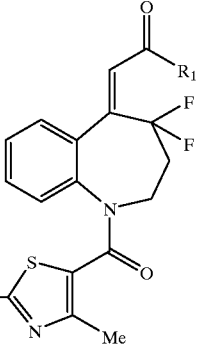

| Ex. | R₁ | Sal. | For. | |
|---|---|---|---|---|
| 14-8 | 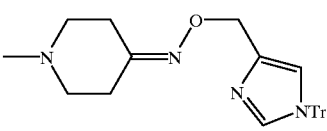 | — | amo. | NMR: (CDCl₃); 2.4–2.5(2H, m), 2.63(3H, s), 3.5–3.6(1H, m), 4.99(2H, d), 6.34(1H, s), 6.83(1H, s), 6.9–7.0(1 H, m), 7.0–8.0(22H, m), 7.69(2H, d). |
| 15 | 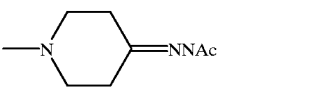 | — | pow. | m/z: 578(FAB, M⁺+1)<br>NMR: (DMSO-d₆); 2.50(3H, s), 3.32(3H, s), 3.5–3.8(3H, m), 6.86(1H, s), 7.14(1H, m), 7.32(1H, t), 7.4–7.5(4 H, m), 7.58(1H, t), 7.75(2H, d). |
| 16 | 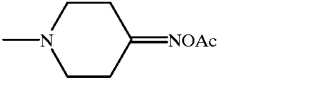 | — | pow. | NMR: (DMSO-d₆); 2.12(3H, d), 2.52(3H, s), 3.65–3.74(3H, m), 6.85(1H, br), 7.14(1H, d), 7.31–7.34(1H, m), 7.41–7.49(4H, m), 7.58–7.61(1H, m), 7.74–7.76(2H, m). |
| 16-1 | 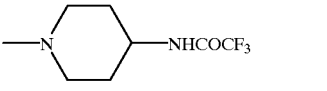 | — | amo. | NMR: (CDCl₃); 1.4–1.6(2H, m), 2.05(2H, d), 2.63(3H, s), 2.82(1H, t), 3.24(1H, t), 4.0–4.1(1H, br), 4.64(1H, br ), 6.33(1H, s), 7.00(1H, d), 7.3–7.5(6H, m), 7.69(2H, d). |
| 16-2 | 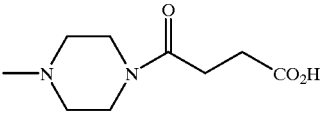 | — | pow. | NMR: (CDCl₃); 2.63(3H, s), 2.6–2.7(4H, m), 3.5–3.8(7H, m), 6.33(1H, s), 7.00(1H, d), 7.3–7.5(6H, m), 7.69(2 H, d). |
| 16-3 | 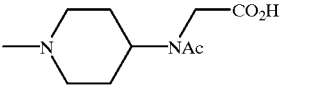 | — | pow. | NMR: (CDCl₃); 1.3–1.9(4H, m), 2.02(1.5H, s), 2.23(1.5H , s), 2.61(3H, s), 3.1–3.2(1H, m), 3.8–4.1(5H, m), 4.7 4.8(2H, m), 6.35(1H, s), 6.98(1H, t), 7.2–7.5(6H, m), 7.68(2H, d). |
| 17 | 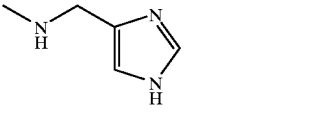 | — | pow. | NMR: (DMSO-d₆); 2.48(3H, s), 3.12(1H, br), 4.24(2H, br), 4.87(1H, br), 6.52(1H, s), 6.95(1H, br), 7.05(1H, d), 7.2 5–7.29(1H, m), 7.38–7.48(6H, m), 7.57(1H, br), 7.73–7.7 5(2H, m), 8.62(1H, br), 11.87(1H, br). |
| 17-1 | 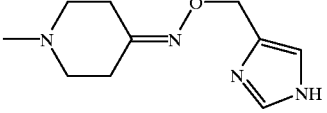 | HCl | pow. | NMR: (DMSO-d₆); 2.33–2.35(1H, m), 2.52(3H, s), 5.06(2H, s), 6.84(1H, m), 7.14(1H, d), 7.30–7.35(1H, m), 7.42–7.50(5H, m), 7.56–7.58(1H, m), 7.69–7.76(3H, m), 9.10(1 H, s). |
| 17-2 | 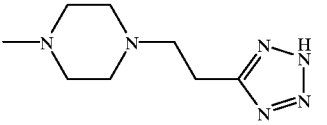 | — | amo. | NMR: (CDCl₃); 2.62(3H, s), 2.83(2H, br), 3.17(2H, br), 3.71(2H, br), 6.37(1H, s), 6.99(1H, d), 7.27–7.46(6H, m), 7.66–7.68(2H, m). |

TABLE 11-continued

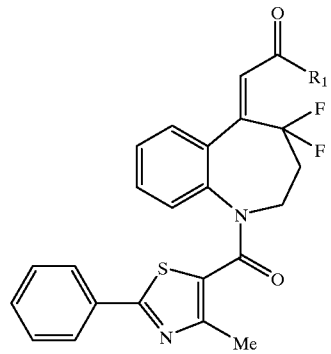

| Ex. | R₁ | Sal. | For. | NMR |
|---|---|---|---|---|
| 18 | 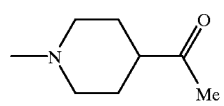 | — | yamo. | NMR: (CDCl₃); 1.37(3H, br), 2.06(3H, s), 2.36–2.42(3H, m), 2.74(3H, s), 3.65–3.69(1H, m), 6.78(1H, s), 7.05(1H, d), 7.23–7.42(6H, m), 7.74–7.76(2H, m). |
| 19 | 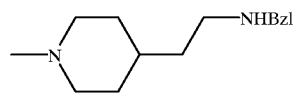 | HCl | pow. | NMR: (DMSO-d₆); 2.60(3H, s), 4.13(2H, br), 6.77(1H, s), 7.12(1H, d), 7.29–7.34(1H, m), 7.43–7.51(10H, m), 7.74–7.76(2H, m). |
| 20 | 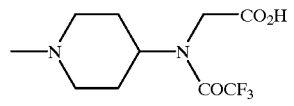 | — | amo. | NMR: (CDCl₃); 1.5–2.0(2H, m), 2.63(3H, s), 4.79(1H, m), 6.36(1H, s), 7.00(1H, d), 7.2–7.5(6H, m), 7.67(2H, d). |
| 21 | 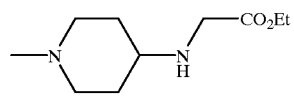 | — | amo. | NMR: (CDCl₃); 1.28(3H, t), 1.4–1.5(2H, m), 1.8–1.9(2H, m), 2.63(3H, s), 2.7–2.8(1H, m), 3.18(1H, t), 3.84(1H, d), 4.19(2H, q), 6.32(1H, s), 6.98(1H, m), 7.3–7.5(6H, m), 7.68(2H, d). |
| 22 | 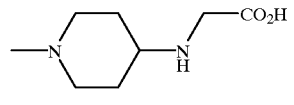 | — | ypow. | NMR: (CDCl₃); 2.59(3H, s), 6.37(1H, br), 6.97(1H, d), 7.3–7.5(6H, m), 7.67(2H, d). |
| 23 | 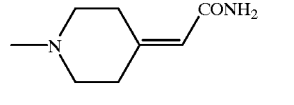 | — | pow. | NMR: (CDCl₃); 2.64(3H, s), 2.9–3.5(3H, br), 3.6–4.0(3H, br), 5.00(1H, br), 5.71(1H, d), 6.36(1H, s), 6.99(1H, d), 7.2–7.5(6H, m), 7.69(2H, d). |
| 24 | 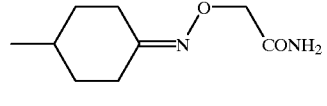 | — | ypow. | NMR: (DMSO-d₆); 2.52(3H, s), 4.32(2H, s), 6.85(1H, s), 7.13–7.14(2H, m), 7.26–7.34(2H, m), 7.41–7.49(4H, m), 7.57–7.59(1H, m), 7.74–7.76(2H, m). |
| 24-1 | 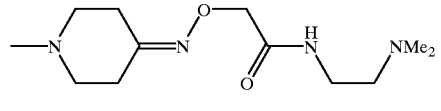 | HCl | amo. | NMR: (DMSO-d₆), 2.52(3H, s), 2.77–2.79(6H, m), 3.14–3.16(2H, m), 3.44–3.50(2H, m), 4.42(2H, s), 6.85(1H, s), 7.14(1H, d), 7.30–7.35(1H, m), 7.43–7.48(4H, m), 7.57–7.59(1H, m), 7.73–7.77(2H, m), 8.01–8.03(1H, m). |
| 24-2 | 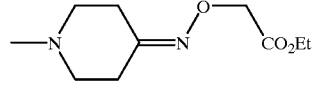 | — | amo. | NMR: (CDCl₃); 1.29(3H, t), 2.63(3H, s), 4.22(2H, q), 4.58(2H, s), 6.36(1H, s), 6.99(1H, d), 7.24–7.46(6H, m), 7.68–7.70(2H, m). |
| 25 | 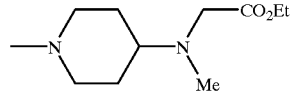 | HCl | pow. | NMR: (CDCl₃); 1.34(3H, t), 1.6–2.3(6H, m), 2.68(3H, s), 2.99(3H, s), 3.16(1H, m), 3.7–4.2(4H, m), 4.29(2H, q), 4.81(1H, br), 6.36(1H, s), 6.97(1H, d), 7.3–7.5(6H, m), 7.71(2H, d). |

TABLE 11-continued

| Ex. | R₁ | Sal. | For. | NMR |
|---|---|---|---|---|
| 25-1 | [piperidine-N(Me)Boc] | — | amo. | NMR: (CDCl₃); 1.46(9H, s), 2.63(3H, s), 2.70(3H, s), 3.95(1H, br), 4.74(1H, br), 6.33(1H, s), 6.98(1H, d), 7.3–7.5(6H, m), 7.69(2H, d). |
| 25-2 | [piperidine-N(CH₂CO₂Et)(COCF₃)] | — | yamo. | NMR: (CDCl₃); 1.28(3H, t), 1.8–2.0(1H, m), 2.63(3H, s), 4.0–4.3(5H, m), 4.7–4.8(1H, m), 6.33(1H, s), 6.99(1H, d), 7.3–7.5(6H, m), 7.69(2H, d). |
| 25-3 | [piperazine-CH₂CH₂-tetrazole-NTr] | — | yamo. | NMR: (CDCl₃); 2.47–2.49(3H, m), 2.63(3H, s), 2.83(2H, t), 3.11(2H, t), 3.45(2H, m), 6.30(1H, s), 6.98(1H, s), 7.08–7.44(21H, m), 7.68–7.70(2H, m). |
| 26 | [ketopiperazine-CH₂CO₂H] | — | pow. | NMR: (CDCl₃); 2.60(3H, s), 3.8–4.0(1H, m), 4.26(1H, br), 6.33(1H, m), 6.94(1H, d), 7.2–7.5(6H, m), 7.67(2H, br). |
| 27 | [ketopiperazine-CH₂CO₂Et] | — | amo. | NMR: (CDCl₃); 1.28(3H, t), 2.63(3H, s), 3.49(2H, m), 3.81(1H, m), 3.96(1H, m), 4.2–4.4(3H, m), 6.31(1H, s), 6.99(1H, m), 7.3–7.5(6H, m), 6.7–6.8(2H, m). |
| 28 | [piperazine-NAc] | — | amo. | NMR: (CDCl₃); 2.14(3H, d), 2.64(3H, s), 6.32(1H, s), 7.00(1H, d), 7.3–7.5(6H, m), 7.69(2H, d). |
| 29a | [piperidine-CH(OH)CH₂OH] | — | amo. | NMR: (CDCl₃); 1.26–1.35(2H, m), 1.86–1.90(1H, m), 2.40(1H, br), 2.63(3H, s), 2.92–3.12(2H, m), 3.65(1H, br), 3.84–3.91(3H, m), 4.65(1H, br), 6.33(1H, s), 6.96–6.99(1H, m), 7.22–7.27(1H, m), 7.34–7.38(4H, m), 7.44–7.47(1H, m), 7.68–7.71(2H, m). |
| 29b | [piperidine-CH(OH)CO₂Et] | — | amo. | NMR: (CDCl₃); 1.25–1.36(6H, m), 1.65(2H, br), 2.63(3H, s), 3.04–3.23(2H, m), 3.80(1H, br), 3.92–3.96(1H, m), 4.17(2H, q), 4.65–4.69(1H, m), 6.33(1H, s), 6.97(1H, d), 7.22–7.27(1H, m), 7.32–7.37(4H, m), 7.44–7.47(1H, m), 7.68–7.70(2H, m). |

Also, the compounds whose chemical structures are given in Table 12 can be easily produced in substantially the same manners as in the above-described Examples or Manufacturing Methods, or by applying slightly modified manners that are obvious to those persons skilled in the art.

TABLE 12

| No. | R | A | No. | R | A | No. | R | A |
|---|---|---|---|---|---|---|---|---|
| 1a | —Me | | 10a | —Me | | 19a | —Me | |
| 1b | —(CH$_2$)$_2$OH | | 10b | —(CH$_2$)$_2$OH | | 19b | —(CH$_2$)$_2$OH | |
| 2a | —Me | | 11a | —Me | | 20a | —Me | |
| 2b | —(CH$_2$)$_2$OH | | 11b | —(CH$_2$)$_2$OH | | 20b | —(CH$_2$)$_2$OH | |
| 3a | —Me | | 12a | —Me | | 21a | —Me | |
| 3b | —(CH$_2$)$_2$OH | | 12b | —(CH$_2$)$_2$OH | | 21b | —(CH$_2$)$_2$OH | |
| 4a | —Me | | 13a | —Me | | 22a | —Me | |
| 4b | —(CH$_2$)$_2$OH | | 13b | —(CH$_2$)$_2$OH | | 22b | —(CH$_2$)$_2$OH | |
| 5a | —Me | | 14a | —Me | | 23a | —Me | |
| 5b | —(CH$_2$)$_2$OH | | 14b | —(CH$_2$)$_2$OH | | 23b | —(CH$_2$)$_2$OH | |
| 6a | —Me | | 15a | —Me | | 24a | —Me | |
| 6b | —(CH$_2$)$_2$OH | | 15b | —(CH$_2$)$_2$OH | | 24b | —(CH$_2$)$_2$OH | |
| 7a | —Me | | 16a | —Me | | 25a | —Me | |
| 7b | —(CH$_2$)$_2$OH | | 16b | —(CH$_2$)$_2$OH | | 25b | —(CH$_2$)$_2$OH | |

TABLE 12-continued

| No. | R | A | No. | R | A | No. | R | A |
|---|---|---|---|---|---|---|---|---|
| 8a | —Me | oxazole-Me | 17a | —Me | pyrrole-Me (N-Me) | 26a | —Me | pyrazole-Me (N-Me) |
| 8b | —(CH₂)₂OH | | 17b | —(CH₂)₂OH | | 26b | —(CH₂)₂OH | |
| 9a | —Me | pyrrole-Me (NH) | 18a | —Me | furan-Me | 27a | —Me | triazole-Me (N-Me) |
| 9b | —(CH₂)₂OH | | 18b | —(CH₂)₂OH | | 27b | —(CH₂)₂OH | |

What is claimed is:

1. 4,4-Difluoro-2,3,4,5-tetrahydro-1H-1-benzoazepine compounds represented by the following formula (I) or salts thereof:

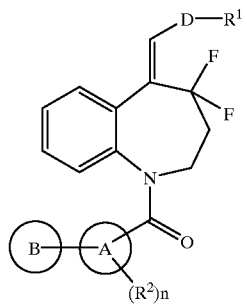

(I)

(wherein each of the symbols has the following meaning:
ring A: a 5-membered heteroarylene group;
ring B: an optionally substituted aryl group or a 5- to 6-membered heteroaryl group;
D: a carbonyl group or a lower alkylene group;
$R^1$: a group represented by formula, $NR^3R^4$, an —O-lower alkyl group, or OH;
$R^2$: an optionally halogen atom-substituted lower alkyl group, an —O-lower alkyl group, an —S-lower alkyl group, or a —CO-lower alkyl group;
$R^3$, $R^4$: same or different and each is
1) a hydrogen atom,
2) a lower alkyl group (the lower alkyl group may be substituted with OH, an optionally protected amino group, an optionally protected mono-lower alkylamino group, a di-lower alkylamino group, an optionally lower alkyl group-substituted 5- to 7-membered saturated heterocyclic group, a 5- to 6-membered heteroaryl group, or an aryl group),
3) a cycloalkyl group,
4) an optionally lower alkyl group-substituted 5- to 7-membered saturated heterocyclic group,
5) a 5- to 6-membered heteroaryl group,
6) an aryl group, or
7) an optionally substituted 5- to 7-membered nitrogen-containing heterocyclic group formed by integration of the formula, $NR^3R^4$ (the 5- to 7-membered nitrogen-containing heterocyclic group may be fused with a benzene ring or with a 5- to 6-membered heteroaryl group);
(in the 5- to 7-membered saturated heterocyclic group, the 5- to 7-membered nitrogen-containing heterocyclic group and the 5- to 6-membered heteroaryl group in the above 2), 4), 5) and 7), a group having a cyclic secondary amine may be one wherein the amine is protected); and
n: 0, 1 or 2.

2. The benzoazepine compounds or salts thereof according to claim 1, wherein the ring A is a thiazole ring, an imidazole ring or a pyrazole ring.

3. The benzoazepine compounds or salts thereof according to claim 1, wherein the ring A is a thiazole ring, an imidazole ring or a pyrazole ring, and $R^1$ is an optionally-substituted piperidine ring group or piperazine ring group.

4. A compound according to claim 1, wherein the compound is selected from the group consisting of 2-(4-{[4,4-Difluoro-1-(4-methyl-2-phenylthiazole-5-carbonyl)-2,3,4,5-tetrahydro-1H-1-benzoazepin-5-ylidene]-acetyl}piperazin-1-yl)ethanol; (1-{[4,4-difluoro-1-(4-methyl-2-phenylthiazole-5-carbonyl)-2,3,4,5-tetrahydro-1H-1-benzoazepin-5-ylidene]acetyl}-4-piperidyl)methanol; (1-{[4,4-difluoro-1-(4-methyl-2-phenylthiazole-5-carbonyl)-2,3,4,5-tetrahydro-1H-1-benzoazepin-5-ylidene]

acetyl}-4-piperidyl)carboxamide; N-acetic-N'-(1-{[4,4-difluoro-1-(4-methyl-2-phenylthiazole-5-carbonyl)-2,3,4,5-tetrahydro-1H-1-benzoazepin-5-ylidene]acetyl}piperidin-4-ylidene)hydrazide; 3-(1-{[4,4-difluoro-1-(4-methyl-2-phenylthiazole-5-carbonyl)-2,3,4,5-tetrahydro-1H-1-benzoazepin-5-ylidene]acetyl}-4-piperidyl)propionic acid; 4,4-difluoro-5-[2-(4-methylpiperazine-1-yl)-2-oxoethylidene]-1-(1-phenyl-5-trifluoromethyl-1H-pyrazole-4-carbonyl)-2,3,4,5-tetrahydro-1H-1-benzoazepine; 2-(4-{[4,4-difluoro-1-(1-phenyl-5-trifluoromethyl-1H-pyrazole-4-carbonyl)-2,3,4,5-tetrahydro-1H-1-benzoazepin-5-ylidene]-acetyl}piperazin-1-yl)ethanol; (4-{[4,4-difluoro-1-(1-phenyl-5-trifluoromethyl-1H-pyrazole-4-carbonyl)-2,3,4,5-tetrahydro-1H-1-benzoazepin-5-yl-idene]acetyl}piperazine-1-yl)acetamide; 4,4-difluoro-1-(5-ethyl-1-phenyl-1H-pyrazole-4-carbonyl)-5-[2-(4-methyl-piperazin-1-yl)-2-oxoethylidene]-2,3,4,5-tetrahydro-1H-1-benzoazepine; 1-{[4,4-difluoro-1-(1-phenyl-5-trifluoro-methyl-1H-imidazole-4-carbonyl)-2,3,4,5-tetrahydro-1H-1-benzoazepin-5-ylidene]acetyl}piperidin one; and salts thereof.

5. A pharmaceutical composition containing the 4,4-difluoro-2,3,4,5-tetrahydro-1H-1-benzoazepine compound or its salt according to claim 1 and a pharmaceutically acceptable carrier.

6. A method of treating a condition selected from the group consisting of threatened premature birth or abortion, dysmenorrhea, contraction of uterine smooth muscle, release of milk, endometriosis, need for feeding control, disturbance of memory, natriuresis, need for carbohydrate metabolism regulation, prostatic hypertrophy, breast cancer, need for regulation of ovulatory and luteal functions, need for regulation of sperm transportation, need for regulation of sexual behavior, and need for regulation of maternal behavior, comprising administering a therapeutically effective amount of oxytocin antagonist to a patient, wherein said oxytocin antagonist comprises a 4,4-difluoro-2,3,4,5-tetrahydro-1H-1-benzoazepine compound or its salt according to claim 1 and a pharmaceutically acceptable carrier.

* * * * *

UNITED STATES PATENT AND TRADEMARK OFFICE
CERTIFICATE OF CORRECTION

PATENT NO. : 6,340,678 B1
DATED : January 22, 2002
INVENTOR(S) : Matsuhisa et al.

Page 1 of 1

It is certified that error appears in the above-identified patent and that said Letters Patent is hereby corrected as shown below:

Column 89,
Line 20, "piperidin one" should read -- piperidin-4-one --.

Signed and Sealed this

Seventh Day of May, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 6,340,678 B1
DATED : January 22, 2002
INVENTOR(S) : Matsuhisa et al.

It is certified that error appears in the above-identified patent and that said Letters Patent is hereby corrected as shown below:

Column 6,
Line 20, "benzazepine" should be -- benzoazepine --.

Column 7,
Line 60, "(WSC.HCl)" should be -- (WSC•HCl) --.

Column 8,
Line 13, "benzazepine" should be -- benzoazepine --.

Column 9,
Structure (IV), "NHR$^3$R$^4$" should be -- HNR$^3$R$^4$ --.

Column 13,
Line 13, "*Igaku*" should be -- *Ika* --.
Line 21, "Preparation of Uterine membrane" should be -- Uterine membrane --.
Line 67, "scattered" should be -- scachard --.

Column 14,
Line 3, "bound" should be -- binding --.
Line 5, "bond to" should be -- bound to --.

Column 17,
Line 10, "The resulting crystals" should be -- These crystals --.

Column 20,
Line 60, "methylthiazole" should be -- methyl-2-phenylthiazole --.

Column 21,
Line 49, "ylidene]-acetamide" should be -- ylidene]acetamide --.
Line 61, "After making into a hydrochloride using a 4N HCl/ethyl acetate solution, the salt was collected" should be -- After dealing with a 4N HCl/ethyl acetate solution, the resulting salt was collected --.

UNITED STATES PATENT AND TRADEMARK OFFICE
CERTIFICATE OF CORRECTION

PATENT NO. : 6,340,678 B1
DATED : January 22, 2002
INVENTOR(S) : Matsuhisa et al.

It is certified that error appears in the above-identified patent and that said Letters Patent is hereby corrected as shown below:

Column 22,
Line 19, "1methyl" should be -- 1-methyl --.
Line 26, "methyl]-piperidino" should be -- methyl]piperidino --.
Line 34, "after making into a hydrochloride using a 4N HCl/ethyl acetate solution, the salt was collected" should be -- after dealing with a 4N HCl/ethyl acetate solution, the resulting salt was collected --.
Line 38, "2phenyl-thiazole" should be -- 2-phenylthiazole --.
Line 64, "4--methyl" should be -- 4-methyl --.

Column 23,
Line 33, "methyl]-acetamide" should be -- methyl]acetamide --.

Column 24,
Line 8, "monohydro-chloride" should be -- monohydrochloride --.
Line 35, "piperdino)" should be -- piperidino} --.
Line 44, "piperidyl)-(trifluoroacetyl)" should be -- piperidyl)(trifluoroacetyl) --.
Line 49, "(a washing A)" should be -- (a washing A). --.
Line 67, "ethyl(Z)" should be -- ethyl (Z) --.

Column 25,
Line 10, "piperidyl)-(trifluoroacetyl)" should be -- piperidyl)(trifluoroacetyl) --.
Line 28, "5-yl-idene" should be -- 5-ylidene --.
Line 39, "dimethylamino-propyl" should be -- dimethylaminopropyl --.

Column 26,
Line 12, "methyl-yl2" should be -- methyl-2 --.
Line 38, "carbonyl-yl" should be -- carbonyl --.

Column 29,
Ex. 2-1, "amo" should be -- amo. --.

UNITED STATES PATENT AND TRADEMARK OFFICE
CERTIFICATE OF CORRECTION

PATENT NO.    : 6,340,678 B1
DATED         : January 22, 2002
INVENTOR(S)   : Matsuhisa et al.

It is certified that error appears in the above-identified patent and that said Letters Patent is hereby corrected as shown below:

Column 32,
Ex. 3, "(DMSO-$d_{61)}$" should be -- (DMSO-$d_6$) --.
Ex. 3-6, "7.7.3-7.5" should be -- 7.3-7.5 --.
Ex. 3, ";$_{2.4-2.5...10.86(1H, br)}$." should be --; 2.4-2.5 . . .10.86(1H, br). --.

Column 33,
Ex. 3-16,

Column 34,
Ex. 3-14, "2,.44" should be -- 2.44 --.

Column 37,
Ex. 3-35, "amo" should be -- amo. --.

Column 38,
Ex. 3-30, "635" should be -- 6.35 --.
Ex. 3-36, "4.0-4.2(3H, m), 3.4-3.5(2H, m)" should be -- 3.4-3.5(2H, m), 4.0-4.2 (3H, m) --.

Column 40,
Ex. 3-44, "3.69-4.55(1H, br)" should be -- 3.69-4.55(11H, br) --.

Column 45,
Ex. 3-66,

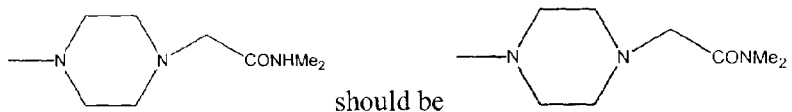

Column 49,
Ex. 3-89, "pow" should be -- pow. --.
Ex. 3-91, "pow" should be -- pow. --.

Column 51,
Ex. 4-6, "7.16(1H, br)" should be -- 7.16(1H, d) --.

UNITED STATES PATENT AND TRADEMARK OFFICE
CERTIFICATE OF CORRECTION

PATENT NO. : 6,340,678 B1
DATED : January 22, 2002
INVENTOR(S) : Matsuhisa et al.

It is certified that error appears in the above-identified patent and that said Letters Patent is hereby corrected as shown below:

Column 61,
Ex. 7-1,

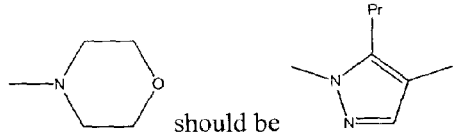 should be

Column 63,
Ex. 7-12, "7.62-7.90 2H, m)." should be -- 7.62-7.90(2H, m). --.

Column 76,
Ex. 13-1, "2(3H, s)" should be -- 2.52(3H, s) --.
Ex. 9-2, "7.12(1h, d)" should be -- 7.12(1H, d) --.

Column 77,
Ex. 14-7,

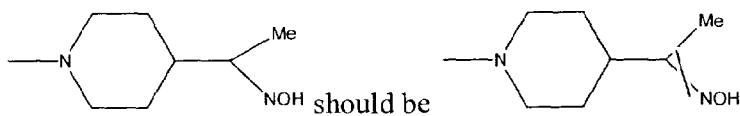

Column 79,
Ex. 15,

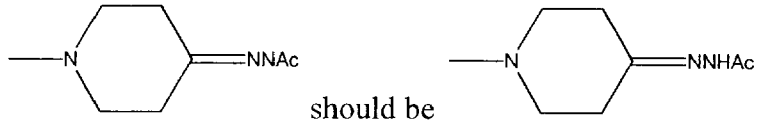

UNITED STATES PATENT AND TRADEMARK OFFICE
CERTIFICATE OF CORRECTION

PATENT NO.   : 6,340,678 B1
DATED        : January 22, 2002
INVENTOR(S)  : Matsuhisa et al.

It is certified that error appears in the above-identified patent and that said Letters Patent is hereby corrected as shown below:

<u>Column 89,</u>
Line 1, "N-acetic" should be -- N-acetyl --.
Line 7, "[piperazine-1-yl]" should be -- [piperazin-1-yl] --.
Line 14, "5-yl-idene" should be -- 5-ylidene --.
Line 14, "piperazine-1-yl" should be -- piperazin-1-yl --.
Line 16, "methyl-piperazin" should read -- methylpiperazin --.
Line 18, "trifluoro-methyl" should read -- trifluoromethyl --.

Signed and Sealed this

Twenty-fourth Day of September, 2002

Attest:

JAMES E. ROGAN
*Attesting Officer*   *Director of the United States Patent and Trademark Office*